US012616663B2

(12) United States Patent
    Zhang

(10) Patent No.: US 12,616,663 B2
(45) Date of Patent: May 5, 2026

(54) PLANT-DERIVED EXOSOME-LIKE NANOPARTICLES INHIBIT BACTERIAL PATHOGENICITY

(71) Applicant: University of Louisville Research Foundation, Inc., Louisville, KY (US)

(72) Inventor: Huang-Ge Zhang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 889 days.

(21) Appl. No.: 17/435,650

(22) PCT Filed: Mar. 2, 2020

(86) PCT No.: PCT/US2020/020675
§ 371 (c)(1),
(2) Date: Sep. 1, 2021

(87) PCT Pub. No.: WO2020/180801
PCT Pub. Date: Sep. 10, 2020

(65) Prior Publication Data
US 2022/0142937 A1      May 12, 2022

Related U.S. Application Data

(60) Provisional application No. 62/812,644, filed on Mar. 1, 2019.

(51) Int. Cl.
    *A61K 9/51*        (2006.01)
    *A61K 9/00*        (2006.01)
    *A61K 36/9068*     (2006.01)
    *A61P 31/04*       (2006.01)
    *B82Y 5/00*        (2011.01)
    *B82Y 40/00*       (2011.01)

(52) U.S. Cl.
    CPC .......... *A61K 9/5176* (2013.01); *A61K 9/0053* (2013.01); *A61K 36/9068* (2013.01); *A61P 31/04* (2018.01); *B82Y 5/00* (2013.01); *B82Y 40/00* (2013.01)

(58) Field of Classification Search
    CPC .............. A61K 9/5176; A61K 9/0053; A61K 36/9068; A61K 9/0063; A61K 9/5184; A61K 47/24; A61P 31/04; B82Y 5/00; B82Y 40/00; A01K 2227/105; A01K 2267/0337
    See application file for complete search history.

(56) References Cited

U.S. PATENT DOCUMENTS

| | | |
|---|---|---|
| 2016/0354370 A1 | 12/2016 | Reid |
| 2018/0177816 A1 | 6/2018 | Shiku et al. |
| 2018/0271925 A1 | 9/2018 | Choi et al. |

OTHER PUBLICATIONS

Bahri F et al "A comprehensive review on ginger-derived exosome-like nanoparticles as feasible therapeutic nano-agents against diseases" Mater Adv, 2024, 5, 1846-1867; doi: 10.1039/d3ma00856h. (Year: 2024).*

Sundaram K, et al "Plant-Derived Exosomal Nanoparticles Inhibit Pathogenicity of Porphyromonas gingivalis" iScience, Nov. 22, 2019 (Epub Oct. 12, 2019), 21, pp. 308-327; doi: 10.1016/j.isci.2019.10.032. (Year: 2019).*

Non-Final Office Action for U.S. Appl. No. 17/435,650, dated Sep. 18, 2025, 10 pages.

International Preliminary Report on Patentability for International Application No. PCT/US2020/020675, dated Sep. 16, 2021, 16 Pages.

International Search Report and Written Opinion for International Application No. PCT/US2020/020675, dated Aug. 12, 2020, 20 Pages.

"Periodontal Disease," Feb. 21, 2019, XP055735580, Retrieved from URL: https://en.wikipedia.org/w/index.php?title=Periodontal_disease&oldid=884465240, 19 pages.

Rome, "Biological Properties of Plant-derived Extracellular Vesicles," Food Function, Feb. 6, 2019, pp. 529-538, XP009516785.

* cited by examiner

*Primary Examiner* — Aaron J Kosar

(74) *Attorney, Agent, or Firm* — Meunier Carlin & Curfman LLC

(57) ABSTRACT

Provided are methods for preventing and/or treating oral diseases, disorders, and/or conditions. In some embodiments, the methods relate to administering to the oral cavity of a subject in need thereof a composition that includes an effective amount of ginger-derived exosome-like nanoparticles (GELNs) or a biologically active component thereof. Also provided are methods for preventing and/or treating periodontitis, methods for reducing growth of and/or pathogenicity of microorganisms in the oral cavities of subjects, methods for reducing microorganismal motility, and methods for reducing bone loss in the oral cavities of subjects associated with infection with microorganisms. Also provided are compositions that can be employed in the disclosed methods.

10 Claims, 16 Drawing Sheets

Specification includes a Sequence Listing.

CONTROL GELNs

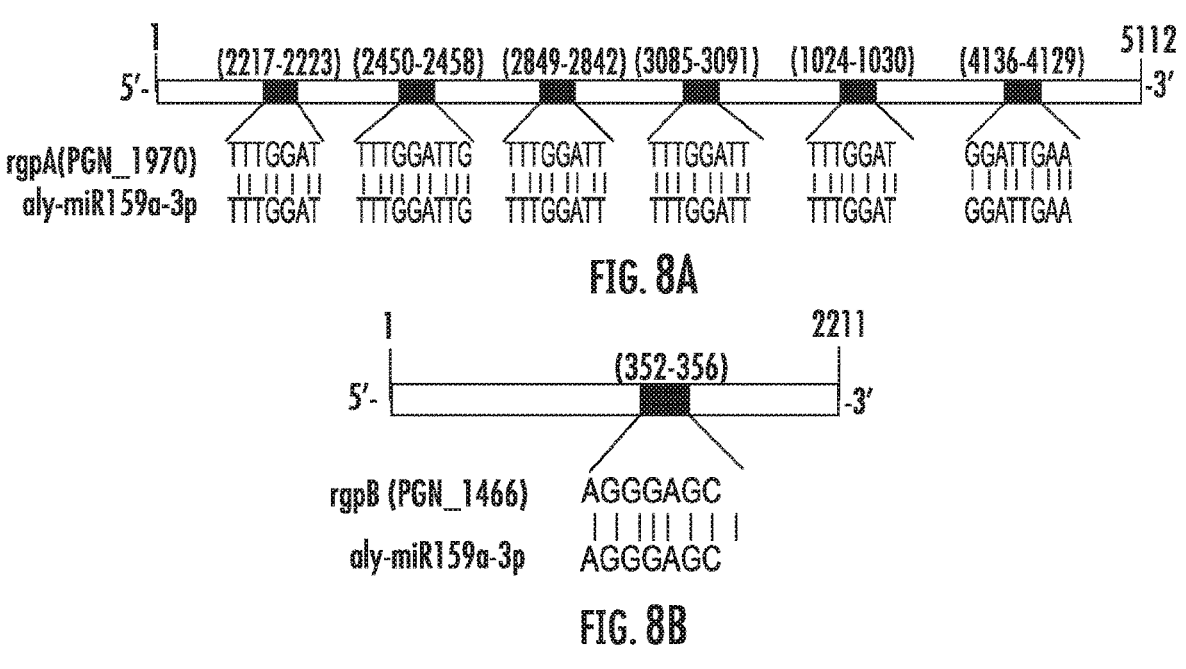
FIG. 8A
FIG. 8B
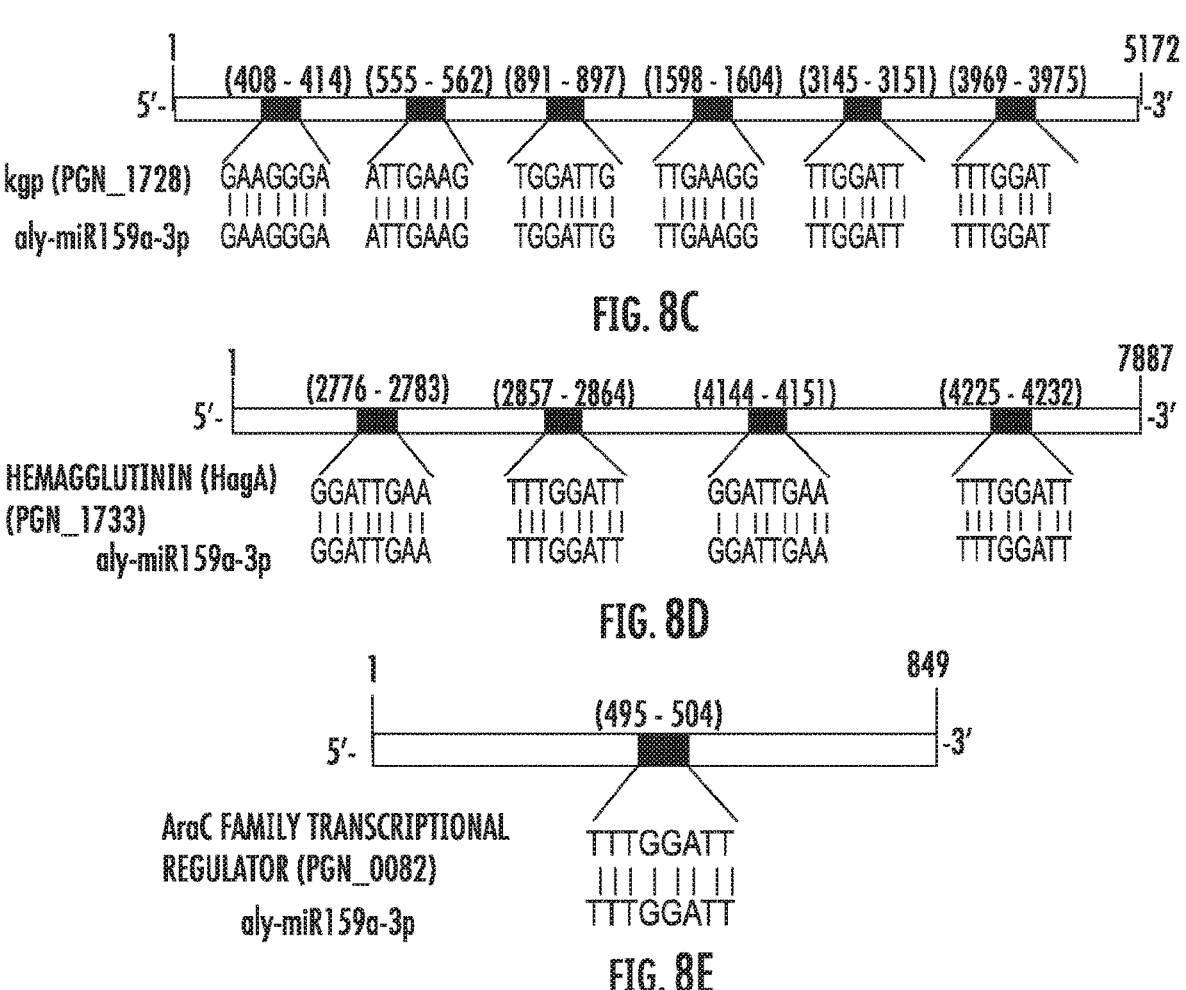
FIG. 8C
FIG. 8D
FIG. 8E

PLANT-DERIVED EXOSOME-LIKE NANOPARTICLES INHIBIT BACTERIAL PATHOGENICITY

CROSS-REFERENCE TO RELATED APPLICATIONS

This application is a United States National Phase Entry of PCT International Patent Application No. PCT/US2020/020675, filed Mar. 2, 2020, incorporated herein by reference in its entirety and which claims the benefit of U.S. Provisional Patent Application Ser. No. 62/812,644, filed Mar. 1, 2019, the disclosure of which is incorporated herein by reference in its entirety.

GOVERNMENT INTEREST

This invention was made with government support under R01 AT008617 and UH3 TR000875 awarded by the National Institutes of Health. The government has certain rights in the invention.

TECHNICAL FIELD

The presently disclosed subject matter relates to compositions and methods for preventing and/or treating diseases, disorders, and conditions associated with microbial infections in subjects. More particularly, the presently disclosed subject matter relates to compositions comprising effective amounts of ginger-derived exosome-like nanoparticles (GELNs) or one or more biologically active component thereof and methods of use thereof to prevent and/or treat microbial infections and consequences thereof, particularly but not limited to microbial infections and consequences thereof in the oral cavity.

BACKGROUND

Chronic infectious diseases commonly involve large numbers of virulence factors, which target to several host factors in multiple pathways. Developing an effective therapeutic strategy that can inhibit most virulence factors of any given microorganism without causing undesirable side effects can benefit from a change of focus from delivering individual therapeutic agents to delivering packages of therapeutic agents that can target multiple virulence factors simultaneously. Currently, no such delivery vehicle or strategy that selectively targets pathogens and carries multiple therapeutic agents without also causing significant toxicity is available.

Generally, edible plants are beneficial for human health and can help prevent and/or treat chronic infectious diseases. However, the cellular and molecular mechanisms underlying the therapeutic effects with respect to prevention and/or treatment of infectious disease are not known. Since ELNs naturally carry a large number and variety of molecules, it is possible that upon uptake of ELNs by infectious agents, ELN molecules could target multiple virulence factors simultaneously to prevent disease development. ELNs are derived from a healthy diet, and are unlikely to cause side-effects. As disclosed herein, ginger-derived ELNs (GELNs) were used to demonstrate that GELNs can have an effect on the prevention of *Porphyromonas gingivalis* (*P. gingivalis*) induced chronic periodontitis in a mouse model.

*Porphyromonas gingivalis* (*P. gingivalis*), a Gram-negative anaerobic bacterium, is the major prevalent bacterium that contributes to chronic periodontitis, an inflammatory disease associated with an alteration of local microbiota. Periodontitis has been associated with cardiovascular disease, type 2 diabetes mellitus, and adverse pregnancy outcomes with an increased risk for delivery of premature labor and low-birth-weight infants. *P. gingivalis* expresses many virulence factors, including fimbriae (fimA and mfa1), gingipain [arginine-(Rgp) and lysine specific (Kgp)] proteases, lipopolysaccharides, hemagglutinin, and hemolysins that play an important role in the pathogenicity of the bacterium via tissue colonization, destruction, and interference with the host immune system. Fimbriae are protein-based filamentous appendages that protrude from *P. gingivalis* and facilitate adhesion to host cells and to other bacteria. Tissue degradation caused by proteolytic enzymes released from *P. gingivalis* contributes to periodontal biofilm formation and excessive immune stimulation.

Orally delivering GELNs has been shown to lead to protection of mice against alcohol induced liver damage. That GELNs alter the gut microbiome composition and host physiology led us to test whether this strategy could be applied to treat and/or prevent oral infectious diseases. As disclosed herein, GELNs are selectively taken up by *P. gingivalis*, and upon being taken up, the pathogenicity of *P. gingivalis* is significantly reduced, including its growth, attachment, entry, proliferation in host cells, motility, and bone erosion in a mouse model.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter relates to methods for preventing and/or treating oral diseases, disorders, and/or conditions. In some embodiments, the methods comprise administering to the oral cavity of a subject in need thereof a composition comprising an effective amount of ginger-derived exosome-like nanoparticles (GELNs) or a biologically active component thereof. In some embodiments, the oral disease, disorder, and/or condition is periodontitis, alveolar bone loss, or a combination thereof. In some embodiments, the oral disease, disorder, or condition is associated with infection of a microorganism selected from the group consisting of *Porphyromonas gingivalis* (*P. gingivalis*), *Listeria monocytogenes* (*L. monocytogenes*), and *Clostridioides difficile* (*C. difficile*). In some embodiments, the biologically active component comprises a lipid, a protein, an miRNA, or a combination thereof. In some embodiments, the biologically active component comprises one or more miRNAs, optionally wherein the one or more miRNAs comprise an miR-159a-3p miRNA. In some embodiments, the biologically active component comprises one or more lipids, optionally wherein the one or more lipids comprises phosphatidic acid (PA). In some embodiments, the one or more lipids comprises PA (34:2).

In some embodiments, the presently disclosed subject matter also relates to methods for preventing and/or treating periodontitis. In some embodiments, the methods comprise administering to the oral cavity of a subject in need thereof a composition comprising an effective amount of ginger-derived exosome-like nanoparticles (GELNs) or a biologically active component thereof. In some embodiments, the periodontitis is associated with infection of a microorganism selected from the group consisting of *Porphyromonas gingivalis* (*P. gingivalis*), *Listeria monocytogenes* (*L. monocytogenes*), and *Clostridioides difficile* (*C. difficile*). In some embodiments, the biologically active component comprises a lipid, a protein, an miRNA, or a combination thereof. In some embodiments, the biologically active component comprises one or more miRNAs, optionally wherein the one or more miRNAs comprise an miR-159a-3p miRNA. In some embodiments, the biologically active component comprises one or more lipids, optionally wherein the one or more lipids comprises phosphatidic acid (PA). In some embodiments, the one or more lipids comprises PA (34:2).

In some embodiments, the presently disclosed subject matter also relates to methods for reducing growth of microorganisms in the oral cavity of a subject. In some embodiments, the methods comprise administering to the oral cavity of the subject a composition comprising an effective amount of ginger-derived exosome-like nanoparticles (GELNs) or a biologically active component thereof. In some embodiments, the microorganism is selected from the group consisting of *Porphyromonas gingivalis* (*P. gingivalis*), *Listeria monocytogenes* (*L. monocytogenes*), and *Clostridioides difficile* (*C. difficile*). In some embodiments, the biologically active component comprises a lipid, a protein, an miRNA, or a combination thereof. In some embodiments, the biologically active component comprises one or more miRNAs, optionally wherein the one or more miRNAs comprise an miR-159a-3p miRNA. In some embodiments, the biologically active component comprises one or more lipids, optionally wherein the one or more lipids comprises phosphatidic acid (PA). In some embodiments, the one or more lipids comprises PA (34:2).

In some embodiments, the presently disclosed subject matter also relates to methods for reducing pathogenicity of microorganisms in the oral cavity of a subject. In some embodiments, the methods comprise administering to the oral cavity of the subject a composition comprising an effective amount of ginger-derived exosome-like nanoparticles (GELNs) or a biologically active component thereof. In some embodiments, the microorganism is selected from the group consisting of *Porphyromonas gingivalis* (*P. gingivalis*), *Listeria monocytogenes* (*L. monocytogenes*), and *Clostridioides difficile* (*C. difficile*). In some embodiments, the biologically active component comprises a lipid, a protein, an miRNA, or a combination thereof. In some embodiments, the biologically active component comprises one or more miRNAs, optionally wherein the one or more miRNAs comprise an miR-159a-3p miRNA. In some embodiments, the biologically active component comprises one or more lipids, optionally wherein the one or more lipids comprises phosphatidic acid (PA). In some embodiments, the one or more lipids comprises PA (34:2).

In some embodiments, a composition for use in the presently disclosed methods is formulated as an oral rinse or as a gel, and/or is formulated to adhere to a biofilm.

In some embodiments, the presently disclosed subject matter also relates to methods for reducing motility of microorganisms. In some embodiments, the methods comprise contacting a microorganism with a composition comprising an effective amount of ginger-derived exosome-like nanoparticles (GELNs) or a biologically active component thereof. In some embodiments, the microorganism is selected from the group consisting of *Porphyromonas gingivalis* (*P. gingivalis*), *Listeria monocytogenes* (*L. monocytogenes*), and *Clostridioides difficile* (*C. difficile*). In some embodiments, the biologically active component comprises a lipid, a protein, an miRNA, or a combination thereof. In some embodiments, the biologically active component comprises one or more miRNAs, optionally wherein the one or more miRNAs comprise an miR-159a-3p miRNA. In some embodiments, the biologically active component comprises one or more lipids, optionally wherein the one or more lipids comprises phosphatidic acid (PA). In some embodiments, the one or more lipids comprises PA (34:2).

In some embodiments, the presently disclosed subject matter also relates to methods for reducing bone loss in the oral cavity of a subject associated with a microbial infection. In some embodiments, the methods comprise administering to the oral cavity of the subject a composition comprising an effective amount of ginger-derived exosome-like nanoparticles (GELNs) or a biologically active component thereof. In some embodiments, the microbial infection is by a microorganism selected from the group consisting of *Porphyromonas gingivalis* (*P. gingivalis*), *Listeria monocytogenes* (*L. monocytogenes*), and *Clostridioides difficile* (*C. difficile*), or any combination thereof. In some embodiments, the biologically active component comprises a lipid, a protein, an miRNA, or a combination thereof. In some embodiments, the biologically active component comprises one or more miRNAs, optionally wherein the one or more miRNAs comprise an miR-159a-3p miRNA. In some embodiments. the biologically active component comprises one or more lipids, optionally wherein the one or more lipids comprises phosphatidic acid (PA). In some embodiments, the one or more lipids comprises PA (34:2).

In some embodiments, the presently disclosed subject matter also relates to compositions for use in preventing and/or treating oral diseases, disorders, and/or conditions; and/or for preventing and/or treating periodontitis; and/or for reducing growth of a microorganism in the oral cavity of a subject; and/or for reducing pathogenicity of a microorganism in the oral cavity of a subject; and/or for reducing motility of a microorganism; and/or for reducing bone loss in the oral cavity of a subject associated with infection by a microorganism. In some embodiments, the compositions comprise an effective amount of ginger-derived exosome-like nanoparticles (GELNs) or a biologically active component thereof. In some embodiments, the microorganism is selected from the group consisting of *Porphyromonas gingivalis* (*P. gingivalis*), *Listeria monocytogenes* (*L. monocytogenes*), and *Clostridioides difficile* (*C. difficile*). In some embodiments, the biologically active component comprises a lipid, a protein, an miRNA, or a combination thereof. In some embodiments, the biologically active component comprises one or more miRNAs, optionally wherein the one or more miRNAs comprise an miR-159a-3p miRNA. In some embodiments, the biologically active component comprises one or more lipids, optionally wherein the one or more lipids comprises phosphatidic acid (PA). In some embodiments, the one or more lipids comprises PA (34:2).

Thus, it is an object of the presently disclosed subject matter to provide compositions and methods for preventing and/or treating microbial infections and consequences thereof, including but not limited to microbial infections and consequences thereof in the oral cavity.

5

Figure 1A:
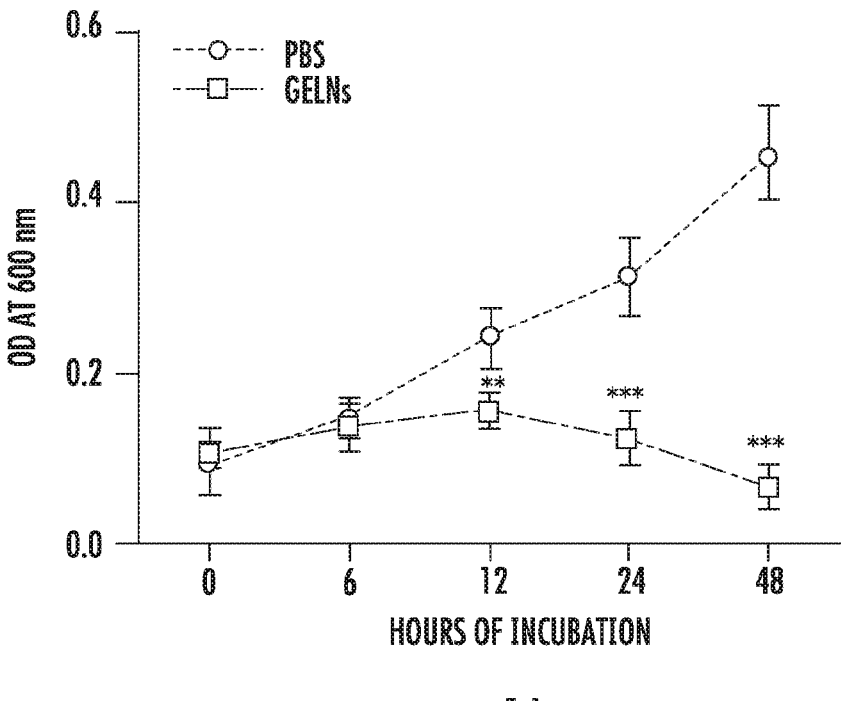
FIGS. 1A-1C present the results of experiments demonstrating that ginger-derived exosomes-like nanoparticles
Figure 1B:
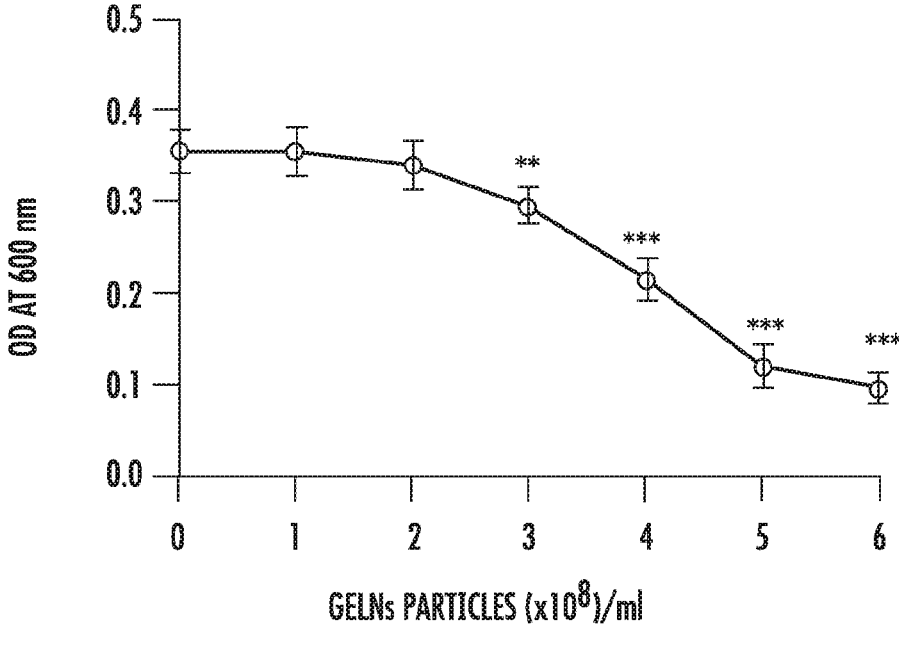
Figure 1C:
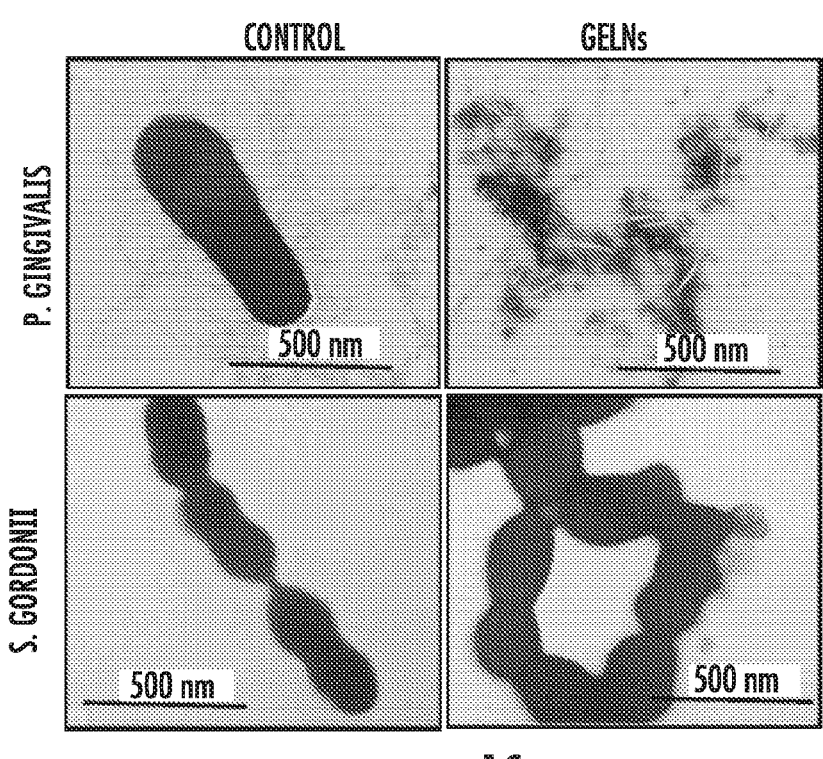

(GELNs) selectively inhibited pathogenic *P. gingivalis* growth but not commensal *S. gordonii*. FIG. 1A is a graph of the growth of *P. gingivalis* incubated with GELNs (4.0× $10^8$/ml) for indicated time periods. The growth of *P. gingivalis* was determined by measuring optical density at 600 nm. FIG. 1B is a graph of the growth of *P. gingivalis* treated with different concentration (0-6×$10^8$/ml) of GELNs and incubated at 37° C. for 24 hours. The growth of *P. gingivalis* was determined by measuring optical density at 600 nm. FIG. 1C is a series of Transmission electron microscopy (TEM) images of *P. gingivalis* and *S. gordonii* treated with GELNs (6×$10^8$/ml) or PBS as a negative control for 3 hours and negatively staining with ammonium molybdate. Results are expressed as means±one standard deviation from three independent experiments. p<0.01; *p<0.001 compared with untreated group using one-way ANOVA with Newman-Keuls Multiple comparison test.

Figure 2A:
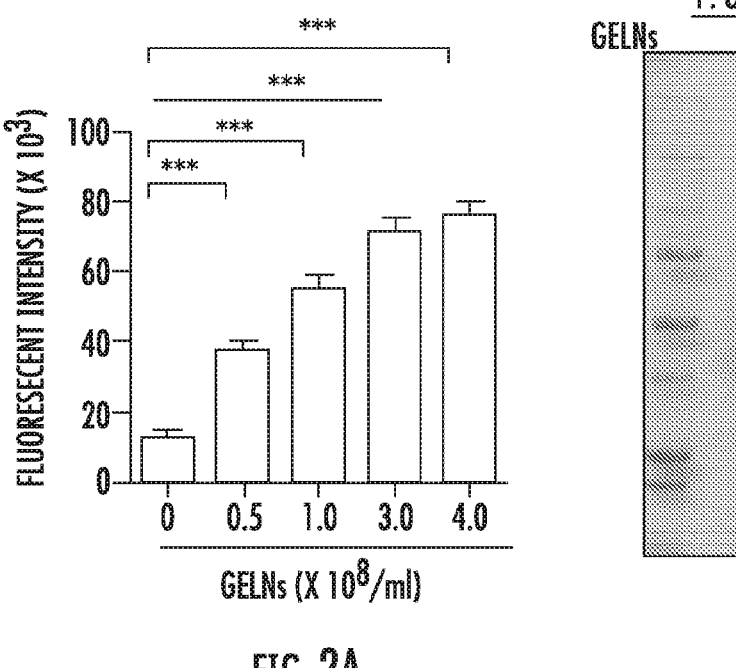
Figure 2B:
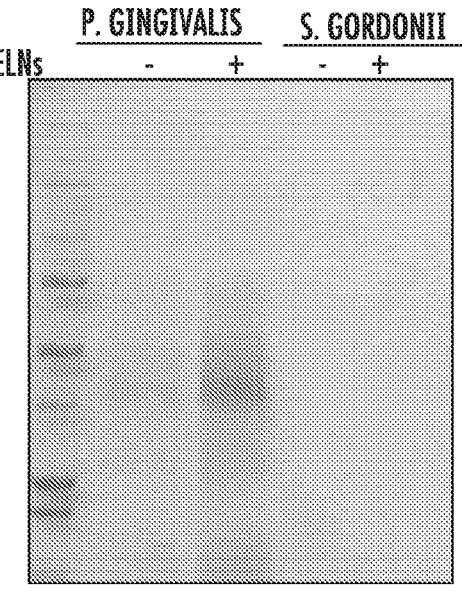

FIGS. 2A and 2B depict the results of experiments showing that ginger exosome-like nanoparticles (GELNs) modulated inner membrane depolarization and membrane fluidity in *P. gingivalis*. FIG. 2A is a bar graph of *P. gingivalis* incubated with different concentrations (0-6.0×$10^8$ particles/ml) of GELNs for 2 hours at 37° C., after which 0.5 μM of ethidium bromide was added. The fluorescent intensity was measured at 540 nm and 610 nm of excitation and emission respectively. FIG. 2B is an SDS-PAGE gel electrophoresis stained with Coomassie brilliant blue of *P. gingivalis* and *S. gordonii* treated with GELNs (4.0×$10^8$ particles/ml) for 24 hours and centrifuged (10000 rpm) for 10 minutes to remove bacteria. The supernatants were run on the SDS-PAGE gel. Results are expressed as means±standard deviation from three independent experiments. *p<0.05; p<0.01; *p<0.001 as compared to the untreated group using one-way ANOVA with Newman-Keuls Multiple Comparison Test.

Figure 3A:
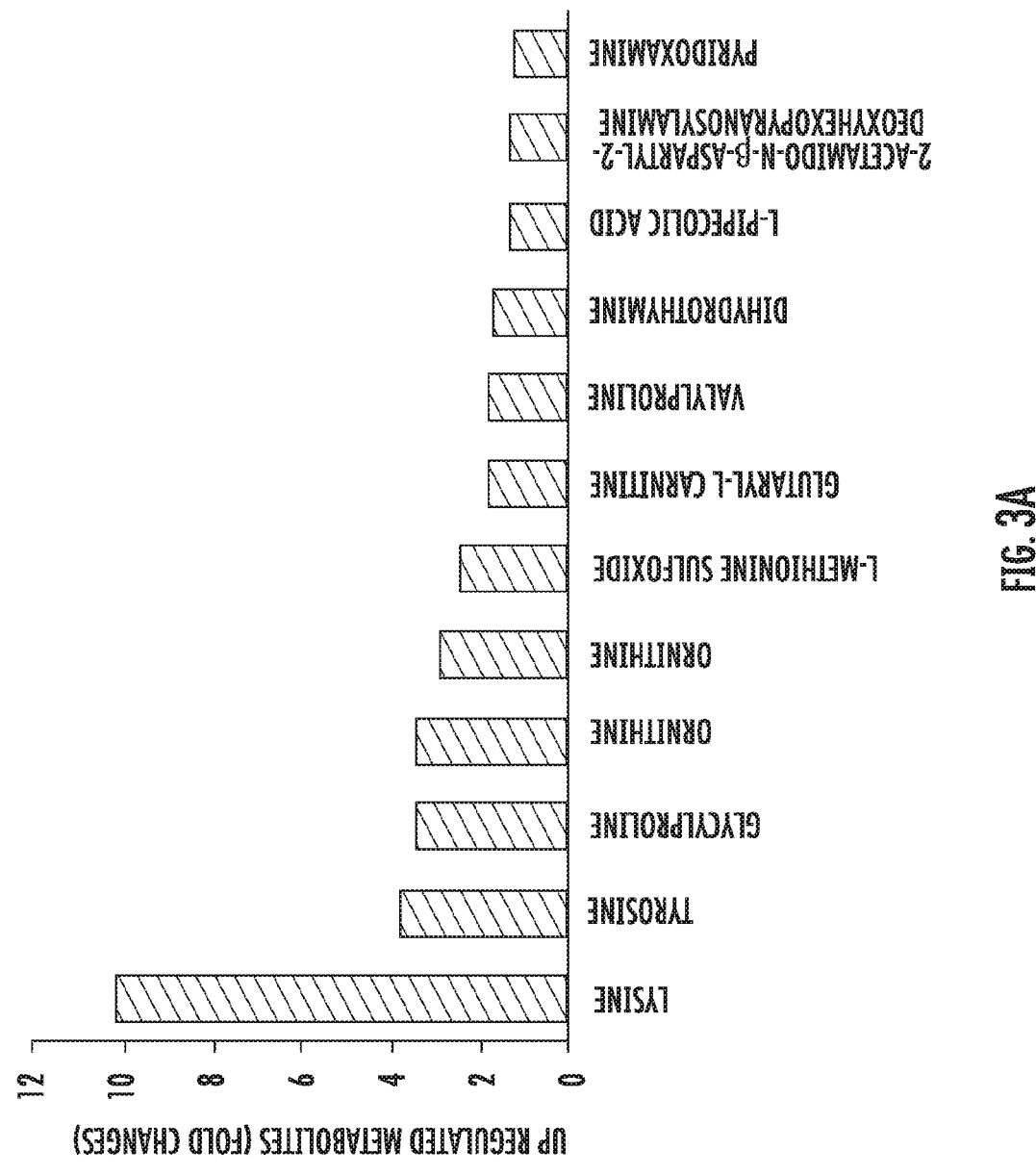
Figure 3B:
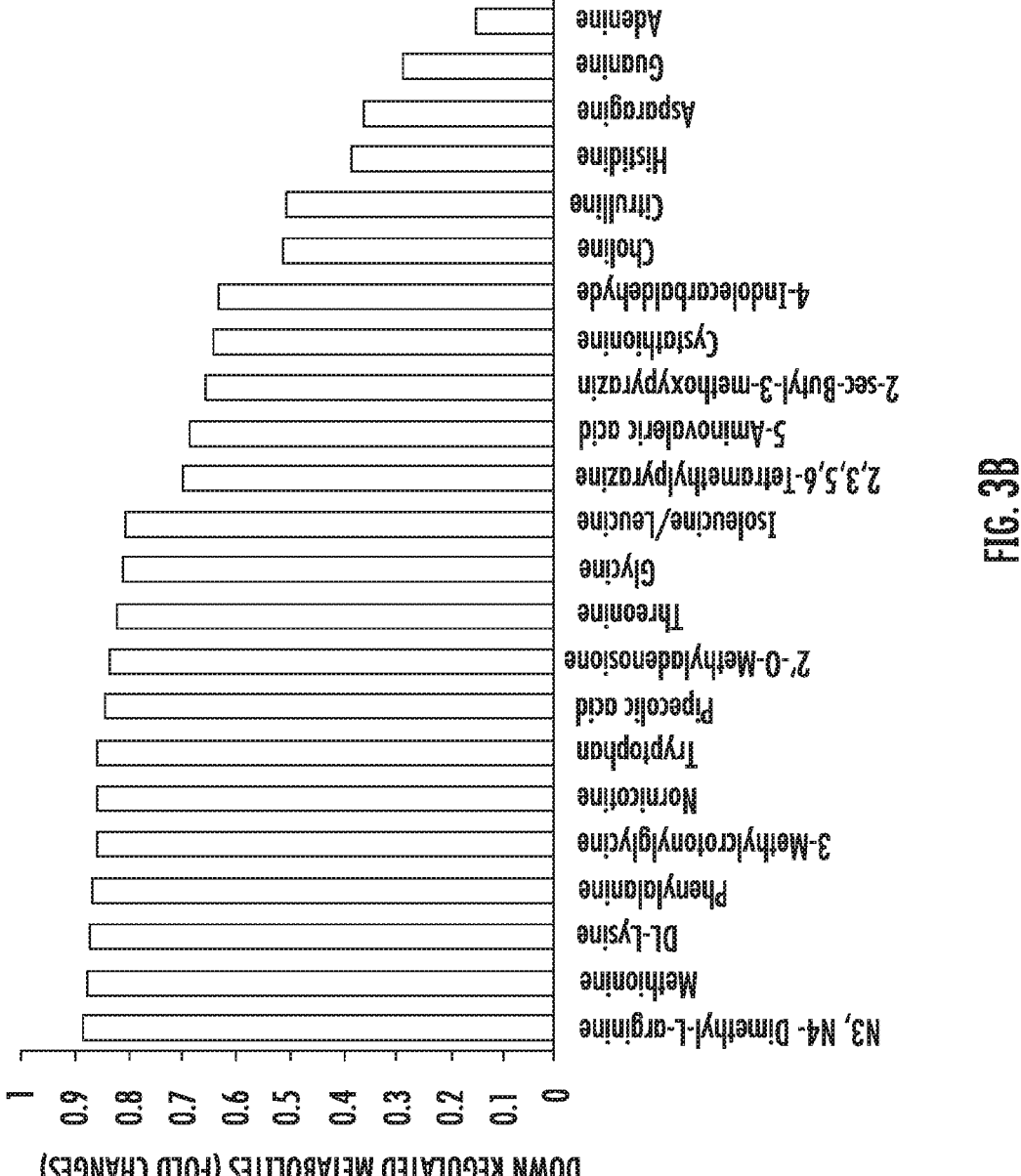

FIGS. 3A and 3B summarize the results of experiments showing that GELNs modulated metabolic pathways in *P. gingivalis*. *P. gingivalis* was treated with GELNs (4×$10^8$ particles/ml) for 24 hours. The supernatants were collected and metabolic products were measured by LC-MS. FIG. 3A is a bar graph of upregulated metabolic products, and FIG. 3B is a bar graph of down regulated metabolic products.

Figure 4A:
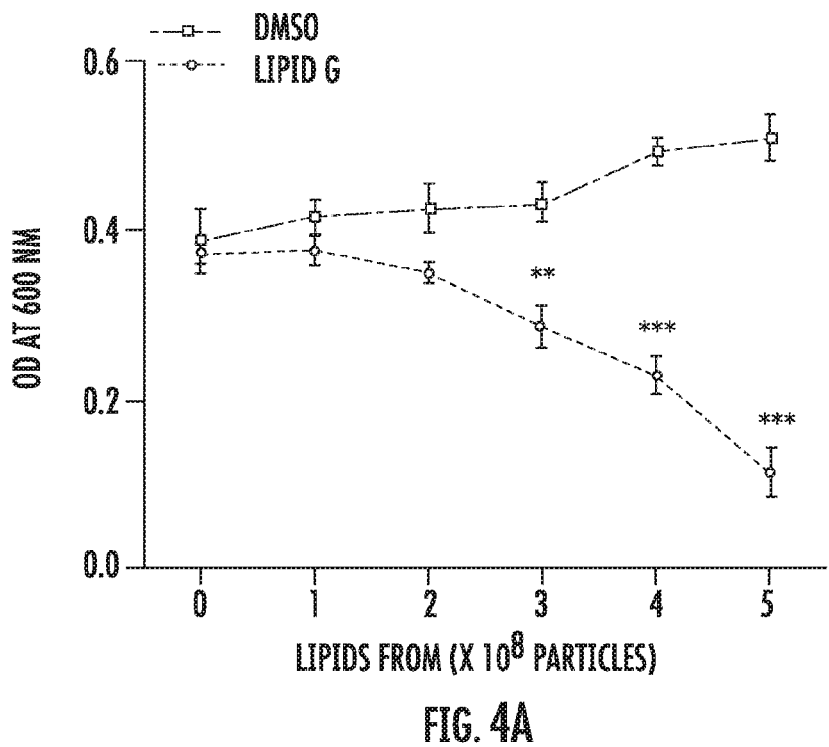
Figure 4C:
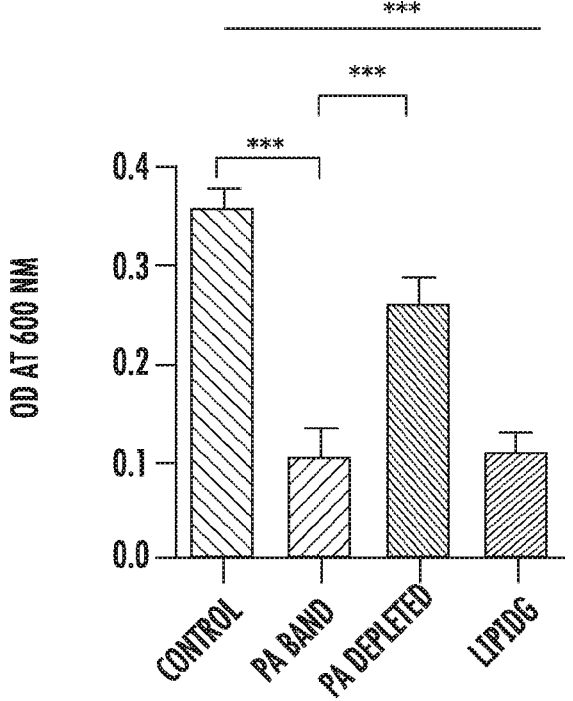
Figure 4B:
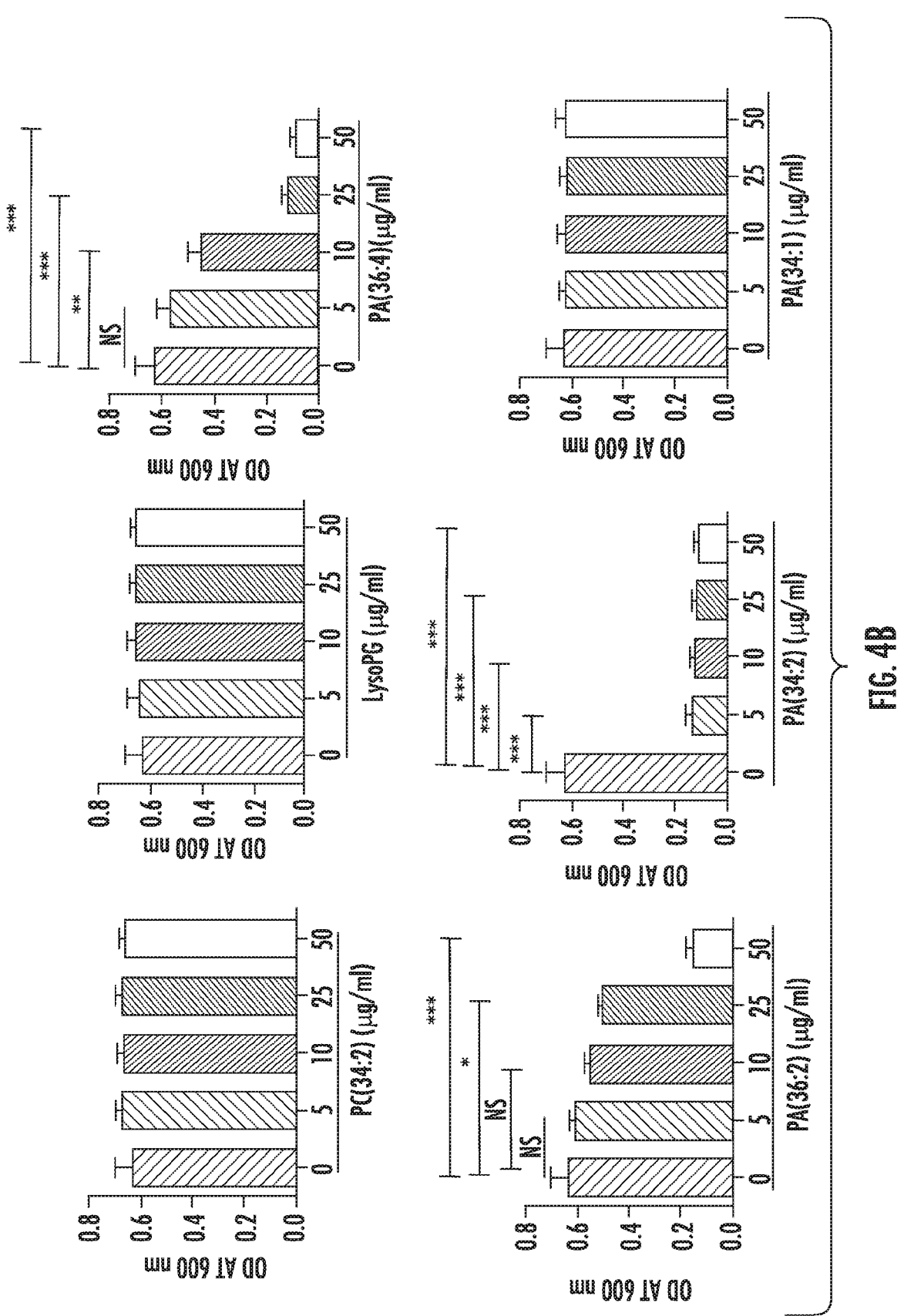

FIGS. 4A-4C depict the results of experiments showing that phosphatidic acid (PA)-containing lipids of GELNs inhibited *P. gingivalis* growth. FIG. 4A is a graph of bacterial growth determined by measuring optical density at 600 nm of *P. gingivalis* treated with GELNs total lipids (LipidG) isolated from different concentration of GELNs (0-5.0×$10^8$ particles) for 24 hours. FIG. 4B is a series of bar graphs of bacterial growth determined by measuring optical density at 600 nm of *P. gingivalis* treated with different concentration (0-50 μg/ml) of PC(34:2), LysoPG (18:1), PA(36:4), PA(36:2), PA(34:2), and PA(34:1) for 24 hours. FIG. 4C is a bar graph of bacterial growth measured at 600 nm of *P. gingivalis* treated with lipids from PA-containing band, PA-depleted band, and GELNs total lipids (LipidG) for 24 hours. Depletion of PA lipids in the total GELNs lipids (LipidG) was accomplished by eluting the corresponding PA band in the TLC plate and mixing the rest of the lipids. Results are expressed as means±standard deviation from three independent experiments. *p<0.05; p<0.01; *p<0.001 as compared to the untreated group using one-way ANOVA with Newman-Keuls Multiple Comparison Test.

6

Figure 5:
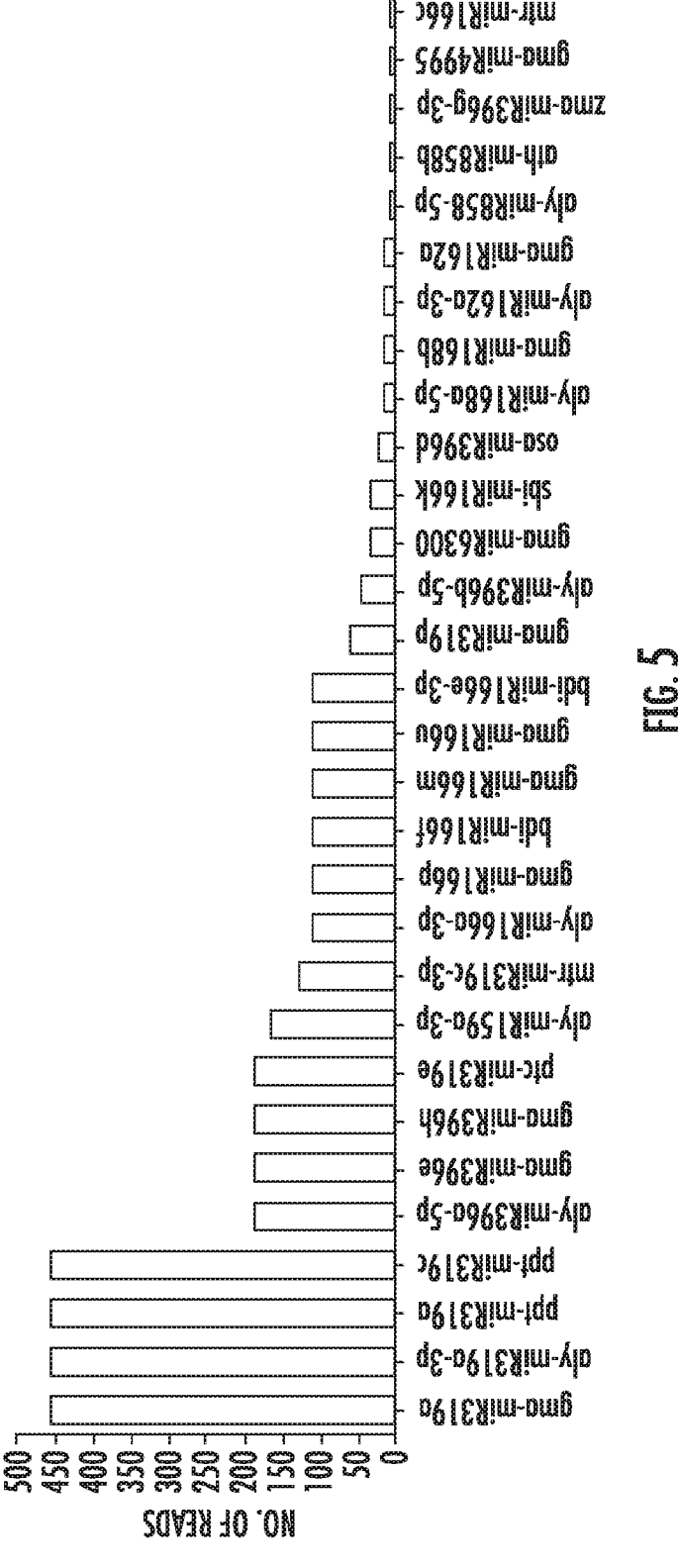

FIG. 5 is a bar graph summarizing the miRNA profile of GELNs. Total miRNA was extracted from the GELNs and the miRNA profile was determined as described herein below.

Figure 6:
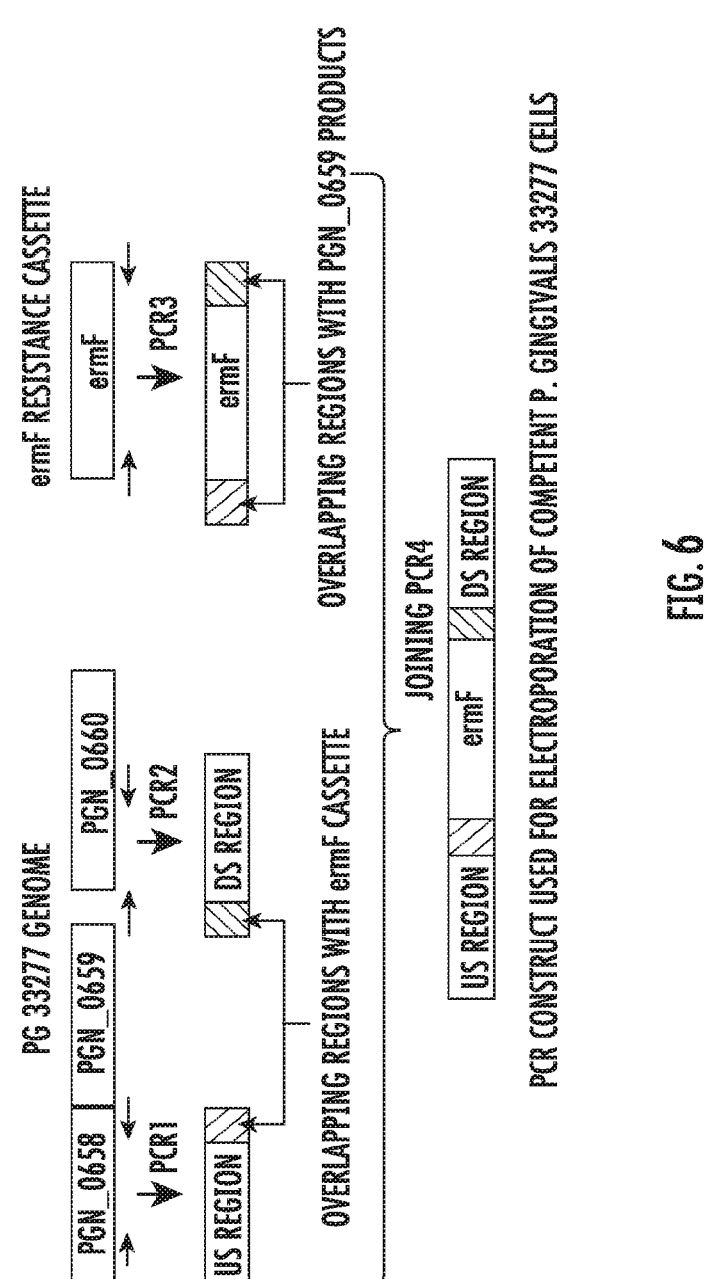

FIG. 6 is a series of schematic representations of strategies for incorporating mutations into the coding region of HBP35 of *P. gingivalis* and for confirming the same by real-time PCR.

Figure 7A:
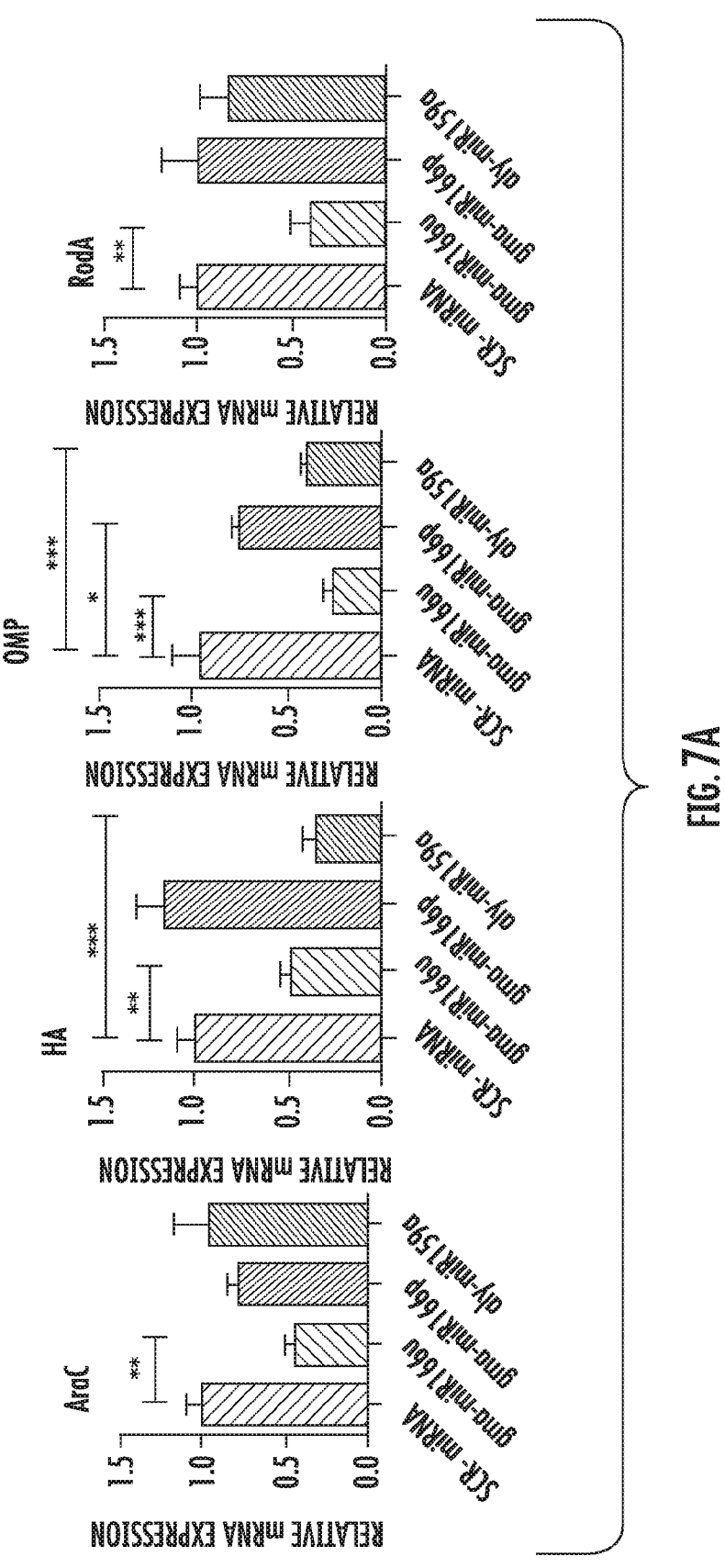
Figure 7B:
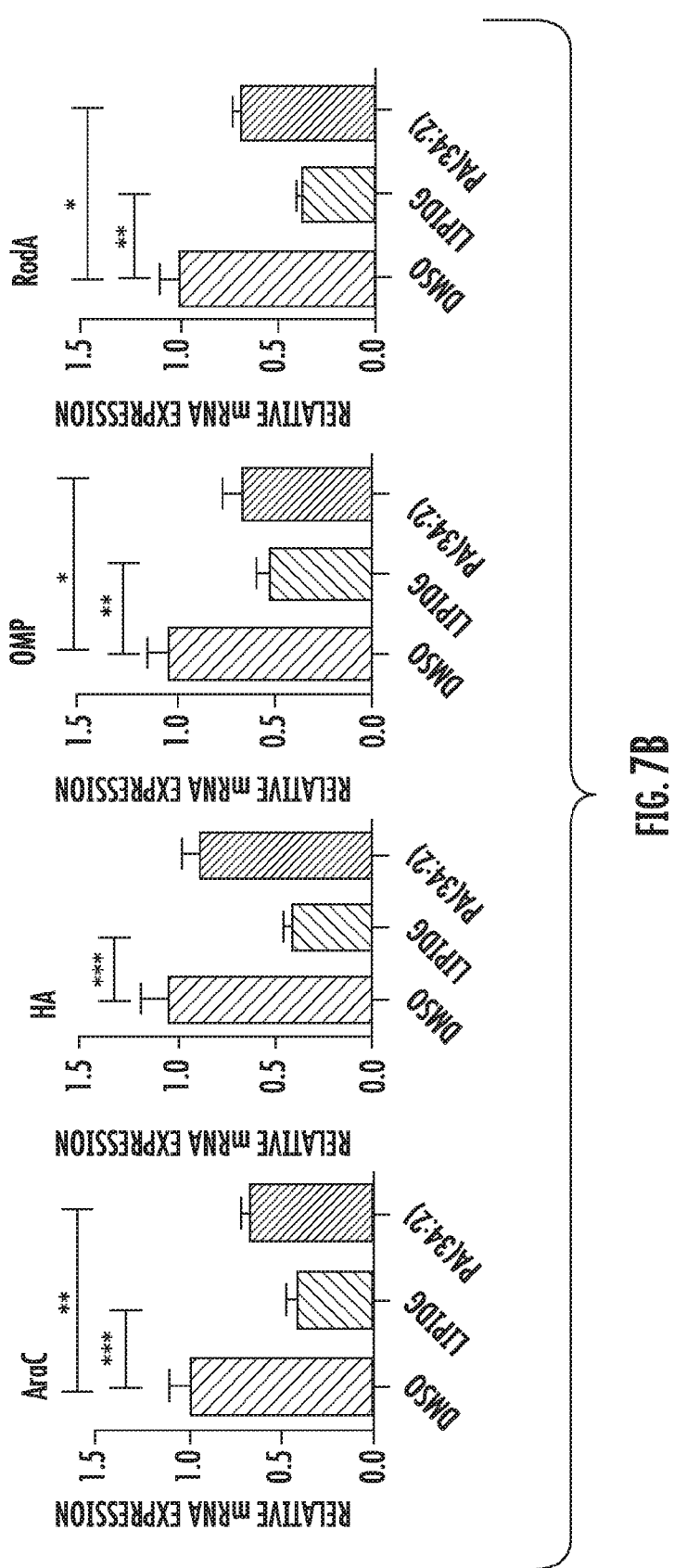

FIGS. 7A and 7B depict the result of experiments related to identification of GELNs binding protein in *P. gingivalis*. FIG. 7A is a series of bar graphs of *P. gingivalis* transduced with scrambled miRNA and aly-miR159a, gma-miR166u, and gma-miR166p for 24 hours. Total RNA isolated from these bacteria was subjected to real-time PCR analysis for AraC transcription factor, hemagglutinin (HA), outer membrane protein (OMP), and rod shape determining protein (RodA) mRNA expression. FIG. 7B is a series of bar graphs of *P. gingivalis* treated with total lipids derived from GELNs (4×$10^8$ particles) and 5 μg of PA (34:2) for 3 hours. Total RNA isolated from these bacteria was subjected to real-time PCR analysis for AraC transcription factor, hemagglutinin (HA), outer membrane protein (OMP), and rod shape determining protein (RodA) mRNA expression. The mRNA expression was normalized with 16S RNA expression. Results are expressed as means±standard deviation from three independent experiments. *p<0.05; p<0.01; *p<0.001 as compared to the untreated group using one-way ANOVA with Newman-Keuls Multiple Comparison Test.

FIGS. 8A-8H are schematic representations of GELNs miRNAs that can target various virulence genes in *P. gingivalis* at particular target sites.

Figure 9A:
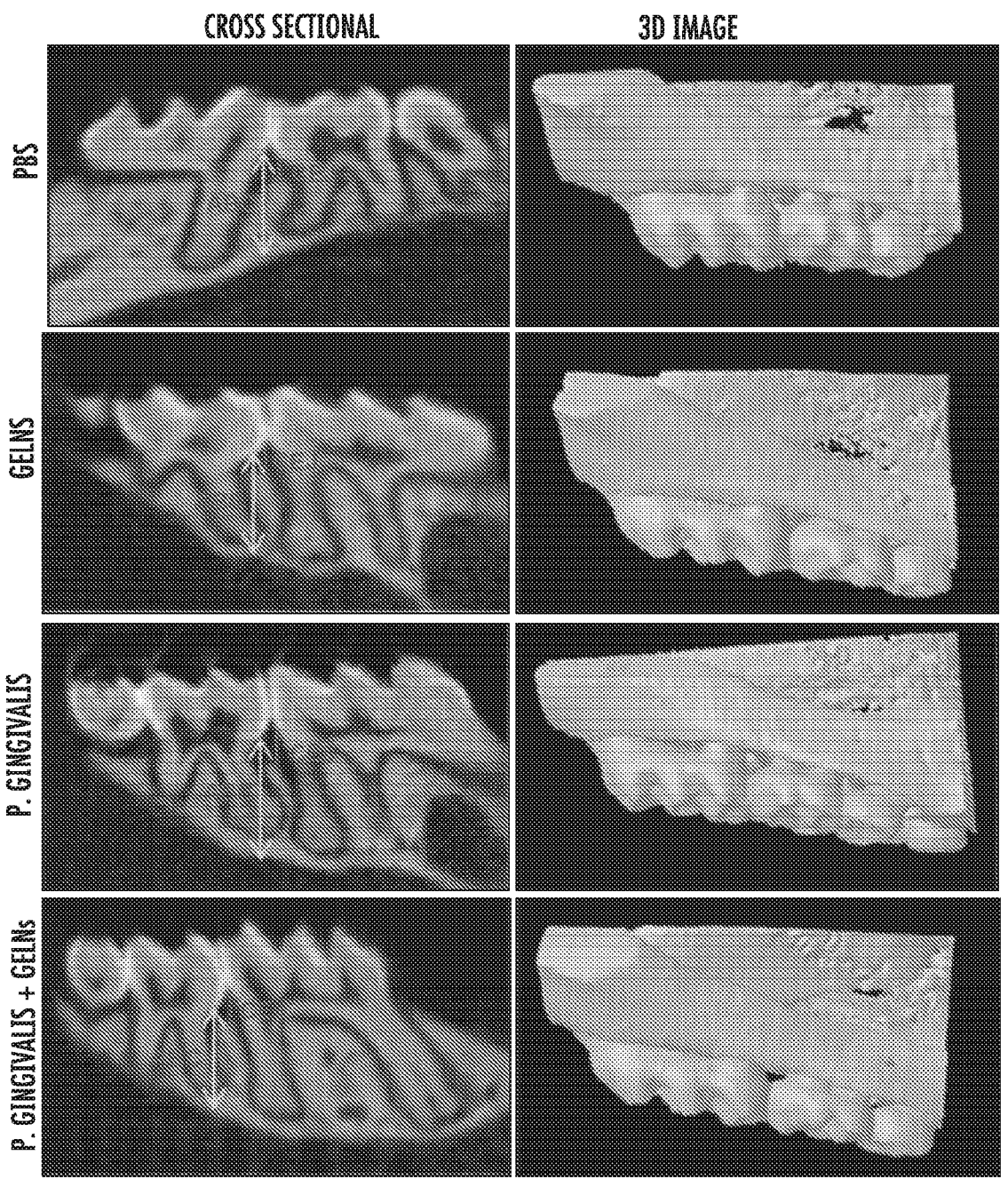
Figure 9B:
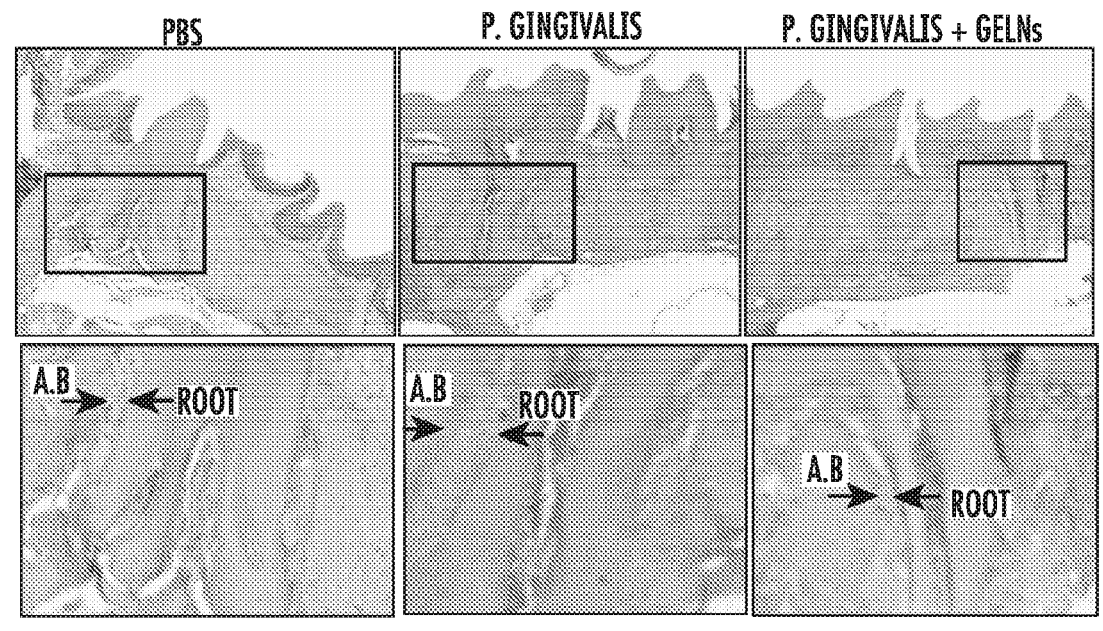
Figure 9C:
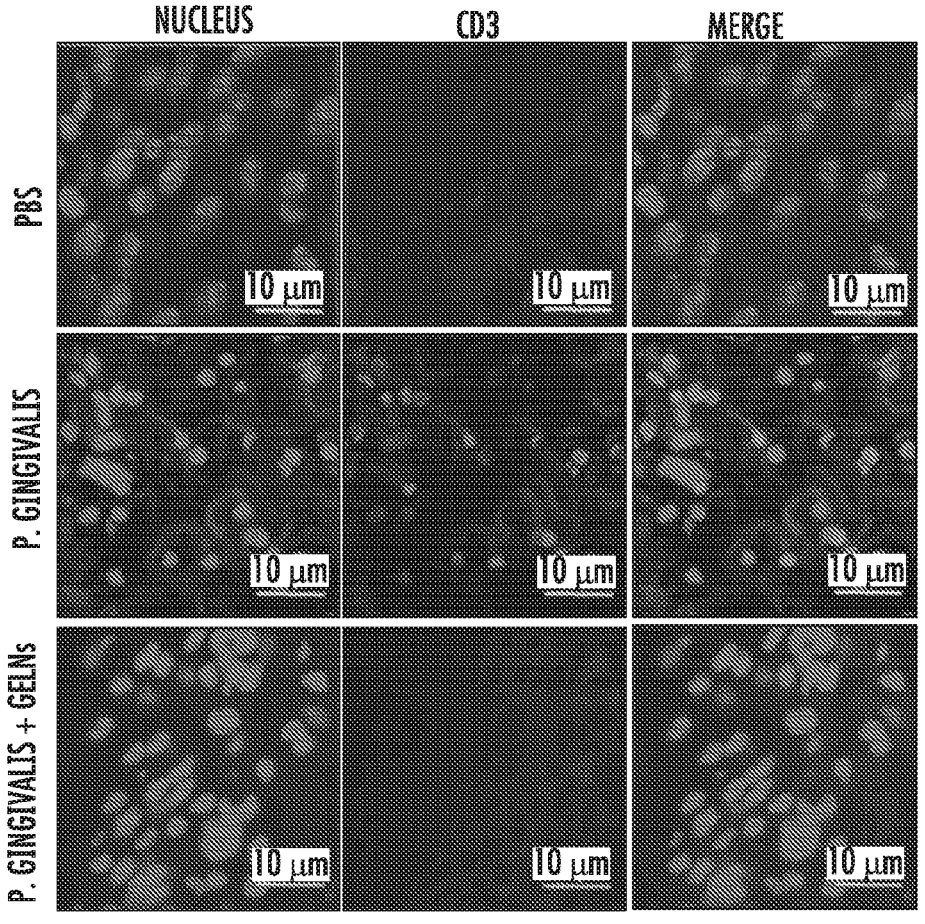
Figure 9D:
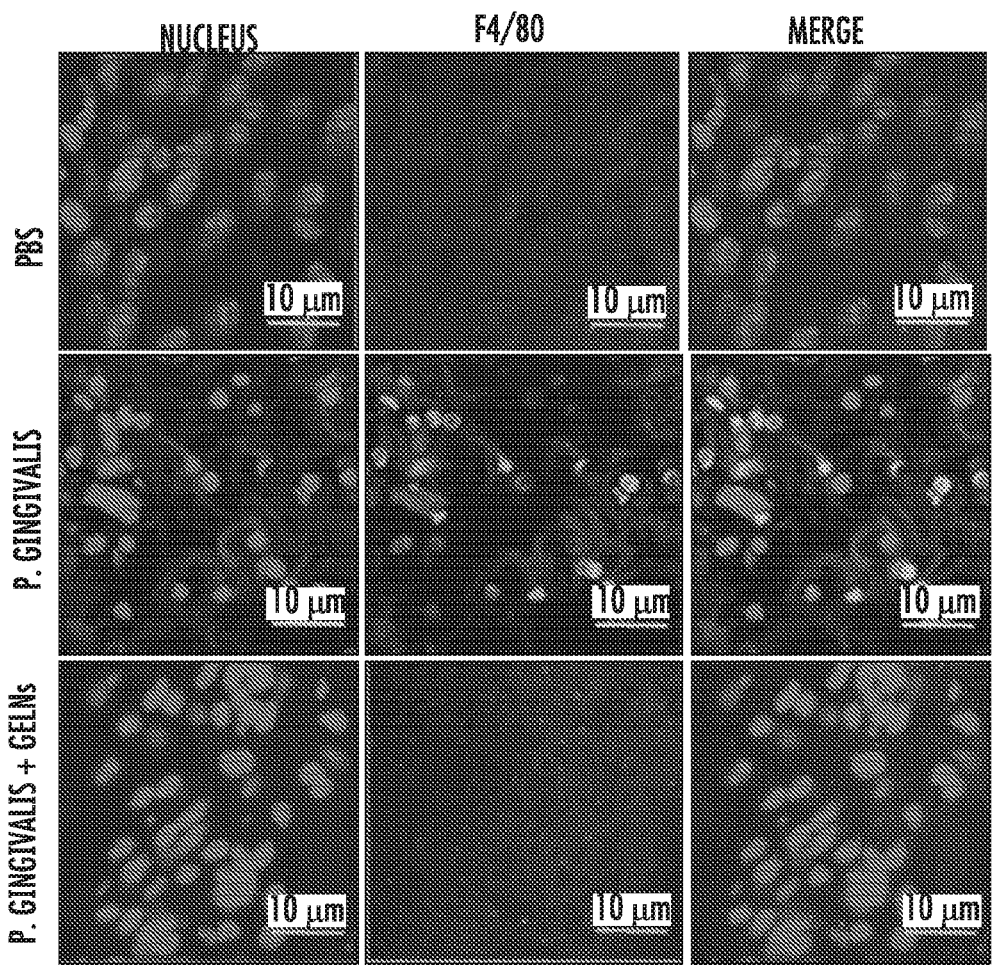

FIGS. 9A-9D depict the results of experiments showing the effects of GELNs on *P. gingivalis* induced bone loss in vivo. FIG. 9A is a series of μCT bone images of control and experimental mice represented with centennial enamel junction (CEJ) and the alveolar bone crest (ABC) with 3D image of μCT bone of control and experimental mice was constructed from scanning of each section. FIG. 9B is a series of hematoxylin and eosin stained sections from uninfected normal mice and *P. gingivalis* infected mice with and without GELNs. FIGS. 9C and 9D are a series of fluorescence micrographs of oral sections stained with anti-CD3 and anti-F4/80 antibodies with fluorescent labelled secondary antibodies. The expression of CD3 and F4/80 was visualized by confocal microscopy. Results are expressed as means±standard deviation from three independent experiments. p<0.01; *p<0.001 compared to the untreated group using one-way ANOVA with Newman-Keuls Multiple Comparison Test.

Figure 10:
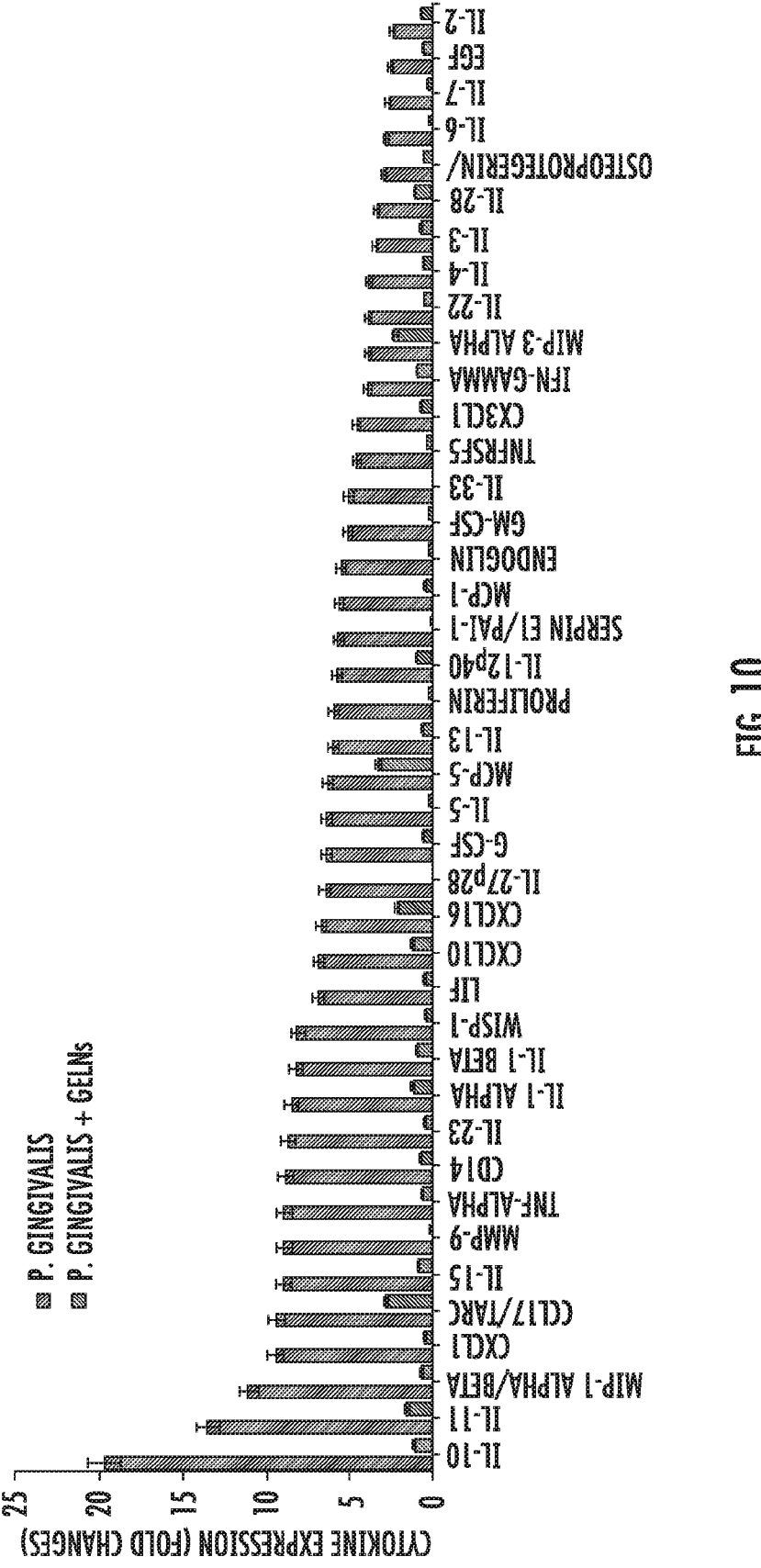

FIG. 10 is a bar graph showing that GELNs significantly decreased inflammatory and pro-inflammatory cytokine expression in *P. gingivalis*-infected mice. Cytokine expression was determined by cytokine array. Plasma was collected from control, *P. gingivalis*-infected, and *P. gingivalis*-infected and GELNs-treated mice. The cytokine levels were determined by cytokine array. Results are expressed as means±one standard deviation from three independent experiments.

DETAILED DESCRIPTION

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Furthermore, the terms first, second, third, and the like as used herein are employed for distinguishing between similar elements and not necessarily for describing a sequential or chronological order. It is to be understood that the terms so used are interchangeable under appropriate circumstances and that the subject matter described herein is capable of operation in other sequences than described or illustrated herein.

Following long-standing patent law convention, the articles "a", "an", and "the" refer to "one or more" when used in this application, including in the claims. For example, the phrase "a cell" refers to one or more cells. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, term "comprising", which is synonymous with "including," "containing", or "characterized by", is inclusive or open-ended and does not exclude additional, unrecited elements and/or method steps. "Comprising" is a term of art used in claim language which means that the named elements are present, but other elements can be added and still form a composition or method within the scope of the presently disclosed subject matter.

As used herein, the phrase "consisting of" excludes any element, step, or ingredient that is not particularly recited in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting essentially of", and "consisting of", where one of these three terms is used herein, the presently disclosed and claimed subject matter encompasses the use of either of the other two terms. For example, "comprising" is a transitional term that is broader than both "consisting essentially of" and "consisting of", and thus the term "comprising" implicitly encompasses both "consisting essentially of" and "consisting of". Likewise, the transitional phrase "consisting essentially of" is broader than "consisting of", and thus the phrase "consisting essentially of" implicitly encompasses "consisting of".

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichthyes (bony fish), Amphibia (amphibians), Reptilia (reptiles), Aves (birds), and Mammalia (mammals)), and all Orders and Families encompassed therein.

Similarly, all genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. T The methods of the presently disclosed subject matter are particularly useful for warm-blooded vertebrates. Thus, the presently disclosed subject matter concerns mammals and birds.

More particularly contemplated is the isolation, manipulation, and use of stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also contemplated is the isolation, manipulation, and use of stem cells from livestock, including but not limited to domesticated swine (pigs and hogs), ruminants, horses, poultry, and the like.

As used herein, the phrase "substantially" refers to a condition wherein in some embodiments no more than 50%, in some embodiments no more than 40%, in some embodiments no more than 30%, in some embodiments no more than 25%, in some embodiments no more than 20%, in some embodiments no more than 15%, in some embodiments no more than 10%, in some embodiments no more than 9%, in some embodiments no more than 8%, in some embodiments no more than 7%, in some embodiments no more than 6%, in some embodiments no more than 5%, in some embodiments no more than 4%, in some embodiments no more than 3%, in some embodiments no more than 2%, in some embodiments no more than 1%, and in some embodiments no more than 0% of the components of a collection of entities does not have a given characteristic.

The phrase "expression of [gene product X]" as used herein indicates that the cell expresses the gene product at a level which is sufficient for detection using standard detection methods. Expression of a marker is also referred to as "positively expressing", "+", "positive", or "pos". The terms "not expressing [marker X]" as used herein when referring to a cell indicates that the cell does not express the marker at a level which is sufficient for detection, using standard detection methods. Absence of expression of a marker is also referred to as "negative expression", "−", "negative", and "neg".

As used herein, the phrase "associated with microbial infection" refers to any symptom or consequence that occurs or can occur as a result of infection of a subject (for example, an oral infection in the subject) with a microorganism. Exemplary, non-limiting microorganisms include *Porphyromonas gingivalis* (*P. gingivalis*), *Listeria monocytogenes* (*L. monocytogenes*), and *Clostridioides difficile* (*C. difficile*). Exemplary non-limiting diseases, disorders, and/or conditions associated with microbial infection include periodontitis and alveolar bone loss.

II. Methods of the Presently Disclosed Subject Matter

In some embodiments, the presently disclosed subject matter relates to methods for preventing and/or treating an oral disease, disorder, and/or condition.

As used herein, the terms "condition", "disease condition", "disease", "disease state", and "disorder" refer to physiological states in which diseased cells or cells of interest can be targeted with the compositions of the presently disclosed subject matter. A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. In some embodiments, a disease, disorder, and/or condition is associated with a microbial infection, optionally a microbial infection of the oral cavity, although microbial infections of other cells, tissues, and organs, including but not limited to the gut, liver, and/or brain, can also be targeted with the compositions of the presently disclosed subject matter. By way of example and not limitation, a disease, disorder, and/or condition associated with a microbial infection of the oral cavity of a subject can be periodontitis, alveolar bone loss, or a combination thereof. In some embodiments, the microorganism that is associated with the disease, disorder, and/or condition is selected from the group consisting of *Porphyromonas gingivalis* (*P. gingivalis*), *Listeria monocytogenes* (*L. monocytogenes*), and *Clostridioides difficile* (*C. difficile*).

In some embodiments, the presently disclosed methods relate to preventing and/or treating an oral disease, disorder, and/or condition of the oral cavity of a subject. In some embodiments, the presently disclosed methods comprise administering to the oral cavity of a subject in need thereof a composition comprising an effective amount of ginger-derived exosome-like nanoparticles (GELNs) or a biologically active component thereof. As used herein, the phrase "ginger-derived exosome-like nanoparticles" refers to microvesicles and/or nanoparticles that can be isolated from ginger, optionally from the juice of a ginger plant, that, by the hand of man, exists apart from its native environment and is therefore not a product of nature. In this regard, in some embodiments, the phrase "ginger-derived exosome-like nanoparticles" can be used interchangeably with the phrase "nanoparticles isolated from ginger" to describe a nanoparticle of the presently disclosed subject matter that is useful in the presently disclosed methods. However, in some embodiments the phrase "ginger-derived exosome-like nanoparticle" refers to a nanoparticle that has been created from total lipids extracted from an isolated ginger-derived microvesicle and/or nanoparticle. In such embodiments, the "ginger-derived nanoparticle" is a nanoparticle that is constructed to have a particular lipid bilayer composition that is substantially similar to that of a ginger-derived nanoparticle that can be isolated from a ginger plant. As discussed in more detail here below, different edible plant-derived nanoparticles preferentially target different types of bacteria based at least in part on the types of lipids present in their bilayers. By way of example and not limitation, exosome-like nanoparticle (ELNs) derived from ginger (GELNs) have lipid bilayers that are enriched for phosphatidic acids (PAs), primarily 1,2-dilinoleoyl-sn-glycero-3-phosphate, C18:1/C18:3 (36:4), and 1-palmitoyl-2-linoleoyl-sn-glycero-3-phosphate, C16:0/C18:2 (34:2). Manufactured nanoparticles (also referred to herein as "nanovectors"; NVs) can be designed to have particular lipid bilayer compositions (including but not limited to enriched for PAs or PC) depending on which bacterial genera are of interest to target. By way of example and not limitation, if the bacteria to be targeted are *P. gingivalis*, an nanovector can be designed to have a bilayer enriched in PA since GELNs have a bilayer enriched in PA and are been shown to preferentially target *P. gingivalis*. Accordingly, the phrase "ginger-derived nanoparticle" includes both isolatable nanoparticles as well as manufactured nanoparticles.

The phrase "associated with a ginger-derived nanoparticle" or grammatical variations thereof, are used herein to refer to ginger-derived nanoparticles (e.g., isolated or manufactured) whose lipid bilayer is in contact with and/or surrounds (e.g., encapsulates) an active agent (e.g., a biologically active agent) such that isolating the GELN simultaneously results in isolation of the active agent. In some embodiments, the active component comprises a lipid, a protein, an miRNA, or any combination thereof, which in some embodiments can be a lipid, a protein, an miRNA, or any combination thereof that can be isolated (optionally together) from a ginger plant (e.g., an extract or a juice thereof). In some embodiments, wherein the GELN is a manufactured GELN, the GELN can be loaded with the active agent, which in some embodiments can be an active agent with which an isolated GELN is not normally associated. In such an embodiment, the active agent can coat the GELN (e.g., be associated with the outside of the lipid bilayer of the GELN and/or embodiments can be integrated into the lipid bilayer), can be encapsulated and/or surrounded by the lipid bilayer, or any combination thereof.

Any active agent for which delivery to a microorganism, optionally a *P. gingivalis* bacterium, further optionally a *P. gingivalis* bacterium present within the oral cavity of a subject, might be desirable can be employed in the methods of the presently disclosed subject matter. Certain active agents are naturally associated with GELNs, including lipids, proteins, and/or miRNAs as set forth herein. By way of example and not limitation, disclosed herein is evidence that certain miRNAs have antibacterial activity that can be delivered by GELNs, including but not limited to an miR-159a-3p (e.g., aly-miR-159a-3p), an miR166u (e.g., gma-miR166u), and/or an miR166p (e.g., gma-miR166p). In some embodiments, an miRNA for use in the presently disclosed subject matter is an miR-159a-3p miRNA.

As disclosed herein, the lipid composition of the GELN lipid bilayer can also be a biologically active component. As such, in some embodiments a biologically active component comprises one or more lipids, optionally wherein the one or more lipids comprises phosphatidic acid (PA). Particularly, as disclosed herein in some embodiments the one or more lipids comprises PA (34:2), which in some embodiments can interact with hemin-binding protein 35 (HBP35) on the surface of P. gingivalis to induce uptake of the GELN by the P. gingivalis. Thus, in some embodiments a GELN is modified to increase its PA content, optionally its PA (34:2) content in order to enhance the update of the GELN and any active agents that it might comprise by P. gingivalis.

Thus, in some embodiments the presently disclosed subject matter relates to methods for reducing growth of a microorganism in a subject, optionally in the oral cavity of a subject by administering to the subject, optionally to the oral cavity of the subject, a composition comprising an effective amount of ginger-derived exosome-like nanoparticles (GELNs) or a biologically active component thereof. Similarly, in some embodiments the presently disclosed subject matter relates to methods for reducing pathogenicity of a microorganism, optionally a microorganism in the oral cavity of a subject by administering to the subject, optionally to the oral cavity of the subject, a composition comprising an effective amount of ginger-derived exosome-like nanoparticles (GELNs) or a biologically active component thereof. As also disclosed herein, in some embodiments the presently disclosed subject matter relates to methods for reducing motility of a microorganism, optionally a P. gingivalis bacterium, but contacting the microorganism with a composition comprising an effective amount of ginger-derived exosome-like nanoparticles (GELNs) or a biologically active component thereof.

As such, the uptake of GELNs by microorganisms can impact (e.g., inhibit) the growth, and/or pathogenicity, and/or motility of a microorganism, and thus can be employed to treat and/or prevent diseases, disorders, and/or conditions associated with the presence of the microorganisms. A non-limiting example of a microorganism that is shown herein to be impacted by contact with GELNs is P. gingivalis, and a non-limiting example of a disease, disorder, and/or condition associated with the presence of P. gingivalis, particularly oral P. gingivalis, is periodontitis. As such, in some embodiments the presently disclosed subject matter relates to methods for preventing and/or treating periodontitis, which methods in some embodiments comprise administering to the oral cavity of a subject in need thereof a composition comprising an effective amount of ginger-derived exosome-like nanoparticles (GELNs) or a biologically active component thereof.

A second non-limiting example of a disease, disorder, and/or condition associated with the presence of P. gingivalis, particularly oral P. gingivalis, is alveolar bone loss. Accordingly, in some embodiments the presently disclosed subject matter relates to methods for reducing bone loss in the oral cavity of a subject associated with a microbial infection, optionally a P. gingivalis infection, by administering to the oral cavity of the subject a composition comprising an effective amount of ginger-derived exosome-like nanoparticles (GELNs) or a biologically active component thereof.

III. Compositions of the Presently Disclosed Subject Matter

As such, the presently disclosed subject matter also relates in some embodiments to compositions for use in the presently disclosed methods, including compositions for preventing and/or treating a disease, disorder, and/or condition, optionally an oral disease, disorder, and/or condition; and/or for preventing and/or treating periodontitis; and/or for reducing growth of a microorganism in a subject, optionally in the oral cavity of a subject; and/or for reducing pathogenicity of a microorganism in a subject, optionally the oral cavity of a subject; and/or for reducing motility of a microorganism; and/or for reducing bone loss in the oral cavity of a subject associated with infection by a microorganism. In some embodiments, the composition comprises an effective amount of ginger-derived exosome-like nanoparticles (GELNs) or a biologically active component thereof. Methods for isolating and modifying plant-derived nanoparticles such as but not limited to GELNs, including but not limited to loading and/or coating the plant-derived nanoparticles with active agents, can be found, for example, in U.S. Patent Application Publication Nos. 2012/0315324, 2014/0308212, 2017/0035700, 2018/0140654, and 2018/0362974, in PCT International Patent Application Publication No. WO 2019/104242, and in U.S. Pat. No. 9,717,733, each of which is incorporated herein by reference in its entirety.

III.A. Formulations

The compositions (e.g., GELNs) of the presently disclosed subject matter can be administered in any formulation or route that would be expected to deliver the compositions to the microorganism in whatever target site they might be present. By way of example and not limitation, if the composition is designed to treat an oral infection, the composition can formulated as a toothpaste, tooth gel, dental gel, mouth rinse, oral spray, paste, ointment, irrigant, a film, and/or as a base substance for coating toothpicks and/or dental floss. Approaches to formulating compositions in these forms can be found, for example, in U.S. Pat. Nos. 6,200,550; 8,945,518; and 10,004,676; and U.S. Patent Application Publication Nos. 2005/0036954, 2006/0034780, 2007/0066552, 2009/0026673, 2011/0038809, and 2014/0050675, each of which is incorporated herein by reference in its entirety.

In some embodiments, a composition of the presently disclosed subject matter is formulated to adhere to and/or disrupt and/or prevent formation of a biofilm. Any approach to disrupting and/or preventing formation of biofilms can be employed with the compositions of the presently disclosed subject matter, but are particularly relevant to those approaches that employ active agents that can be conjugated to, coated onto, encapsulated by, or otherwise associated with the GELNs of the presently disclosed subject matter. Exemplary such compositions include aminoglycosides, beta-lactams, cephalosporins, quinolones, macrolides, oxazolidinones, ansamycins, sulphonamides, tetracyclines, glycopeptides, sulfisoxazoles, trimethoprims, novobiocins, daptomycins, and linezolids. See e.g., U.S. Pat. Nos. 6,455,031; 6,830,745; 7,087,661; 7,314,854; 9,848,600; and 10,300,173, each of which is incorporated herein by reference in its entirety.

The compositions of the presently disclosed subject matter comprise in some embodiments a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, cytokines and other immunomodulating compounds.

III.B. Administration

Suitable methods for administration of the compositions of the presently disclosed subject matter include, but are not limited to intravenous administration and delivery directly to the target tissue or organ (e.g., the oral cavity). Exemplary routes of administration include parenteral, enteral, intravenous, intraarterial, intracardiac, intrapericardial, intraosteal, intracutaneous, subcutaneous, intradermal, subdermal, transdermal, intrathecal, intramuscular, intraperitoneal, intrasternal, parenchymatous, oral, sublingual, buccal, inhalational, and intranasal. The selection of a particular route of administration can be made based at least in part on the nature of the formulation and the ultimate target site where the compositions of the presently disclosed subject matter are desired to act. In some embodiments, the method of administration encompasses features for regionalized delivery or accumulation of the compositions at the site in need of treatment. In some embodiments, the compositions are delivered directly into the site to be treated.

III.C. Dose

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated, such as but not limited to a reduction in the growth, pathogenicity, and/or motility of a microorganism and/or a reduction in the extent to and/or timing at which a disease, disorder, and/or condition develops in a subject.). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the composition, the route of administration, combination with other drugs or treatments, the severity of the disease, disorder, and/or condition being treated, and the condition and prior medical history of the subject being treated. However, it is within the skill of the art to start doses of the compositions of the presently disclosed subject matter at levels lower than required to achieve the desired therapeutic effect and to gradually increase the dosage until the desired effect is achieved. The potency of a composition can vary, and therefore a "treatment effective amount" can vary. However, using the methods described herein, one skilled in the art can readily assess the potency and efficacy of a composition of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease, disorder, and/or condition treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the Examples

Bacterial strain and growth condition. *P. gingivalis* 33277 was cultured in tryptic soy broth supplemented with yeast extract (1 mg/ml), hemin (5 µg/ml) and menadione (1 µg/ml) and incubated at 37° C. in anaerobic chamber (85% $N_2$, 10% $H_2$, 5% $CO_2$). *S. gordonii* DL1 was cultured in brain-heart infusion broth media containing 0.5% yeast extract and incubated at anaerobically at 37° C.

Culture of TIGK cells. Human telomerase immortalized keratinocytes (TIGKs) derived from gingival epithelium were obtained from Dr. Lamont Laboratory and maintained at 37° C. and 5% $CO_2$ in DERMALIFE®-K brand serum free culture medium (Lifeline Cell Technology, Carlsbad, California, United States of America).

Isolation and purification of Ginger exosome-like nanoparticles (GELNs). Ginger exosome-like nanoparticles (GELNs) were isolated and purified as described previously. Briefly, ginger was purchased from a local supermarket and washed with sterile PBS, and the skin was peeled. The ginger was then ground in a blender to obtain the juice and strained that removed the larger particles. Juice was sequentially centrifuged at 1000 g for 10 minutes, 3000 g for 20 minutes, and 10,000 g for 40 minutes to remove large particles. Supernatant was then centrifuged at 150,000 g for 2 hours, the pellet was resuspended in sterile PBS, and transferred to a sucrose step gradient (8%/15%/30%/45%/60%) followed by centrifugation at 150,000 g for 2 hours at 4° C. The bands between the 8%/30% layer and 30%/45% layer were harvested separately and noted as ginger exosome-like nanoparticles (GELNs). The purified GELNs were fixed with 2% paraformaldehyde and imaged by electron microscopy using a Zeiss EM 900. Further, GELNs size and concentration (particle number) was determined by NanoSightNS300 (Malvern Panalytical Ltd., Malvern United Kingdom) at a flow rate of 30 µl per minute.

Bacterial growth. *P. gingivalis* or *S. gordonii* strains were cultured in the presence or absence of different concentrations of GELNs ($0-6.0 \times 10^8$ particles/ml) and total lipids derived from these particles (LipidG) for different times (0-48 hours). *P. gingivalis* and *S. gordonii* growth was determined by measuring optical density at 600 nm.

*P. gingivalis* uptake assay. Uptake of GELNs by bacteria was quantified by flow cytometry. In brief, *P. gingivalis*, *S. gordonii*, and GELNs was labelled with PKH67 (green) and PKH26 (red), respectively, according to the manufacturer's protocol (Sigma). Fluorescently-labeled *P. gingivalis* ($1 \times 10^8$) was incubated with fluorescently-labeled GELNs (0-6.0×10⁸ particles) for 1 hour at 37° C. The percentage of GELNs taken up by *P. gingivalis* and *S. gordonii* was quantified by flow cytometer.

Confocal microscopy. The interaction or uptake of GELNs by *P. gingivalis* was determined by confocal microscopy. Briefly, *P. gingivalis* and GELNs was labelled with PKH67 (green) and PKH26 (red), respectively, according to manufacturer's protocol (Sigma). Fluorescently-labeled *P. gingivalis* (1×10⁸) was incubated with fluorescently-labeled GELNs (6.0×10⁸ particles) for 1 hour at 37° C. The interaction of *P. gingivalis* and GELNs was visualized by confocal microscopy (Nikon).

*P. gingivalis* invasion. *P. gingivalis* invasion into oral epithelial cells was determined by antibiotic protection assay. *P. gingivalis* strains were grown in the TSB for 16 hours to reach mid-log phase. *P. gingivalis* was treated with or without GELNs and incubated at 37° C. for 1 hours. The bacterial cells were collected by centrifugation for 10 minutes at 5000×g and infected into TIGK cells in 24 well plates at a multiplicity of infection (MOI) of 100 at 37° C. for 1 hour. After 1 h incubation, the unbound bacteria were removed and the wells were thoroughly washed with PBS. Surface-attached external non-invaded bacteria were killed by incubation in an antibiotics cocktail of gentamycin (300 µg/ml) and metronidazole (200 µg/ml) for 4 hours. Then, the TIGK cells were washed with PBS and lysed with sterile distilled water. The invaded *P. gingivalis* were plated onto TSB blood agar plates and incubated anaerobically at 37° C. for 7 days. Colony-forming units (CFUs) were determined by counting the number of colonies on the plate. For the proliferation assay, after antibiotic treatment, TIGK cells were further incubated in an anaerobic incubator for 24 hours. Then, RNA was extracted from these cells and subjected to real time PCR for 16S rRNA expression. The number of *P. gingivalis* bacteria were calculated using a standard curve derived from known amounts of *P. gingivalis*.

Attachment to epithelial cells. The amount of *P. gingivalis* attachment to the surface of gingival epithelial cells were determined. Briefly, telomerase immortalized gingival keratinocytes (TIGKs), derived from primary gingival epithelial cell lines, were cultured in 96-well plates for 24 hours. Then, the cells were fixed with 5% buffered formalin for 1 hour, and washed with PBS. *P. gingivalis* was treated with or without GELNs (4.0×10⁸ particles) for 1 hour, the bacterial cells was collected by centrifugation for 10 minutes at 5000×g, and *P. gingivalis* strains was infected with TIGK cells at an MOI of 10 for 1 hour at 37° C. Cells were washed with PBS to remove non-adherent bacteria. Then, wells were incubated with *P. gingivalis* whole-cell antibodies (1:10,000) at 37° C. for 1 hour, then washed with PBS. Binding was detected with a secondary horse radish peroxidase (HRP)-anti-rabbit antibody (1:5,000) and 3,3',5,5'-tetramethylbenzidine substrate (Sigma), and recorded at 450 nm.

*P. gingivalis* was treated with GELNs (4.0×10⁸ particles/ml) for 1 h and the bacterial cells were collected by centrifugation for 10 minutes at 5000×g, *P. gingivalis* strains were infected with TIGK cells at an MOI of 10 for 1 hour at 37° C., and cells were washed with PBS to remove unbound bacteria to TIGK cells. Then, the TIGK cells were fixed with 5% buffered formalin for 10 minutes. *P. gingivalis* cells were stained with an antibody raised against *P. gingivalis* (1:1000 dilution) incubated for 3 hour at room temperature. After extensive washing with PBS, cells were incubated with ALEXAFLUOR® 568-conjugated IgG (1:5000 dilution) for 1 hour at room temperature. Nuclear staining was performed with DAPI for 15 minutes and localization of *P. gingivalis* was visualized by confocal microscopy (Nikon).

Gingipain proteolytic activity. The proteolytic activity of arginine-specific (Rgp) and lysine specific (Kgp) gingipain was measured. *P. gingivalis* was cultured to mid-log phase and treated with and without GELNs (2.0-4.0×10⁸ particles/ml) for 6 hour. The bacterial cells were collected by centrifugation at 5000 g for 10 minutes, washed, and lysed with BUGBUSTER® brand lysis reagent (Millipore Sigma, Burlington, MA, USA). The chromogenic p-nitroanilide substrates N-benzoyl-L-arginine-pNA or toluenesulfonyl-glycyl-prolyl-L-lysine-pNA (Sigma) were used to measure RgpA/B and Kgp respectively. Bacterial cell lysates (50 µl) were pre-incubated with assay buffer containing 200 mM Tris-HCl, 5 mM CaCl₂/150 mM NaCl and supplemented with 10 mM cysteine in 96-well plate, incubated at 37° C. for 10 minutes, and 0.5 mM of specific substrate was added to each well. The rate of substrate hydrolysis and accumulation of p-nitroanillide was monitored spectrophotometrically at 405 nm. The enzyme activity was calculated and given as mOD/min/µl.

RNA isolation and quantitative real time PCR (qRT-PCR). Total RNA was isolated from *P. gingivalis* and TIGK cells using TRIZOL™ brand reagent according to the manufacturer's protocol (Invitrogen). RNA (1 µg) was converted into cDNA with ISCRIPT™ brand cDNA synthesis kit (Bio-Rad, Hercules, California, United States of America). qRT-PCR was performed for quantification of gene expression, cDNA samples were amplified with SSOFAST™ EVAGREEN® Supermix brand qRT-PCR cocktail in CFX96 Real-time PCR system (Bio-Rad). The mRNA expression was quantified by ΔΔCt method using 16S rRNA expression as an internal control for bacterial gene expression. All primers were purchased from Eurofins MWG Operon and primers are listed in Table 1.

TABLE 1

Primers List

| Primer Name | Forward | Reverse |
|---|---|---|
| AraC | CGCGAACTCTTCTGCATCTT (SEQ ID NO: 16) | GAATACGAAGGCACGAAAGC (SEQ ID NO: 17) |
| OMP | GGATCGTTCGCTTCAGATGT (SEQ ID NO: 18) | AGCCATGATGGAAATTTTGG (SEQ ID NO: 19) |
| RodA | CGATTATAAGGGACGGATCG (SEQ ID NO: 20) | CCATCATGAAAAGGTGGGATA (SEQ ID NO: 21) |
| HA | GATCGATGCTGATGGTGATG (SEQ ID NO: 22) | CCGCTAGCAGTCCATGATTT (SEQ ID NO: 23) |
| porX | GATCGGGGACAGAAGTACCA (SEQ ID NO: 24) | ATTCGGGTAGGCGAAGAAGT (SEQ ID NO: 25) |

TABLE 1-continued

Primers List

| Primer Name | Forward | Reverse |
|---|---|---|
| porY | AGAATTGAGGATGCCGAATG (SEQ ID NO: 26) | TGCATACGAGCCTTTCTCCT (SEQ ID NO: 27) |
| porL | GGGTGCTCTCTTCAAGTTGC (SEQ ID NO: 28) | TCCATCGGATTCTTCGAGTC (SEQ ID NO: 29) |
| porM | TTCCGTCACAGCTCAATCAG (SEQ ID NO: 30) | ATTTCACGCTTACCCAAACG (SEQ ID NO: 31) |
| porN | TCGCTCGTGAACGAGTAATG (SEQ ID NO: 32) | GAATCGGGCGTAGGACAGTA (SEQ ID NO: 33) |
| porK | AGCTCAATCCGGATCAAATG (SEQ ID NO: 34) | GATGATATTGCCGCTTTCGT (SEQ ID NO: 35) |
| porW | CTCAGTCCGGACAGGAGAAG (SEQ ID NO: 36) | CTGCAGGAAATCGGCATTAT (SEQ ID NO: 37) |
| sov | AGGCGGCAGAGACTATGAAA (SEQ ID NO: 38) | CTGATAAACCTGCCCGTTGT (SEQ ID NO: 39) |
| porQ | ATGCGTTTCCTGAACTACGG (SEQ ID NO: 40) | CACCAAGGCCAAAGGAACTA (SEQ ID NO: 41) |
| porP | AGCTACTGACGGGCACAGTT (SEQ ID NO: 42) | AAAGCATAGCCGGCATAGAA (SEQ ID NO: 43) |
| porT | GGTCTCGGATGCGATTTTTA (SEQ ID NO: 44) | CTCGAAATTGAACGTGAGCA (SEQ ID NO: 45) |
| porV | CTCTGTGCCATCGCTGAATA (SEQ ID NO: 46) | AGAAACCGGTCATCTGCATC (SEQ ID NO: 47) |
| OMPA2 | CATTGACATTGCAGGTGGAG (SEQ ID NO: 48) | TCGAACATGAAGTCGAGGTG (SEQ ID NO: 49) |
| fimA | TTGTTGGGACTTGCTGCTCTTG (SEQ ID NO: 50) | TTCGGCTGATTTGATGGCTTCC (SEQ ID NO: 51) |
| 16S rRNA | AGGAACTCCGATTGCGAAGG (SEQ ID NO: 14) | TCGGTTTACTGCGTGGACTACC (SEQ ID NO. 15) |
| IL-1β | GTTCCCATTAGACAACTGC (SEQ ID NO: 52) | GATTCTTTCCTTTGAGGC (SEQ ID NO: 53) |
| IL-6 | GATACCACTCCCAACAGACC (SEQ ID NO: 54) | GCAATGGCAATTCTGATTGT (SEQ ID NO: 55) |
| TNF-α | TCTATGGCCCAGACCCTCAC (SEQ ID NO: 56) | GACGGCAGAGAGGAGGTTGA (SEQ ID NO: 57) |
| GAPDH | AGGTCATCCCAGAGCTGAACG (SEQ ID NO: 58) | ACCCTGTTGCTGTAGCCGTAT (SEQ ID NO: 59) |

Western blot. *P. gingivalis* was incubated anaerobically with PBS or GELNs (0-4.0×10¹ particles/ml) at 37° C. for 6 h. Total cell lysates were prepared in BUGBUSTER® brand lysis reagent with protease and phosphatase inhibitors (Roche). Cell lysates were separated by SDS-PAGE (4-15% gradient gel) and transferred onto nitrocellulose membrane. After transfer, the membrane was probed with primary polyclonal antibodies specific for fimA, Mfa1 at a dilution of 1:1000 with PBST (PBS+100 v/v Tween-20) for 1 hour at room temperature. The primary antibodies were obtained from Dr. Richard J. Lamont's laboratory at the University of Louisville (Louisville, Kentucky, United States of America). Then, the membrane was incubated with secondary antibodies conjugated to ALEXAFLUOR®-647 (Eugene, OR, USA) at a dilution of 1:10,000 for 1 hour at room temperature. The band was visualized and band intensity was analyzed on an Odyssey Imager (LiCor Inc, Lincoln, Nebraska, United States of America).

Lipid extraction and TLC analysis. Total lipids from ginger exosome-like nanoparticles (GELNs) were extracted with chloroform:methanol (2:1, v/v). Thin layer chromatography (TLC) was performed. Briefly, high-performance thin-layer chromatography (HPTLC) plates (silica gel 60 with concentrating zone, 20 cm×10 cm; Merck) were used for the separation. Aliquots of concentrated lipid samples extracted from GELNs were separated on HPTLC-plates, and the plates developed with chloroform/methanol/acetic acid (190:9:1, by vol). After drying, lipids were stained with iodine vapor. The plate was imaged with an Odyssey Scanner (LI-COR Bioscience, Lincoln NE).

Lipidomic analysis. Lipid samples extracted from GELNs were submitted to the Lipidomics Research Center, Kansas State University (Manhattan, Kansas, United States of America) for analysis. Briefly, lipid compositions were determined using a triple quadrupole mass spectrometer (an Applied Biosystems Q-TRAP, Applied Biosystems, Foster City, CA, United States of America). The data are reported as concentration (nmol/mg GELNs) and percentage of each lipid in total signal for the molecular species determined after normalization of the signals to internal standards of the same lipid class.

Preparation of GELN RNA Libraries and sequencing. Small RNA libraries were generated with 100 ng of total RNA from GELNs and TRUSEQ® brand Small RNA Library Preparation Kits (Illumina) according to the manufacturer's instructions. Following PCR amplification (16 cycles), libraries between 140 and 160 basepairs (bp) in size were gel-purified and resuspended in ultrapure water (11 µl). Equal amounts of libraries were pooled and sequenced on the Illumina HiSeq 2500, followed by demultiplexing and FASTQ generation with CASAVA v1.8.4. Raw FASTQs were adapter and quality score trimmed with cutadapt v1.10 (Martin, 2011) with a minimum length of 15 nucleotides. MicroRNAs were identified using the sRNABench Pipeline (version May 14; Barturen et al., 2014). A core set of plant miRNAs from miRBase v21 were used as reference, and this set included all 14 plant species with at least 200 mature microRNA sequences annotated in miRBase. Within the sRNABench Pipeline, mapping was performed with bowtie (v0.12.9) and microRNA folding was predicted with RNAfold from the Vienna package (v2.1.6).

Delivery of miRNA into *P. gingivalis*. GELNs miRNAs such as aly-miR-159a-3p, gma-miR166u, gma-miR166p, and gma-miR319a were packaged into lemon-derived liposomes as described. Briefly, total lipids were extracted from lemon-derived exosome-like nanoparticles. 20 nM of miRNA was added into 100 nM of lemon lipids in 0.9% NaCl and presence of PEI (2 μg/ml), this mixture was sonicated in water bath to make liposome-miRNA complex, and centrifuged at 36,000 rpm for 1 hour. The unbound RNA content in the supernatant was measured. The RNA bound liposomes were treated with *P. gingivalis* for 24 hours and total RNA isolated was subjected to quantitative real-time PCR analysis.

Metabolomics. *P. gingivalis* were incubated anaerobically with PBS in the presence and absence of GELNs ($4.0 \times 10^8$ particles/ml) for 24 hours. Bacterial media was collected by centrifugation and filter through 0.22 micron filter to remove all bacterial debris. Then, the media was freeze-dried and dissolved in 100 μl of acetonitrile (20%) and further centrifuged (14000 rpm) for 10 minutes at 4° C. Transfer supernatant into LC vials for LC-MS/MS analysis for bacterial metabolites. Briefly, the supernatant was injected into a SEQUANT® ZIC®-cHILIC brand hydrophilic interaction liquid chromatography (HILIC) column (150×2.1 mm i.d., 3 μm, and catalog number 150658; MilliporeSigma, St. Louis, Missouri, United States of America). The mobile phase A contained 10 mM ammonium acetate (pH 3.25) and mobile phase B contained acetonitrile with 0.1% formic acid at flow rate of 0.3 mL/min. The column effluent was introduced into the mass spectrophotometer (Thermo Q EXACTIVE™ HF HYBRID QUADRUPOLE ORBITRAP™, Thermo Fisher Scientific, Inc., Germany) using ESI operating in negative and positive ion mode.

Transmission Electron Microscopy. *P. gingivalis* and *S. gordonii* were treated with PBS and GELNs ($6.0 \times 10^8$ particles/ml) for 3 hours. Bacterial cells were collected by centrifugation (5000 g, 10 minutes) and resuspended in 10 mM Tris (pH7.8) and fixed with 2% formaldehyde and 1% glutaraldehyde. The bacterial suspension (20 μl) were applied to a formvar-coated copper grid (200 mesh, Electron Microscopy Science, PA, USA) and air dried and negatively stained with 0.5% ammonium molybdate. Bacterial morphology was observed under transmission electron microscope (Thermo-Fisher TEM Tecnai Spirit) at 80 kV, and images were collected with an AMT XR60 digital camera.

Outer membrane permeability assay (EtBr influx assay). *P. gingivalis* outer membrane permeability was measured. *P. gingivalis* was grown to mid-log phase and washed with binding buffer (25 mM MES pH 6.0, 25 mM NaCl). *P. gingivalis* was treated with GELNs ($0$–$6.0 \times 10^8$ particles/ml) for 2 hours at 37° C. and add ethidium bromide (0.5 μM). The fluorescence of Et-Br-nucleic acid complex was immediately measured by fluorescence spectrophotometer (Molecular Device) with excitation and emission wavelength of 545 and 600 nm respectively. The widths of the slits are 5 and 10 nm, respectively.

Cytoplasmic membrane integrity assay. The cytoplasmic membrane depolarization of *P. gingivalis* was measured by using membrane potential sensitive fluorescent dye $diSC_3$-5. Briefly, mid-logarithmic phase *P. gingivalis* were washed with 5 mM sodium HEPES buffer, pH 7.4, containing 20 mM glucose, and resuspended to an $OD_{600}$ of 0.05 in the same buffer. The cell suspension was incubated with 0.4 μM $diSC_3$ until a stable reduction of fluorescence was achieved. KCl was added to a final concentration of 0.1 M to equilibrate the cytoplasmic and external $K^+$ concentration. *P. gingivalis* was treated with GELNs ($6.0 \times 10^8$ particles/ml) for 2 hours for at 37° C. Changes in fluorescence were recorded using an F-4500 fluorescence spectrophotometer (Hitachi, Japan) with an excitation wavelength of 622 nm and an emission wavelength of 670 nm.

Liposome preparation. Total lipids from ginger exosome-like nanoparticles (GELNs) were extracted with chloroform: methanol (2:1, v/v). Thin layer chromatography (TLC) was performed with standard PA(34:2). The corresponding PA band was excised from the TLC plate and remaining bands were pool together. GELNs total lipids, PA depleted lipids and PA(34:2) were completely dried under stream of nitrogen gas. The lipid film was suspended in HEPES-buffered saline (HBS) running buffer (20 mM HEPES, 150 mM NaCl, pH 7.4) and gently vortexed and sonicated for 10 minutes until clear solution was formed. The liposome suspension was extruded through a poly carbonated membrane filter syringe with pore size of 100 nm. The size of liposome was confirmed by NanoSight NS300 (Malvern Panalytical Inc, MA, USA). Total lipids were determined by measuring total phosphate levels.

Surface Plasmon Resonance (SPR). SPR experiments were conducted on an OPENSPR™ (Nicoya, Lifesciences, ON, CA). All experiments were carried on LIP-1 sensor (Nicoya, Lifesciences). Tests were run at flow rate of 20 μl/minute using HBS running buffer (20 mM HEPES, 150 mM NaCl, pH 7.4). First, LIP-1 sensor chip was cleaned with Octyl 0-D-glucopyranoside (40 mM) and CHAPS (20 mM). Liposomes (1 mg/ml) were injected on the sensor chip for 10 minutes until stable resonance was obtained. After immobilization of liposomes, the surface was blocked with BSA (3%) in running buffer was used a blocking agent to prevent non-specific binding of protein on chip surface. After stable signal was obtained, *P. gingivalis* total cell lysates (5 μg/ml of protein concentration) were run over the immobilized liposomes. A negative control test was also performed by injecting protein onto a blank sensor chip to check for non-specific binding. After 10 minutes running of running buffer, the liposome binding protein was eluted using NaOH (200 μM). The eluted protein was subjected to LC-MS proteomics analysis for identification of GELNs liposome and PA binding protein. The sensograms were analyzed using TRACEDRAWER™ brand kinetic Analysis software.

Proteomic sample preparation. GELNs binding protein in *P. gingivalis* was identified by LC-MS proteomics method. Briefly, GELNs was labelled with biotin using EZ-LINK™ Sulfo-NHS-Biotinylation Kit according to the manufacturer's protocol (Thermo Fisher Scientific, San Jose, CA, USA). The biotin labelled GELNs was incubated with *P. gingivalis* for 1 hour at room temperature with rotation. The biotin was pull down by streptavidin magnetic beads (Thermo Fisher Scientific, San Jose, CA, USA) and beads were washed thoroughly with PBS to remove unbound protein. The protein bound magnetic beads were suspended in lysis buffer (2% SDS, 100 mM DTT, 20 mM Tris-HCl pH 8.8) at 95° C. for 20 minutes. Protein was collected from supernatants after centrifugation and concentrations were estimated using a Protein Assay Kit (Bio-Rad, Hercules, CA, USA). Protein aliquots (50 mg) were diluted into 4% SDS/0.1 M Tris-HCl pH 8.5 and 1 M DTT and were processed according to the filter-aided sample preparation (FASP) method. The digested, ultra-filtered samples were trap-cleaned with C18 PROTO™, 300 Å Ultra MicroSpin columns, lyophilized by vacuum centrifugation, and re-dissolved into 16 μl of 2% v/v acetonitrile and concentrations estimated based on absorption at 205 nm using a Nanodrop 2000 (Thermo Fisher Scientific, San Jose, CA, USA).

Liquid chromatography-mass spectrometry (LC-MS) data analysis. LC/MS was carried out. Proteome Discoverer v1.4.1.114 (Thermo Fisher Scientific, San Jose, CA, USA) was used to analyze the data collected by the mass spectrometer. The database used in Mascot v2.5.1 and SequestHT searches was the Feb. 17, 2017 version of the *P. gingivalis* proteome from UniprotKB (Proteome ID UP000236566; Acuna-Amador et al., 2018). Scaffold was used to calculate the false discovery rate using the Peptide and Protein Prophet algorithms. Proteins were grouped to satisfy the parsimony principle. The proteins were clustered based on differential expression and heat maps representing differentially regulated proteins by GELNs were generated using software R.

Construction of mutant HBP35 in *P. gingivalis*. The mutation in HBP35 (PGN_0659; see also GENBANK® Accession No. WP_004565167.1, encoded by nucleotides 716804-717838 of GENBANK® Accession No. NC_010729) was obtained by allelic replacement and the mutant allele was constructed a PCR fusion technique with the primers described. Briefly, DNA sequences 999 bp upstream of the PGN_0659 ATG initiation codon and 930 bp downstream of the PGN_0659 TGA stop codon were amplified using the 0659usF (GATGAGCCGACGAT-GAGTATGC; SEQ ID NO: 2), 0659usR (GAAGCTAT CGGGGGTACCTTGCAAATACTTTGCCTCTGT-TATCGTC; SEQ ID NO: 3), and 0659dsF (TGTCCCT-GAAAAATTTCATCCTATTGAGCTAAGATT-TAAACGAAAACTGCG; SEQ ID NO: 4), and 0659dsR (AATGCTCGGTTTCAGTGTCTGC; SEQ ID NO: 5) primers, respectively, using *P. gingivalis* 33277 genomic DNA. To replace the PGN_0659 gene, an ermF cassette was amplified from *P. gingivalis* 33277Δltp1 using the ermF (GGTTACCCCCGATAGCTTCC; SEQ ID NO: 6) and ermR (GGATGAAATTTTT CAGGGACA; SEQ ID NO: 7) primers that contained 5' homology with the 0659usR and 0659dsF primers. The final PCR fusion product was purified using the New England Biolabs Monarch PCR and DNA cleanup kit. The amplicon was directly electroporated into *P. gingivalis* 33277. Recombinants were selected for using TSB blood agar plates supplemented with yeast extract, hemin, menadione and erythromycin (10 ug/mL). Replacement of PGN_0659 is confirmed by real-time PCR using following primers: 0659-F (TACTCTCTGCTGC-TATCCTAAGT; SEQ ID NO: 8) and 0659-R (CCTCC AACACCACATTCTTCT; SEQ ID NO: 9); 0658-F (GCTTCCGGTAGCGATGATAA; SEQ ID NO: 10) and 0658-R (CACCTCCACATACTCGTCATAC; SEQ ID NO: 11); 0660-F (TGGCTTATCGTGGCTCTTTC; SEQ ID NO: 12) and 0660-R (GGAGGATCT CTTCTGCATCAC; SEQ ID NO: 13).

Gliding motility. Gliding motility of *P. gingivalis* was measured. *P. gingivalis* was reacted with GELNs ($4 \times 10^8$ particles/ml) or total lipids extracted from GELNs or miRNAs such as aly-miR-159a-3p, gma-miR166u, and gma-miR166p. A sterile "U" shaped glass tube containing 0.2% agar as suspension medium was produced. *P. gingivalis* (100 μl) was inoculated one edge of the tube and incubated at anaerobic chamber for 48 hours, the location of bacteria was visualized by cloudiness, and distance movement of *P. gingivalis* was calculated.

Animal infection. Female 10-12-week-old C57BL/6 mice were obtained from Jackson Laboratories and employed for oral inoculation of *P. gingivalis*. Mice were maintained in groups and housed in micro isolator cages. Mice were fed standard diet with water ad libitum and kept in 12 hour periods of light and dark cycle. The University of Louisville Institutional Animal Care and Use Committee approved all animal procedures in this study. Before oral inoculation, *P. gingivalis* ($10^8$) strain was reacted with GELNs ($4.0 \times 10^8$ particles) at 37° C. for 1 hour and centrifuged at 5000 g for 10 minutes. There was no difference in viability of *P. gingivalis* in this time point of GELNs (Laboratory observations). *P. gingivalis* was suspended in 1 ml of 2% carboxymethylcellulose (CMC) at two-day intervals over ten days periods. Mice were given GELNs ($4.0 \times 10^8$ particles/ml) ad libitum in drinking water until mice were sacrificed. To enumerate the colonization of *P. gingivalis*, oral samples were collected along the gingiva of the upper molars using a 15-cm sterile polyester-tipped applicator at one, two, and three weeks after the final bacterial infection. Total genomic DNA was isolated from these samples using a QIAamp DNA isolation kit (Qiagen) and amplified by qPCR with primers to 16s rRNA Forward (5'-AGGAACTCCGAT-TGCGAAGG-3'; SEQ ID NO: 14) and reverse (5'-TCGTT-TACTGCGTGGACTACC-3; SEQ ID NO: 15). Number of *P. gingivalis* were calculated using standard curve derived from known amount of *P. gingivalis*. Forty-two days after the last infection, mice were euthanized, and skulls were subjected to μCT scan (SKY SCAN, Bruker). Bone loss was assessed by measuring the distance between the alveolar bone crest and the cementoenamel junction at 14 predetermined points on the maxillary molars.

Histology and immunofluorescence staining. Oral tissue specimens were decalcified with 0.5 M EDTA (pH 7.4) for 3-4 weeks and processed for paraffin embedding. Tissue samples were cut at 5 μm thickness and stained with hematoxylin and eosin. For immunofluorescence analysis, tissue sections were subjected to antigen retrieval by boiling the slides in antigen unmasking solution (Vector laboratories) for 10 minutes according to manufacturer's instructions. The section was blocked with blocking buffer (5% BSA in PBS) for 1 hour at room temperature and incubated with primary antibodies (1:100 dilution) anti-rabbit-CD3 and F4/80 at 4° C. overnight. After extensive washing with PBS, tissue sections were incubated with ALEXAFLUOR® 568-conjugated IgG and ALEXAFLUOR® 488-conjugated IgG (1:5000 dilution) for 1 hour at room temperature. Nuclear staining was performed with DAPI for 15 minutes and images were captured on confocal microscopy (Nikon) Statistical analysis. Values are shown as mean±SD for three independent experiments.

Statistical analysis was performed with GraphPad Prism 6. Comparison of multiple experimental groups was performed by one-way Analysis of Variance test. A t-test was used to compare the means of two groups. p values of <0.05 were considered to be statistically significant. Sample sizes are calculated to allow significance to be reached.

Example 1

GELNs are Selectively Taken Up by Pathogenic *P. gingivalis, Leading to Inhibition of P. gingivalis* Growth It is well known that a healthy diet can prevent chronic periodontitis. GELNs are also know to have anti-inflammatory effects via interaction with host hepatocytes and GELNs miRNAs selectively promote beneficial intestinal bacterial growth. Whether GELNs have direct effect on the pathogenic bacteria like *P. gingivalis* is not known.

To test whether GELNs have direct effect on the *P. gingivalis*, pathogenic *P. gingivalis* and non-pathogenic *S. gordonii* were incubated with different concentration (0-6.0× $10^8$ particles/ml) of PKH26-labelled GELNs for 1 hour. FACS analysis indicated that the GELNs were selectively taken up by *P. gingivalis* in a dose-dependent manner, whereas *S. gordonii* uptake of GELNs was negligible. *P. gingivalis* up take of GELNs was further confirmed by confocal microscope.

Uptake of GELNs led to inhibiting the growth of *P. gingivalis* as dose and time dependent manner (see FIGS. 1A and 1B). At higher dose (6×$10^8$ GELNs particles/ml), no growth of *P. gingivalis* was observed. Electron microscopy further indicated that treatment with GELNs at a dose of 6×10 GELNs particles/ml resulted in morphological changes to *P. gingivalis* but not to *S. gordonii* (see FIG. 1C). However, GELNs were not taken up by the non-pathogenic bacteria *S. gordonii*, and GELNs did not inhibit the growth of *S. gordonii*.

Membrane depolarization has a profound impact on bacterial viability and signal transduction. The effects of increased the depolarization of *P. gingivalis*. In contrast, GELNs did not affect the cytoplasmic membrane depolarization of *S. gordonii*.

In addition, *P. gingivalis* outer membrane barrier function was measured by an ethidium bromide (EtBr) influx assay. The results showed that GELNs significantly increased fluorescence intensity at dose dependent manner (see FIG. 2A). Furthermore, supernatants were collected from *P. gingivalis* and *S. gordonii* treated with or without GELNs and subjected to SDS-PAGE electrophoresis. The results revealed that high level of proteins were released into media in GELNs treated *P. gingivalis* but not in *S. gordonii* (see FIG. 2B), indicating that GELNs interacted with bacterial membrane which leads to releasing cytoplasmic proteins into the culture media.

Metabolic products released from the *P. gingivalis* treated with GELNs were also determined (see FIGS. 3A and 3B) and the role of the identified metabolic product are listed in (Table 2). Collectively, these results indicated that GELNs were selectively taken up by the pathogenic bacterium *P. gingivalis* but not by the non-pathogenic bacterium *S. gordonii*, leading to the inhibition of the growth of *P. gingivalis*.

TABLE 2

| *P. ginigvalis* Released Metabolites Function | |
| --- | --- |
| Metabolites | Function |
| Lysine | lysine, is required in protein synthesis and is also used in the peptidoglycan layer of Gram-positive bacterial cell walls |
| Tyrosine | D-tyrosine has potent activity toward biofilm disassembly |
| Proline | Protection against abiotic stress, osmoregulation, protein stability, involved in cell signaling and energy production |
| Ornithine | contribute to cytosolic pH homeostasis when cells are exposed to acidic environments |
| L-methionine sulfoxide | Defends against oxidative stress |
| L-Carnitine | Role in electron transport chain, osmoprotection, served as nutrient |
| Dihydrothymine | DNA damage product which Impairs the Base Excision Repair Pathway |
| L-pipecolic acid | served as carbon and nitrogen source |
| Pyridoxamine | Served as cofactor of enzymes, role in amino acid and fatty acid metabolism |
| Dimethyl-L-arginine | involved in several metabolic pathway and role in bacterial pathogenesis |
| Methionine | initiation of translation, it is common cofactor |
| Phenylalanine | Degradation by several anaerobic bacteria and important for growth |
| 3-Methylcrotonglycine | Modulates mitochondrial energy production and inhibit ATPase |
| 2'-Methyladenosine | Involved in gene regulation |
| Threonine | Phosphorylation of protein which play an important role in pathogenesis, host cell interaction |
| Glycine | inhibit bacterial growth, inhibit synthesis peptidoglycan on bacterial cell wall |
| Isoleucine | Role in bacterial growth |
| Tetramethylpyrazine | Bacteria used for carbon and energy source |
| 5-Aminovaleric acid | Bacterial catabolic product of Lysine and play a role in biotransformation |
| Cystathionine | Metabolites used for methionine biosynthesis |
| 4-Indoleccarbaldehyde | Biofilm formation, virulence factor production, antibiotic resistance. |
| Choline | It is precursor to GB, and GB act as a potent osmoprotectant and roles in shaping microbial communities |
| Citruline | Protects bacteria from acid stress |
| Histidine | Used as a source of carbon, energy, and nitrogen |
| Asparagine | Important role in glycoprotein biosynthesis |
| Guanine | Bacterial genomic DNA |
| Adenine | Adenine Methylation play a role in Regulating Bacterial Gene Expression and Virulence |

GELNs on membrane depolarization of *P. gingivalis* and *S. gordonii* were measured, and cytoplasmic membrane depolarizations were determined using the membrane potential sensitive dye diSC₃. The results showed that the GELNs Edible plant exosomes including GELNs consist of a number of proteins, lipids, and RNAs, including miRNAs. Therefore, which GELNs-derived factor(s) specifically inhibited *P. gingivalis* growth was determined. *P. gingivalis* was treated with different concentration of total lipids derived from GELNs (LipidG); 0-5.0×10⁸ particles/ml) for 24 hours and the growth of *P. gingivalis* was measured by GD at 600 nm. GELNs lipids significantly decreased *P. gingivalis* growth in a dose-dependent manner (see FIG. 4A). RNA sequencing analysis of GELNs RNA showed that miRNAs were enriched in GELNs (see FIG. 5).

Target sequencing analysis indicated that these GELNs miRNAs have potential target sequences in a variety of genes in *P. gingivalis* (summarized in Table 3; see also FIGS.

8A-8H). Based on the target genes in *P. gingivalis*, miRNAs aly-miR159a-3p, gma-miR166u, and gma-miR166p were selected for further study to determine whether these miRNAs might play a role in inhibition of *P. gingivalis* growth. *P. gingivalis* was transduced with GELN-derived miRNAs and growth of *P. gingivalis* was measured. The results showed that these miRNAs did not affect the growth of *P. gingivalis*. Based on these results, that GELN lipid played a critical role in inhibition of *P. gingivalis* was confirmed.

TABLE 3

GELN-derived miRNAs Targeting *P. gingivalis* Genes

Figures 8F, 8G, 8H:
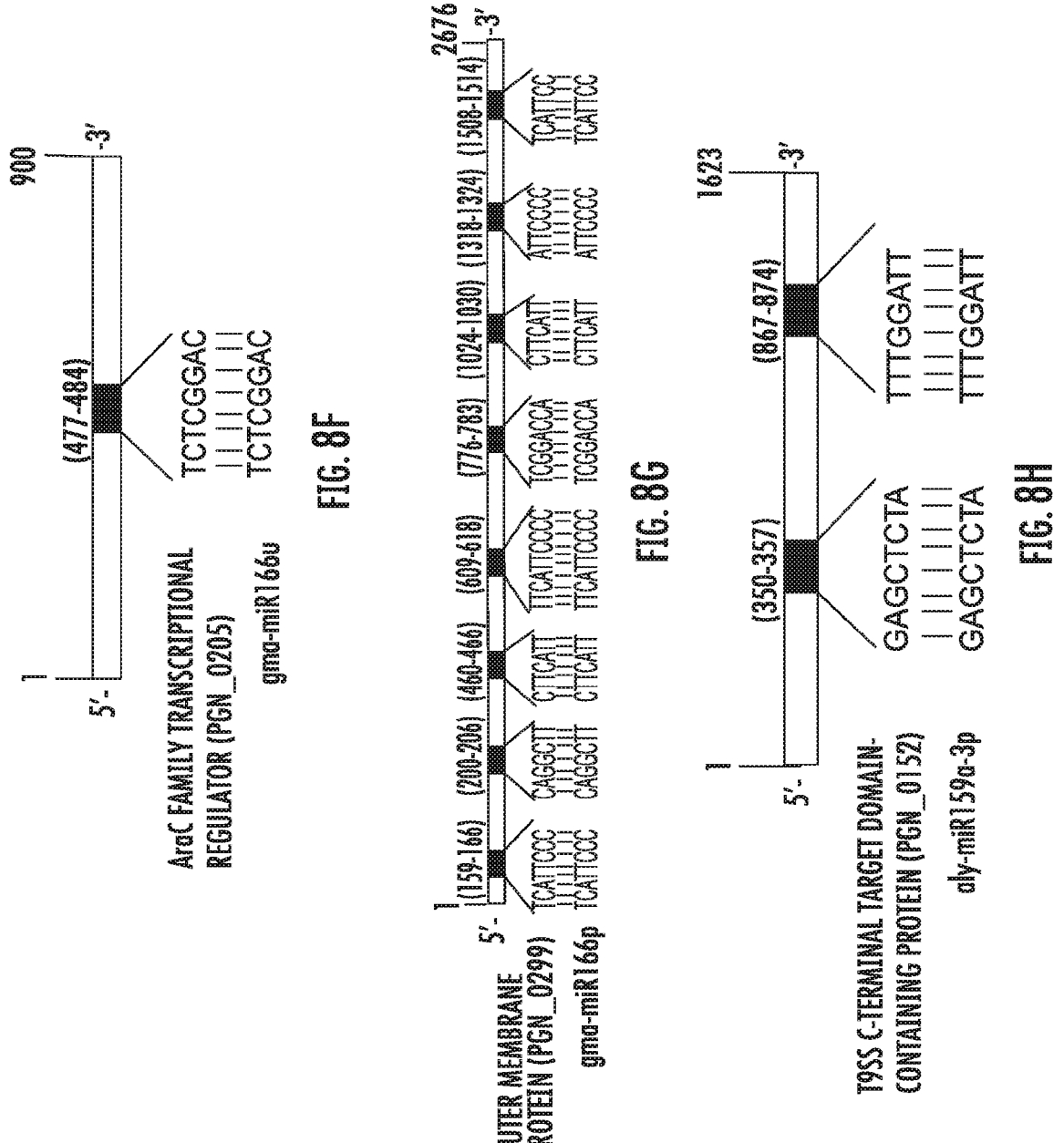

| miRNA_seed | geneSymbol* | old_locus_tag** | Description |
|---|---|---|---|
| | | Aly-miR-159a-3p | |
| TTTGGATT | PGN_RS08230 | PGN_1733 | Hemagglutinin; FIG. 8D |
| TTTGGATT | PGN_RS05900 | PGN_1227 | hypothetical protein |
| TTTGGATT | PGN_RS06005 | PGN_1253 | hypothetical protein |
| TTTGGATT | PGN_RS05790 | PGN_1204 | aspartate 1-decarboxylase |
| TTTGGATT | PGN_RS04300 | PGN_0902 | anaphase-promoting protein subunit 3 |
| TTTGGATT | PGN_RS05310 | | hypothetical protein |
| TTTGGATT | PGN_RS08315 | PGN_1750 | 3-deoxy-manno-octulosonate cytidylyltransferase |
| TTTGGATT | PGN_RS02060 | PGN_0433 | phosphoglycerate kinase |
| TTTGGATT | PGN_RS03450 | PGN_0723 | succinate-semialdehyde dehydrogenase |
| TTTGGATT | PGN_RS01525 | PGN_0318 | precorrin-3B C(17)-methyltransferase |
| TTTGGATT | PGN_RS04735 | PGN_0988 | hypothetical protein |
| TTTGGATT | PGN_RS07385 | PGN_1549 | ATP-dependent Clp protease proteolytic subunit |
| TTTGGATT | PGN_RS03750 | PGN_0786 | hypothetical protein |
| TTTGGATT | PGN_RS06440 | PGN_1349 | S9 family peptidase |
| TTTGGATT | PGN_RS09345 | PGN_1976 | hypothetical protein |
| TTTGGATT | PGN_RS02890 | PGN_0606 | glucosamine-6-phosphate deaminase |
| TTTGGATT | PGN_RS03215 | PGN_0675 | thiazole biosynthesis protein ThiJ |
| TTTGGATT | PGN_RS04470 | PGN_0935 | hypothetical protein |
| TTTGGATT | PGN_RS07600 | PGN_1594 | DNA topoisomerase IV subunit B |
| TTTGGATT | PGN_RS03485 | PGN_0732 | hypothetical protein |
| TTTGGATT | PGN_RS08125 | PGN_1708 | magnesium chelatase |
| TTTGGATT | PGN_RS00715 | PGN_0152 | T9SS C-terminal target domain-containing protein; FIG. 8H |
| TTTGGATT | PGN_RS00200 | PGN_0043 | cell division protein FtsH |
| TTTGGATT | PGN_RS00390 | PGN_0082 | AraC family transcriptional regulator; FIG. 8E |
| TTTGGATT | PGN_RS06580 | PGN_1381 | alanine--tRNA ligase |
| TTTGGATT | PGN_RS00600 | PGN_0128 | hypothetical protein |
| TTTGGATT | PGN_RS05340 | PGN_1115 | hemagglutinin |

TABLE 3-continued

| GELN-derived miRNAs Targeting *P. gingivalis* Genes | | | |
| --- | --- | --- | --- |
| miRNA_seed | geneSymbol* | old_locus_tag** | Description |
| TTTGGATT | PGN_RS00370 | PGN_0079 | hypothetical protein |
| TTTGGATT | PGN_RS04995 | PGN_1042 | cytochrome D ubiquinol oxidase subunit II |
| TTTGGATT | PGN_RS02750 | | mobilization protein |
| TTTGGATT | PGN_RS05560 | PGN_1159 | anaphase-promoting protein subunit 3 |
| TTTGGATT | PGN_RS09285 | PGN_1963 | hypothetical protein |
| TTTGGATT | PGN_RS00415 | PGN_0087 | hypothetical protein |
| TTTGGATT | PGN_RS01490 | PGN_0311 | DUF4271 domain-containing protein |
| TTTGGATT | PGN_RS04225 | PGN_0884 | organic solvent tolerance protein OstA |
| TTTGGATT | PGN_RS09490 | PGN_2005 | hypothetical protein |
| TTTGGATT | PGN_RS00890 | PGN_0192 | membrane protein |
| TTTGGATT | PGN_RS09325 | PGN_1970 | peptidase C25; see FIG. 8A |
| TTTGGATT | PGN_RS09955 | PGN_1340 | hypothetical protein |
| TTTGGATT | PGN_RS01395 | PGN_0291 | VWA domain-containing protein |
| gma-miR166u | | | |
| TCTCGGAC | PGN_RS04795 | PGN_1001 | DNA polymerase III subunit delta |
| TCTCGGAC | PGN_RS00800 | PGN_0172 | hypothetical protein |
| TCTCGGAC | PGN_RS05480 | PGN_1143 | hypothetical protein |
| TCTCGGAC | PGN_RS05135 | PGN_1070 | radical SAM protein |
| TCTCGGAC | PGN_RS06355 | PGN_1330 | branched-chain amino acid ABC transporter ATP-binding protein |
| TCTCGGAC | PGN_RS07035 | PGN_1475 | 5'-methylthioadenosine/S-adenosylhomocysteine nucleosidase |
| TCTCGGAC | PGN_RS05385 | PGN_1124 | paraslipin |
| TCTCGGAC | PGN_RS06240 | PGN_1305 | N-acetylmuramoyl-L-alanine amidase |
| TCTCGGAC | PGN_RS09395 | PGN_1986 | histidinol phosphate phosphatase |
| TCTCGGAC | PGN_RS07020 | PGN_1471 | membrane protein |
| TCTCGGAC | PGN_RS03965 | PGN_0831 | transcription antitermination factor NusB |
| TCTCGGAC | PGN_RS00960 | PGN_0205 | AraC family transcriptional regulator; FIG. 8F |
| TCTCGGAC | PGN_RS08890 | PGN_1874 | 3-phosphoshikimate 1-carboxyvinyltransferase |
| TCTCGGAC | PGN_RS00680 | PGN_0144 | DUF5103 domain-containing protein |
| TCTCGGAC | PGN_RS02140 | PGN_0446 | ABC transporter ATP-binding protein |
| TCTCGGAC | PGN_RS03390 | PGN_0710 | indolepyruvate ferredoxin oxidoreductase |
| TCTCGGAC | PGN_RS05550 | PGN_1157 | lysine--tRNA ligase |

TABLE 3-continued

GELN-derived miRNAs Targeting *P. gingivalis* Genes

| miRNA_seed | geneSymbol* | old_locus_tag** | Description |
|---|---|---|---|
| TCTCGGAC | PGN_RS04840 | PGN_1011 | adenine permease |
| TCTCGGAC | PGN_RS00735 | PGN_0157 | 2-iminoacetate synthase ThiH |
| TCTCGGAC | PGN_RS00090 | PGN_0017 | sodium-independent anion transporter |
| TCTCGGAC | PGN_RS03905 | PGN_0817 | penicillin-binding protein 1A |
| TCTCGGAC | PGN_RS09895 | PGN_2083 | potassium transporter |
| TCTCGGAC | PGN_RS00980 | PGN_0209 | glycine--tRNA ligase |
| TCTCGGAC | PGN_RS01460 | PGN_0303 | peptidase M16 |
| TCTCGGAC | PGN_RS09845 | PGN_2075 | excinuclease ABC subunit A |
| TCTCGGAC | PGN_RS02640 | PGN_0556 | cob altochelatase |
| TCTCGGAC | PGN_RS09725 | PGN_2050 | helicase UvrD | gma-miR166p

| TCGGACCA | PGN_RS01275 | PGN_0264 | signal recognition particle-docking protein FtsY |
| TCGGACCA | PGN_RS01430 | PGN_0299 | outer membrane protein assembly factor; FIG. 8G |
| TCGGACCA | PGN_RS03345 | PGN_0701 | beta-galactosidase |

*geneSymbols noted as PGN_RSxxxxx are *Porphyromonas gingivalis* ATCC 33277 genes for which various information including nucleotide and amino acid sequences can be found by searching the Gene reference of the website of the United States National Center for Biotechnology Information (NCBI). The corresponding database entries and all information included therein are incorporated by reference herein in their entireties.
**old_locus_tags noted as PGN_xxxx correspond to polypeptide sequences from *Porphyromonas gingivalis* ATCC 33277 genes for which various information including the corresponding amino acid sequences can be found by searching the Protein reference of the website of the NCBI. The corresponding database entries and all information included therein are incorporated by reference herein in their entireties.

It was next investigated whether GELN-derived lipids and miRNAs might have synergetic effects on the growth of *P. gingivalis*. However, the results indicated that lipids and miRNA from GELNs did not have synergetic effects with respect to each other.

It was further determined which GELN lipid(s) inhibited the *P. gingivalis* growth. Total lipids were extracted from GELNs ($5.0 \times 10^8$ particles) and were subjected to mass spectrophotometry analysis, with the lipid profile of GELNs summarized in Table 4, and the percentage of each lipid in the overall GELN lipid profile was as follows: 48% PC, 15% PE, 3% PI, 5% PA, 9% TAG, 3% DGDG, 5% MGDG, 7% PG, 3% LysoPG, 1% LysoPE, and 1% LysoPC. Total lipids were also separated on silica gel plates.

TABLE 4

Lipid Profiles of GELNs

| Mass | Compound Formula | Compound Name | nmol per mg dry weight |
|---|---|---|---|
| | | DGDG | |
| 958.6 | $C_{51}H_{88}O_{15}$ | DGDG(36:4) | 138.65 |
| 960.6 | $C_{51}H_{90}O_{15}$ | DGDG(36:3) | 119.80 |
| 936.6 | $C_{49}H_{90}O_{15}$ | DGDG(34:1) | 97.43 |
| 962.6 | $C_{51}H_{92}O_{15}$ | DGDG(36:2) | 57.25 |
| 934.6 | $C_{49}H_{88}O_{15}$ | DGDG(34:2) | 42.90 |
| 956.6 | $C_{51}H_{86}O_{15}$ | DGDG(36:5) | 29.63 |
| 964.7 | $C_{51}H_{94}O_{15}$ | DGDG(36:1) | 22.88 |

TABLE 4-continued

Lipid Profiles of GELNs

| Mass | Compound Formula | Compound Name | nmol per mg dry weight |
|---|---|---|---|
| 984.6 | $C_{53}H_{90}O_{15}$ | DGDG(38:5) | 7.44 |
| 932.6 | $C_{49}H_{86}O_{15}$ | DGDG(34:3) | 5.58 |
| 954.6 | $C_{51}H_{84}O_{15}$ | DGDG(36:6) | 4.87 |
| | | MGDG | |
| 796.6 | $C_{45}H_{78}O_{10}$ | MGDG(36:4) | 286.61 |
| 794.5 | $C_{45}H_{76}O_{10}$ | MGDG(36:5) | 170.49 |
| 798.6 | $C_{45}H_{80}O_{10}$ | MGDG(36:3) | 153.29 |
| 792.5 | $C_{45}H_{74}O_{10}$ | MGDG(36:6) | 91.86 |
| 800.6 | $C_{45}H_{82}O_{10}$ | MGDG(36:2) | 33.08 |
| 774.6 | $C_{43}H_{80}O_{10}$ | MGDG(34:1) | 19.13 |
| 826.6 | $C_{47}H_{84}O_{10}$ | MGDG(38:3) | 13.98 |
| 772.6 | $C_{43}H_{78}O_{10}$ | MGDG(34:2) | 9.17 |
| 822.6 | $C_{47}H_{80}O_{10}$ | MGDG(38:5) | 2.93 |
| | | PG | |
| 768.5 | $C_{40}H_{79}O_{10}P$ | PG(34:0) | 3.71 |
| 766.5 | $C_{40}H_{77}O_{10}P$ | PG(34:1) | 3.30 |
| 764.5 | $C_{40}H_{75}O_{10}P$ | PG(34:2) | 3.11 |
| 740.5 | $C_{38}H_{75}O_{10}P$ | PG(32:0) | 2.23 |
| 788.5 | $C_{42}H_{75}O_{10}P$ | PG(36:4) | 1.82 |
| | | LysoPG | |
| 526.3 | $C_{24}H_{45}O_9P$ | LPG(18:2) | 26.75 |
| 528.3 | $C_{24}H_{47}O_9P$ | LPG(18:1) | 20.15 |
| 500.3 | $C_{22}H_{43}O_9P$ | LPG(16:1) | 15.72 |
| 502.3 | $C_{22}H_{45}O_9P$ | LPG(16:0) | 14.98 |
| 524.3 | $C_{24}H_{43}O_9P$ | LPG(18:3) | 11.47 |

TABLE 4-continued

Lipid Profiles of GELNs

| Mass | Compound Formula | Compound Name | nmol per mg dry weight |
|------|------------------|---------------|------------------------|
| | | LysoPC | |
| 520.3 | $C_{26}H_{50}O_7PN$ | LPC(18:2) | 8.32 |
| 522.3 | $C_{26}H_{52}O_7PN$ | LPC(18:1) | 5.67 |
| | | LysoPE | |
| 478.3 | $C_{23}H_{44}O_7PN$ | LPE(18:2) | 1.27 |
| 454.3 | $C_{21}H_{44}O_7PN$ | LPE(16:0) | 0.43 |
| 452.3 | $C_{21}H_{42}O_7PN$ | LPE(16:1) | 0.37 |
| | | PC | |
| 758.6 | $C_{42}H_{80}O_8PN$ | PC(34:2) | 7.79 |
| 782.6 | $C_{44}H_{80}O_8PN$ | PC(36:4) | 4.77 |
| 784.6 | $C_{44}H_{82}O_8PN$ | PC(36:3) | 2.48 |
| 760.6 | $C_{42}H_{82}O_8PN$ | PC(34:1) | 2.32 |
| 786.6 | $C_{44}H_{84}O_8PN$ | PC(36:2) | 1.08 |
| 756.5 | $C_{42}H_{78}O_8PN$ | PC(34:3) | 0.93 |
| 780.5 | $C_{44}H_{78}O_8PN$ | PC(36:5) | 0.78 |
| | | PE | |
| 716.5 | $C_{39}H_{74}O_8PN$ | PE(34:2) | 1.92 |
| 740.5 | $C_{41}H_{74}O_8PN$ | PE(36:4) | 1.44 |
| 742.5 | $C_{41}H_{76}O_8PN$ | PE(36:3) | 0.22 |
| 828.6 | $C_{47}H_{90}O_8PN$ | PE(42:2) | 0.21 |
| 718.5 | $C_{39}H_{76}O_8PN$ | PE(34:1) | 0.20 |
| | | PI | |
| 852.5 | $C_{43}H_{79}O_{13}P$ | PI(34:2) | 16.28 |
| 876.5 | $C_{45}H_{79}O_{13}P$ | PI(36:4) | 7.98 |
| 854.5 | $C_{43}H_{81}O_{13}P$ | PI(34:1) | 4.37 |
| 878.5 | $C_{45}H_{81}O_{13}P$ | PI(36:3) | 4.08 |
| 850.5 | $C_{43}H_{77}O_{13}P$ | PI(34:3) | 3.44 |
| 824.5 | $C_{41}H_{75}O_{13}P$ | PI(32:2) | 2.65 |
| 874.5 | $C_{45}H_{77}O_{13}P$ | PI(36:5) | 2.50 |
| 828.5 | $C_{41}H_{79}O_{13}P$ | PI(32:0) | 1.99 |
| 822.5 | $C_{41}H_{73}O_{13}P$ | PI(32:3) | 1.91 |
| | | PS | |
| 872.6 | $C_{48}H_{90}O_{10}PN$ | PS(42:2) | 8.61 |
| 760.5 | $C_{40}H_{74}O_{10}PN$ | PS(34:2) | 2.75 |
| 844.6 | $C_{46}H_{86}O_{10}PN$ | PS(40:2) | 1.61 |
| 900.7 | $C_{50}H_{94}O_{10}PN$ | PS(44:2) | 1.35 |
| 874.6 | $C_{48}H_{92}O_{10}PN$ | PS(42:1) | 0.93 |
| 870.6 | $C_{48}H_{88}O_{10}PN$ | PS(42:3) | 0.64 |
| 786.5 | $C_{42}H_{76}O_{10}PN$ | PS(36:3) | 0.54 |
| 784.5 | $C_{42}H_{74}O_{10}PN$ | PS(36:4) | 0.49 |
| | | PA | |
| 690.5 | $C_{37}H_{69}O_8P$ | PA(34:2) | 325.56 |
| 714.5 | $C_{39}H_{69}O_8P$ | PA(36:4) | 219.54 |
| 716.5 | $C_{39}H_{71}O_8P$ | PA(36:3) | 130.51 |
| 692.5 | $C_{37}H_{71}O_8P$ | PA(34:1) | 70.04 |
| 718.5 | $C_{39}H_{73}O_8P$ | PA(36:2) | 39.98 |
| 688.5 | $C_{37}H_{67}O_8P$ | PA(34:3) | 20.51 |
| 712.5 | $C_{39}H_{67}O_8P$ | PA(36:5) | 19.07 |
| 666.5 | $C_{35}H_{69}O_8P$ | PA(32:0) | 2.43 |
| | | DAG | |
| 34:2 | $C_{37}H_{72}O_5N$ | 18:2/16:0 | 68810.79 |
| 34:1 | $C_{37}H_{74}O_5N$ | 18:1/16:0 | 12404.35 |
| 36:4 | $C_{39}H_{72}O_5N$ | 18:2/18:2 | 7971.51 |
| 34:3 | $C_{37}H_{70}O_5N$ | 18:3/16:0 | 7154.70 |
| 36:3 | $C_{39}H_{74}O_5N$ | 18:2/18:1 | 5916.98 |
| 36:2 | $C_{39}H_{76}O_5N$ | 18:2/18:0 | 1695.15 |
| 36:4 | $C_{39}H_{72}O_5N$ | 18:3/18:1 | 1688.38 |
| 36:5 | $C_{39}H_{70}O_5N$ | 18:3/18:2 | 1203.29 |
| 36:2 | $C_{39}H_{76}O_5N$ | 18:1/18:1 | 1163.96 |
| 34:3 | $C_{37}H_{70}O_5N$ | 18:2/16:1 | 401.01 |
| 32:0 | $C_{35}H_{72}O_5N$ | 16:0/16:0 | 365.18 |
| 36:1 | $C_{39}H_{78}O_5N$ | 18:1/18:0 | 251.94 |
| 36:3 | $C_{39}H_{74}O_5N$ | 18:3/18:0 | 124.73 |
| 34:2 | $C_{37}H_{72}O_5N$ | 18:1/16:1 | 118.98 |
| 32:1 | $C_{35}H_{70}O_5N$ | 16:0/16:1 | 118.12 |
| 34:7-O | $C_{37}H_{62}O_6N$ | 18:3/dnOPDA | 82.71 |
| 34:4 | $C_{37}H_{68}O_5N$ | 18:2/16:2 | 82.62 |

TABLE 4-continued

Lipid Profiles of GELNs

| Mass | Compound Formula | Compound Name | nmol per mg dry weight |
|------|------------------|---------------|------------------------|
| 36:6 | $C_{39}H_{68}O_5N$ | 18:3/18:3 | 79.35 |
| 34:4 | $C_{37}H_{68}O_5N$ | 18:3/16:1 | 52.67 |
| 34:5 | $C_{37}H_{66}O_5N$ | 18:2/16:3 | 40.19 |
| 34:3 | $C_{37}H_{70}O_5N$ | 18:1/16:2 | 34.97 |
| 36:7-O | $C_{39}H_{66}O_6N$ | OPDA/18:3 | 22.89 |
| 34:1 | $C_{37}H_{74}O_5N$ | 18:0/16:1 | 15.23 |
| 34:2 | $C_{37}H_{72}O_5N$ | 18:0/16:2 | 15.02 |
| 34:6 | $C_{37}H_{64}O_5N$ | 18:3/16:3 | 13.84 |
| 34:4 | $C_{37}H_{68}O_5N$ | 18:1/16:3 | 13.17 |
| 34:7-O | $C_{37}H_{62}O_6N$ | OPDA/16:3 | 11.43 |
| 34:5 | $C_{37}H_{66}O_5N$ | 18:3/16:2 | 9.84 |
| 34:8-2O | $C_{37}H_{60}O_7N$ | OPDA/dnOPDA | 4.68 |
| 34:3 | $C_{37}H_{70}O_5N$ | 18:0/16:3 | 4.61 |
| | | TAG | |
| 896.76807 | $C_{57}H_{102}O_6N$ | TAG(54:6) | 7.01 |
| 894.75247 | $C_{57}H_{100}O_6N$ | TAG(54:7) | 2.91 |
| 898.78367 | $C_{57}H_{104}O_6N$ | TAG(54:5) | 2.70 |
| 872.76807 | $C_{55}H_{102}O_6N$ | TAG(52:4) | 2.52 |
| 894.75247 | $C_{57}H_{100}O_6N$ | TAG(54:7) | 1.86 |
| 898.78367 | $C_{57}H_{104}O_6N$ | TAG(54:5) | 1.76 |
| 872.76807 | $C_{55}H_{102}O_6N$ | TAG(52:4) | 1.56 |
| 896.76807 | $C_{57}H_{102}O_6N$ | TAG(54:6) | 0.98 |
| 896.76807 | $C_{57}H_{102}O_6N$ | TAG(54:6) | 0.97 |
| 892.73687 | $C_{57}H_{98}O_6N$ | TAG(54:8) | 0.82 |
| 900.79927 | $C_{57}H_{106}O_6N$ | TAG(54:4) | 0.81 |
| 870.75247 | $C_{55}H_{100}O_6N$ | TAG(52:5) | 0.63 |
| 874.78367 | $C_{55}H_{104}O_6N$ | TAG(52:3) | 0.62 |
| 874.78367 | $C_{55}H_{104}O_6N$ | TAG(52:3) | 0.61 |
| 874.78367 | $C_{55}H_{104}O_6N$ | TAG(52:3) | 0.54 |
| 900.79927 | $C_{57}H_{106}O_6N$ | TAG(54:4) | 0.53 |
| 848.76807 | $C_{53}H_{102}O_6N$ | TAG(50:2) | 0.50 |
| 870.75247 | $C_{55}H_{100}O_6N$ | TAG(52:5) | 0.42 |
| 870.75247 | $C_{55}H_{100}O_6N$ | TAG(52:5) | 0.40 |
| 892.73687 | $C_{57}H_{98}O_6N$ | TAG(54:8) | 0.36 |
| 848.76807 | $C_{53}H_{102}O_6N$ | TAG(50:2) | 0.23 |
| 872.76807 | $C_{55}H_{102}O_6N$ | TAG(52:4) | 0.23 |
| 898.78367 | $C_{57}H_{104}O_6N$ | TAG(54:5) | 0.22 |
| 850.78367 | $C_{53}H_{104}O_6N$ | TAG(50:1) | 0.19 |
| 872.76807 | $C_{55}H_{102}O_6N$ | TAG(52:4) | 0.19 |
| 894.75247 | $C_{57}H_{100}O_6N$ | TAG(54:7) | 0.17 |
| 876.79927 | $C_{55}H_{106}O_6N$ | TAG(52:2) | 0.17 |
| 902.81487 | $C_{57}H_{108}O_6N$ | TAG(54:3) | 0.16 |
| 900.79927 | $C_{57}H_{106}O_6N$ | TAG(54:4) | 0.13 |

Which lipids specifically inhibited the growth of pathogenic bacteria was also investigated. *P. gingivalis* was treated with different concentrations (0-50 μg/ml) of PC (34:2), LysoPG (18:1), PA (36:4), PA(36:2), PA(34:2), and PA (34:1). Among these lipids, PA (34:2) inhibited *P. gingivalis* growth at very low concentration (5 μg/ml, $2.5 \times 10^9$ particles have 1 μg of lipid that contains 325.5 nM of PA (34:2) compared to other lipid compounds (see FIG. 4B).

The PA role in the context of GELNs was also tested by depletion of PA. Total GELNs lipids were extracted and separated by TLC with standard PA (34:2). The band corresponding to patent application from the TLC plate was excised and the remaining lipids were pooled together (referred to as "PA depleted lipids"). The role of PA on *P. gingivalis* growth was tested by treating *P. gingivalis* with GELN-derived total lipids (LipidG), the PA-containing band from the TLC plate, and PA-depleted lipids by incubation for 24 hours. Surprisingly, the PA-contained band from the TCL plate alone inhibited *P. gingivalis* growth as potently as total lipids, both of which were statistically significantly more inhibitory that the PA-depleted liposomes (see FIG. 4C). Collectively, these results suggested that PA is an active molecule in GELNs lipids that plays a role in inhibition of *P. gingivalis* growth.

Example 2

GELN PA Directly Interacted with *P. gingivalis* HBP35 Protein, Leading to Inhibition of *P. gingivalis* Growth The molecular mechanism underlying GELN PA-mediated inhibition of *P. gingivalis* growth was investigated. It was hypothesized that GELNs PA lipids might interact with outer membrane proteins of *P. gingivalis* that modulate *P. gingivalis* growth. To test this hypothesis, Surface Plasmon Resonance (SPR) was employed to identify the *P. gingivalis* proteins that interacted with GELNs lipid. Nanoparticles were produced from GELNs total lipids, PA-depleted GELNs nanoparticles, and PA (34:2) were immobilized on an LIP-1 sensor (Nicoya Lifesciences). *P. gingivalis* total cell lysates were prepared and run over the immobilized nanoparticles. Sensograms of SPR peaks revealed that *P. gingivalis* proteins were able to interact with GELNs nanoparticles with or without depletion of PA lipid and PA (34:2). Lipid bound proteins were also eluted by NaH (200 μM) and the fractions were collected for MS/MS analysis of protein identification. PA binding proteins in *P. gingivalis* were identified by MS/MS analysis and the interacting proteins are summarized in Table 5.

ticles. This fraction was collected from the SPR and subjected to MS/MS proteomics analysis for protein identification. Interestingly, several proteins listed in Table 1 were not detected in the PA-depleted nanoparticles but were detected in the GELNs total lipids and PA (34:2). It was determined that PA-interacting *P. gingivalis* proteins including the C-terminal domain of Arg and Lys-gingipain proteases, hemin binding protein (35 kDa), electron transfer flavoprotein, esterase, and outer membrane lipoprotein. These proteins specifically interacted with both GELN nanoparticles and PA.

Which proteins directly interacted with GELNs and played an inhibitory role in *P. gingivalis* growth was also investigated. It has been shown that hemin-binding protein plays an important role in *P. gingivalis* survival and evasion from environmental stress. Therefore, the interaction of GELNs and lipids with hemin binding protein 35 (HIBP35) in *P. gingivalis* growth was tested. The functional domain of THBP35 is WPRVGQLFIALDQTLGIPGFPTFSVCRME (SEQ ID NO: 1) which plays an important role in hemolytic activity of *P. gingivalis*. To block the interaction of GELNs with HIBP35, the functional domain of a HIBP35 synthetic peptide (SEQ ID NO: 1) was employed. GELNs ($4.0 \times 10^8$ particles) were pre-incubated with the synthetic peptide (10 μM) from the functional domain of HBP35. Then, *P. gingi-*

TABLE 5

| | | | PA Interacting *P. gingivalis* Proteins | | |
|---|---|---|---|---|---|
| | | | Quantitative Value (iBAQ) | | |
| Identified Proteins | Gene Symbol | Mol. Weight | GELN NPs | PA-depleted GELN liposome | PA (34:2) liposome |
| CTD of Arg-and Lys-gingipain proteinase | rgpA_4 | 32 kDa | 8269700 | 0 | $5.49 \times 10^7$ |
| Uncharacterized protein | PGN_1182 | 9 kDa | 1974600 | 0 | $4.82 \times 10^6$ |
| Exo-glucosaminidase LytG muramidase | lytG | 36 kDa | 1870800 | 0 | $6.29 \times 10^5$ |
| 35 kDa hemin binding protein | hbp35 | 38 kDa | 540420 | 0 | $1.11 \times 10^7$ |
| Probable transcriptional regulator | asnC | 17 kDa | 428670 | 0 | 0 |
| Electron transfer flavoprotein beta subunit | carD_2 | 29 kDa | 280750 | 0 | $3.75 \times 10^6$ |
| META domain lipoprotein implicated in motility | PGN_0740 | 16 kDa | 215870 | 0 | $1.35 \times 10^6$ |
| Methylmalonyl-CoA decarboxylase-α subunit | pccB | 57 kDa | 195390 | 0 | $2.51 \times 10^6$ |
| 30S ribosomal protein S4 | rpsD | 23 kDa | 190850 | 0 | $2.00 \times 10^6$ |
| Oxygen-insensitive NADPH nitroreductase | rdxA | 20 kDa | 80440 | 0 | 0 |
| Lys-gingipain protease | kgp_1 | 32 kDa | 72555 | 0 | 0 |
| Esterase | estD | 51 kDa | 38153 | 0 | $1.95 \times 10^6$ |
| Outer membrane lipoprotein 42 kDa antigen PG33 | ompA_4 | 75 kDa | 36170 | 0 | 0 |
| Uncharacterized protein | PGN_1697 | 38 kDa | 34827 | 0 | 0 |
| Protein translocase subunit SecA | secA | 127 kDa | 30589 | 0 | 0 |
| NAD-dependent 4-hydroxybutyrate dehydrogenase | adh | 42 kDa | 13268 | 0 | $2.25 \times 10^6$ |
| L-erythro-35-diaminohexanoate dehydrogenase | kdd | 37 kDa | 10490 | 0 | $1.26 \times 10^6$ |
| Chaperone protein DnaK | dnaK | 69 kDa | 6,316.60 | 0 | $2.32 \times 10^4$ |
| Long-chain-fatty-acid--CoA ligase | fadD | 69 kDa | 4,928.30 | 0 | 0 |

The lipid binding proteins were eluted from the immobilized nanoparticles by injection of NaOH (200 μM), which caused a dissociation of proteins from the GELN nanopar-

*valis* was reacted with the GELNs and the growth was measured. Interestingly, *P. gingivalis* growth was not affected by GELNs pre-incubated with HBP35 peptide, whereas GELNs without pretreatment significantly reduced *P. gingivalis* growth (p<0.001 compared to untreated control). Further, GELN total lipids (4.0 and $6.0 \times 10^8$ particles) and PA (34:2) were pre-incubated with HBP35 synthetic peptide and contacted with *P. gingivalis*. The HBP35 synthetic peptide significantly blocked GELN lipid-mediated (p<0.001 for $4.0 \times 10^8$ particles and p<0.01 for $6.0 \times 10^8$ particles) and PA-mediated inhibition of *P. gingivalis* growth (p<0.001 as compared to PA (34:2) without peptide).

Whether the HBP35 synthetic peptide directly bound to PA (34:2) and/or PA (34:1) of GELNs lipids was also tested. To do so, liposomes were made with GELNs total lipids (LipidG), PA depleted GELN lipids, PA (34:2) and PA (34:1). These liposomes were immobilized on LIP-1 senor and HBP35 synthetic peptide was used as an analytes and non-specific peptide used as a negative control. The lipid-protein interactions were determined by SPR sensograms. Fluorescent confocal micrographs of *P. gingivalis* labelled with PKH67 (green fluorescence) and GELNs and LipidG liposomes were labelled with PKH26 (red fluorescence). The labelled particles and liposomes were pre-incubated with synthetic peptide HBP35 (10 μM) for 1 hour at 37° C. The pre-incubated GELNs and liposomes were treated with labelled *P. gingivalis* for 1 hour at 37° C. Particles and liposomes taken up by *P. gingivalis* were visualized by confocal microscopy. Particles and liposomes taken up by *P. gingivalis* were also quantified by flow cytometry. GELNs were reacted with *P. gingivalis* for 1 hour at 37° C., and SPR was utilized for liposomes made from GELN total lipids, PA depletion of GELN lipids, PA (34:2), and PA (34;1) immobilized on an LIP-1 sensor, and the HBP35 synthetic peptide and non-specific peptide were employed as analytes. The SPR sensogram peaks showed that HBP35 synthetic peptide directly interacted with GELNs and PA (34:2) but not with PA-depleted and PA (34:1).

Whether synthetic HBP35 peptide inhibited GELN uptake by *P. gingivalis* was also tested. *P. gingivalis* was fluorescently-labeled with PKH67 (green fluorescence) and GELNs, and LipidG nanoparticles were labelled with PKH26 (red fluorescence). GELNs and LipidG nanoparticles were pre-incubated with HBP35 peptide (10 μM). *P. gingivalis* was reacted with pre-incubated GELNs and LipidG nanoparticles for 1 hour at 37° C. *P. gingivalis* uptake of GELNs and LipidG was visualized by confocal microscopy and quantified by flow cytometry. Interestingly, pre-incubation of synthetic peptide with GELNs and LipidG significantly decreased *P. gingivalis* uptake of GELNs and LipidG as determined by FACS analysis (control 88.9% vs. 23.1% for GELNs pre-incubated with HBP35 peptide, and control 83.3% vs. 29.7% for LipidG pre-incubated with HBP35 peptide).

The HBP35-dependent GELN uptake by *P. gingivalis* was further demonstrated by mutation of HBP35 expressed in *P. gingivalis*. HBP35 expression in *P. gingivalis* was mutated by allelic replacement and the mutant allele was constructed by a PCR fusion technique (see FIG. 6). The HBP35 mutant *P. gingivalis* was incubated with PKH-labelled GELN particles for 1 hour at 37° C. GELN uptake by HBP35 mutant *P. gingivalis* was quantified by flow cytometry, and it was determined that the HBP35 mutant did not take up GELNs (wild type 94.5% vs. mutant 32%). Taken together, the lipid fraction of GELNs, specifically PA (34:2), directly interacted with HBP35 present on the outer membrane of *P. gingivalis*, and this interaction followed by uptake led to inhibition of bacterial growth.

Example 3

GELN miRNAs and Lipids PA (34:2) Inhibited Activity of *P. gingivalis*

Gingipain and *P. gingivalis* Gliding Motility

Besides *P. gingivalis* growth which contributes to its pathogenicity, there are many virulence factors that play a role in pathogenicity of *P. gingivalis*. GELNs are complex nanoparticles, and could interact with multiple *P. gingivalis* virulent factors besides the HBP35 disclosed herein to interact with PA in GELNs. To search for additional *P. gingivalis* factors that could interact with GELNs, biotin-labelled GELNs were incubated with *P. gingivalis* total cell lysates, and the *P. gingivalis* factors that interacted with GELNs were identified. After separation by SDS-PAGE, pulled-down complexes were subjected to MS/MS analysis for identification of *P. gingivalis* proteins that interacted with GELNs. The results are shown in Table 6. The interacting proteins included hemin binding protein 35, lysine and arginine gingipain, hemagglutinin, outer membrane protein A (OMPA), and the T9SS system.

TABLE 6

| GELN Binding Proteins in *P. gingivalis* | | | |
| --- | --- | --- | --- |
| Identified Proteins | Gene Symbol | UniProtKB Accession No.*** | Molecular Weight |
| Lys-gingipain | kgp | KGP_PORG3 | 187 kDa |
| Hemagglutinin | hagA | B2RLK7_PORG3 | 283 kDa |
| Receptor antigen B | ragB | B2RHG8_PORG3 | 57 kDa |
| Cluster of Gingipain R1 | rgpA | CPG1_PORG3 | 185 kDa |
| Receptor antigen A | ragA | B2RHG7_PORG3 | 115 kDa |
| 35 kDa hemin binding protein | hbp35 | | 38 kDa |
| Peptidylarginine deiminase | PGN_0898 | B2RJ72_PORG3 | 62 kDa |
| Immunoreactive 61 kDa antigen | tapA | B2RH26_PORG3 | 61 kDa |
| C-terminal domain of Arg-and Lys-gingipain proteinase | rgpA_4 | B2RHG9_PORG3 | 32 kDa |
| Uncharacterized protein | PGN_0654 | B2RIH8_PORG3 | 35 kDa |
| Zn-carboxypeptidase | scpD | B2RHK9_PORG3 | 92 kDa |
| Minor fimbrium subunit Mfa1 | mfa1 | MFA1_PORG3 | 61 kDa |
| T9SS C-terminal target domain-containing protease | PGN_0458 | B2RHY2_PORG3 | 57 kDa |
| Glyceraldehyde-3-phosphate dehydrogenase | gapA | B2RH47_PORG3 | 36 kDa |

TABLE 6-continued

GELN Binding Proteins in *P. gingivalis*

| Identified Proteins | Gene Symbol | UniProtKB Accession No.*** | Molecular Weight |
|---|---|---|---|
| NAD-specific glutamate dehydrogenase | gdh | DHE2_PORG3 | 49 kDa |
| Uncharacterized protein | PGN_0129 | B2RH03_PORG3 | 22 kDa |
| Outer membrane lipoprotein immunoreactive 42 kDa antigen PG33 | ompA_3 | B2RIQ3_PORG3 | 43 kDa |
| Fibronectin type III domain protein | fib3 | B2RIW9_PORG3 | 79 kDa |
| UDP-N-acetylenolpyruvoyl-glucosamine reductase inner membrane lipoprotein | PGN_1129 | B2RJV3_PORG3 | 17 kDa |
| Lipoprotein | PGN_0426 | B2RHV0_PORG3 | 17 kDa |
| Lysyl endopeptidase | pepK | B2RKP0_PORG3 | 103 kDa |
| Outer membrane lipoprotein immunoreactive 42 kDa antigen PG33 | ompA_2 | B2RIQ2_PORG3 | 42 kDa |
| Uncharacterized protein | PGN_1557 | B2RL31_PORG3 | 30 kDa |
| Ferric enterobactin receptor | pfeA_1 | B2RIK7_PORG3 | 79 kDa |

***these Accession Nos. correspond to polypeptide sequences from Porphyromonas gingivalis gene products for which various information including the corresponding amino acid sequences can also be found by searching the UniProtKB database maintained by the UniProt Consortium, a collaboration between the European Bioinformatics Institute (EMBL-EBI), the SIB Swiss Institute of Bioinformatics, and the Protein Information Resource (PIR). The corresponding database entries and all information included therein are incorporated by reference herein in their entireties.

Gingipains are the most powerful weapons within the *P. gingivalis* arsenal of virulence factors, as they are responsible for nearly 85% of the total *P. gingivalis* proteolytic activity. They are responsible for a variety of pathogenic functions such as colonization, nutrition, neutralization of host defenses, and alteration of the inflammatory response, which all lead to massive oral tissue destruction (i.e., periodontitis) during prolonged infection. The Lys-X (Lys-gingipain) and Arg-X (Arg-gingipain) cysteine proteases of *P. gingivalis* bind and degrade erythrocytes, resulting in formation of black-pigmented colonies on TSB blood agar. Unexpectedly, GELN treatment inhibited the formation of black-pigmented colonies. This result was further supported by the fact that the activities of both arginine-specific (Rgp) and lysine-specific (Kgp) gingipains were significantly decreased in *P. gingivalis* treated with GELNs (Rgp: $p < 0.01$ at $2 \times 10^8$ particles/ml and $p < 0.001$ at $4 \times 10^8$ particles/ml compared to PBS control; Kgp: $p < 0.01$ at both $2 \times 10^8$ particles/ml $4 \times 10^8$ particles/ml compared to PBS control), GELN lipids ($p < 0.01$ at both $2 \times 10^8$ particles/ml $4 \times 10^8$ particles/ml compared to PBS control), PA(34:2; $p < 0.01$ for both Rgp and Kgp as compared to control), and GELN-derived aly-miR159a ($p < 0.01$ for both Rgp and Kgp as compared to control) contributed to inhibit Rgp and Kgp activities.

In addition to gingipain proteinase activity, other virulence factor genes expressed in *P. gingivalis* were examined with respect to GELNs, lipids, and miRNAs derived from GELNs. GELNs strongly inhibited the mRNA encoding AraC transcription factor ($p < 0.01$), hemagglutinin (HA; $p < 0.001$), outer membrane protein A (OMP-A; $p < 0.01$), and Rod shape determining protein A (RodA; $p < 0.01$).

GELN-derived aly-miR159a, and gma-miR166u/p also differentially regulated the mRNA expression of AraC ($p < 0.01$ for aly-miR159a; not significant for gma-miR166u or gma-miR166p), HA ($p < 0.01$ for aly-miR159a; $p < 0.001$ for gma-miR166u and for gma-miR166p), OMP ($p < 0.001$ for aly-miR159a; $p < 0.05$ for gma-miR166u, $p < 0.001$ for gma-miR166p), and RodA ($p < 0.01$ for aly-miR159a; not significant for gma-miR166u or gma-miR166p) in *P. gingivalis*.

In addition, it was determined that aly-miR159a-3p binding sites are present in Hemagglutinin (HA; PGN_1733; see also GENBANK® Accession No. WP_012458492.1, encoded by the complement of nucleotides 1936748-1944634 of GENBANK® Accession No. NC_010729; FIG. 8D), AraC family transcriptional regulator (PGN_0082; see also GENBANK® Accession No. WP_012457226.1, encoded by the complement of nucleotides 86465-87313 of GENBANK® Accession No. NC_010729; FIG. 8E), and gma-166p in the outer membrane protein (OMP; PGN_0299; see also GENBANK® Accession No. WP_012457406.1, encoded by nucleotides 327597-330272 of GENBANK® Accession No. NC_010729; FIG. 8G). This result suggested that miRNA derived from GELNs could have potential binding sites in several virulence genes of *P. gingivalis*.

Further, the effect of GELN-derived lipids and PA (34:2) on AraC, HA, OMP, and RodA mRNA expression was investigated. Lipids derived from GELNs (LipidG) and PA (34:2) inhibited the expression of AraC ($p < 0.001$ for LipidG; $p < 0.01$ for PA(34.2) as compared to DMSO negative control), HA ($p < 0.001$ for LipidG; not significant for PA(34.2) as compared to DMSO negative control), OMP ($p < 0.01$ for LipidG; $p < 0.05$ for PA(34.2) as compared to DMSO negative control), and RodA ($p < 0.01$ for LipidG; $p < 0.05$ for PA(34.2) as compared to DMSO negative control). Collectively, these results indicated that GELN-derived lipids and miRNAs targeted several virulence genes expressed in *P. gingivalis*.

Transferring gingipain from intracellular locations to the cell surface is a critical step in the pathogenesis of *P. gingivalis*. Gingipains are synthesized with an N-terminal signal peptide targeting them to the Sec translocon where they are exported through the outer-membranes via a novel secretion system referred to as type IX Secretion System (T9SS). T9SS plays a critical role in bacterial gliding motility that could contribute to *P. gingivalis* pathogenesis. Therefore, it was determined whether GELNs, GELN-derived miRNAs, and/or GELN lipids could play a role in inhibition of gliding motility of *P. gingivalis*. *P. gingivalis* were pretreated with GELNs ($4.0 \times 10^8$ particles/ml) or PA (34:2; 5 µg/ml) or transduced with GELN-derived aly-miR159a, gma-miR166u, or gma-miR166p. Treated *P. gingivalis* bacteria were inoculated into 'U' shaped glass tubes containing 0.2% agar and incubated for 48 hours at 37° C. in an anaerobic chamber. The movement of *P. gingivalis* was observed in the tube by visualization of cloudiness indicative of bacterial growth, and the extent of movement was measured. Interestingly, GELNs, GELN-derived lipids, and PA(34:2) significantly inhibited the motility of *P. gingivalis* as compared to PBS-treated negative controls ($p<0.001$ for all three), and all three miRNAs significantly inhibited the motility of *P. gingivalis* compared with a scrambled miRNA ($p<0.01$ for aly-miR159a and $p<0.05$ for gma-miR166u and gma-miR166p). These results indicated that GELNs and aly-miR159a strongly inhibited gliding motility of *P. gingivalis*.

To further determine the molecular mechanisms underlying GELN-mediated inhibition of *P. gingivalis* gliding motility, the roles of GELNs, GELNs lipids, and GELN-derived miRNAs in modulating the expression of genes related to T9SS were determined. *P. gingivalis* was treated with GELNs ($4.0 \times 10^8$ particles/ml) and GELNs lipids derived from $4.0 \times 10^8$ particles and 5 µg of PA (34:2) for 6 hours, and miRNAs aly-miR159a, gma-miR166u, and gma-miR166p were transduced into *P. gingivalis* for 24 hours. The expression levels of the T9SS family members porK, porL, porM, porN, porP, porQ, porT, porV, porW, porX, porY, and sov were quantified by qPCR GELNs significantly inhibited the expression of all T9SS family members tested other than porX as compared to control. GELN total lipids significantly inhibited the expression of all T9SS family members tested. In addition, PA (34:2) significantly inhibited the expression of 9/12 T9SS family members tested (not porN, porV, or porX). miRNAs also significantly inhibited the expression of T9SS family members tested as compared to a scrambled miRNA sequence, with aly-miR-159a inhibiting 11/12 (not porY), gma-miR-166u inhibiting 5/11 (porP, porT, porV, porW, and porX), and gma-miR-16p inhibiting 4/11 (porP, porT, porV, porW, and porX). Further, it was determined that aly-miR159a-3p has potential binding sites in the T9SS C-terminal target domain containing protein PGN_0152; see FIG. 8H).

Taken together, these results indicated that GELNs and total lipids derived from GELNs inhibited gene expression of several T9SS family members, and further that the miRNAs set forth herein as well as PA(34:2) preferentially inhibited expression of certain members of the T9SS family of genes that play an important role in gliding motility of *P. gingivalis*.

Example 4

GELNs Inhibited *P. gingivalis* Attachment to and Invasion in Oral Epithelial Cells Disclosed herein is evidence that PA (34:2) inhibited *P. gingivalis* growth, activity of gingipain, and gliding motility in vitro. However, in vivo, multiple factors are involved in pathogenicity of *P. gingivalis* via interaction with host cells, primarily with oral epithelial cells, specifically, the processes involved in attachment and invasion of *P. gingivalis* into oral epithelial cells and subsequently the induction of periodontitis.

Therefore, whether GELNs had an effect on *P. gingivalis* attachment and invasion was investigated. *P. gingivalis* was treated with GELNs ($4 \times 10^8$ particles/ml) at a dose at which *P. gingivalis* was not killed by GELNs, or with PBS as a control, for 1 hour. Human telomerase immortalized gingival keratinocytes (TIGKs) were infected with *P. gingivalis* (MOI of 10) for 1 hour. *P. gingivalis* attachment to TIGK cells was visualized by confocal microscopy, which demonstrated that GELN-treated *P. gingivalis* showed decreased attachment to TIGK cells.

Further, surface attachment of *P. gingivalis* to TIGK was determined by enzyme-linked immunosorbent assay (ELISA) using an anti-*P. gingivalis* antibody, which showed that GELNs treatment significantly decreased surface attachment of *P. gingivalis* to human oral epithelial cells ($p<0.001$ as compared to PBS control).

The major fimbriae, an important virulence factor of *P. gingivalis*, is required for attachment of *P. gingivalis* to oral epithelial cells. Therefore, the effect of GELNs on fimbrillin (fimA) and mfa1 expression in *P. gingivalis* was tested. It was determined that expression of fimA at both the mRNA ($p<0.001$) and protein levels was significantly decreased by GELNs treatment. However, GELNs did not affect mfa1 expression.

After attachment of *P. gingivalis* to the surface of an epithelial cell, *P. gingivalis* can further invade and proliferate therein. Therefore, whether GELNs affected invasion of attached *P. gingivalis* in oral epithelial cells was also tested. *P. gingivalis* was pre-incubated with different concentrations of GELNs ($0$–$6.0 \times 10^8$ particles/ml) for 1 hour, and used to infect TIGK cells at an MOI of 10 for 2 hours. *P. gingivalis* attached to the surface of infected cells were killed by treatment with an antibiotic mixture of gentamycin and metronidazole for 1 hour. The cells were washed, lysed, and plated on TSB blood agar. The number of invaded *P. gingivalis* was quantified by counting colony-forming unit (CFU) on agar plate. Unexpectedly, GELN treatment significantly decreased *P. gingivalis* invasion into oral epithelial cells at $4.0 \times 10^1$ particles/ml ($p<0.001$) and $6.0 \times 10^8$ particles/ml ($p<0.001$), although at $2.5 \times 10^8$ particles/ml, the decrease was not significant. The proliferation assay was performed by incubation of *P. gingivalis*-infected TIGK cells for 24 hours. The extent of *P. gingivalis* proliferation inside TIGK cells was determined by quantitative real-time PCR analysis using standard graph of 16S rRNA expression. The number of *P. gingivalis* inside the TIGK cells at the initial time point (0 hours) and the rate of proliferation was determined at 24 hours. Interestingly, GELNs significantly inhibited the proliferation of *P. gingivalis* in oral epithelial cells ($p<0.01$ as compared to a PBS negative control).

Next, which GELN factors contributed to inhibit the attachment and invasion of *P. gingivalis* into oral epithelial cells was determined. First, the role of GELNs lipids on *P. gingivalis* attachment, invasion, and proliferation of *P. gingivalis* was investigated. *P. gingivalis* were pre-treated with GELN-derived total lipids (from $4.0 \times 10^8$ particles) and 50 nM of PA (34:2), which was equivalent to $4.0 \times 10^8$ particles. After 1 hour at this concentration, it was observed that *P. gingivalis* was not killed by GELN-derived lipids. The surface attachment of *P. gingivalis* was determined as described above. Interestingly, both GELN-derived total lipids and PA (34:2) significantly inhibited surface attachment of *P. gingivalis* onto TIGK cells ($p<0.001$ for each as compared to DMSO control). Further, *P. gingivalis* were treated with the same concentration of lipids for 6 hours and fimA expression was determined by western blot and real-time PCR analysis. FimA expression was significantly decreased in both GELNs total lipids and PA (34:2) treated *P. gingivalis* ($p<0.01$ for each as compared to DMSO control).

The effect of GELNs total lipids and PA (34:2) on *P. gingivalis* invasion and proliferation in TIGK cells was also investigated. A significant decrease in *P. gingivalis* invasion into TIGK cells was observed in both GELNs total lipids and PA-treated *P. gingivalis* (p<0.001 for each as compared to DMSO control). The proliferation of *P. gingivalis* in TIGK cells was significantly inhibited by GELN total lipids as compared to PA (p<0.01). Collectively, these results demonstrated that GELN PA (34:2) inhibited the growth, attachment, and invasion of *P. gingivalis*.

To test whether GELNs miRNAs play an inhibitory role in attachment and invasion of *P. gingivalis*, miRNAs gma-miR166u, gma-miR166p, and aly-miR159a were transduced into *P. gingivalis* by packaging the miRNAs into liposomes as described herein. The transduced cells were cultured for 24 hours. A scrambled sequence miRNA was used as a negative control. Among the three miRNAs tested, aly-miR159a significantly decreased surface attachment of *P. gingivalis* onto TIGK cells (p<0.01 as compared to a scrambled control sequence), and gma-miR166u and gma-166p moderately inhibited surface attachment to *P. gingivalis* (p<0.05 for both as compared to a scrambled control sequence).

Expression of hemagglutinin, RodA, AraC, and outer membrane proteins play an important role in attachment of *P. gingivalis* to TIGK cells, and were inhibited by GELN miRs (see FIG. 7A).

Next, the effect of these miRs on *P. gingivalis* proliferation in TIGK cells was tested. The proliferation of *P. gingivalis* was more strongly inhibited by aly-miRNA159a (p<0.001 as compared to a scrambled control sequence) as compared to the other two miRNAs (p<0.001 as compared to a scrambled control sequence) Although GELN miRNAs including aly-miR159a had no effect on *P. gingivalis* growth, these miRNAs inhibited attachment and invasion of *P. gingivalis* into oral epithelial cells by regulating virulence gene expression (see FIG. 7B). Collectively, these results demonstrated that GELNs and total lipids derived from GELNs, including GELN-derived miRNAs, targeted expression of several virulence factors in *P. gingivalis* and inhibited its pathogenicity.

Example 5

GELNs Inhibited *P. gingivalis*-Induced Bone Loss in an In Vivo Mouse Model It has been shown that *P. gingivalis* is strongly associated with alveolar bone loss and development of periodontitis. Therefore, the effect of GELNs and GELN-derived miRNAs on *P. gingivalis*-induced alveolar bone loss in vivo was tested. It is important to know whether *P. gingivalis* in mouse oral cavity is capable of taking up GELNs that modulate *P. gingivalis* growth in this mouse model. Fluorescently-labeled (PKH67) *P. gingivalis* was inoculated into the oral cavity of mice followed by fluorescently-labeled (PKH26) GELNs. After 1 hour incubation, the oral cavity was washed with PBS and the oral content was collected to determine *P. gingivalis* uptake of GELNs. Flow cytometry and confocal microscopy analyses showed that *P. gingivalis* in the mouse oral cavity was able to take up GELNs (positive cells accounted for 54.7% of the cells at $2\times10^8$ particles/ml, 64% of the cells at $3\times10^8$ particles/ml, 80.5% of the cells at $4\times10^8$ particles/ml, 83% of the cells at $5\times10^8$ particles/ml, and 83.8% of the cells at $6\times10^8$ particles/ml.

Next, the biological effects of taking up GELNs on bone loss were examined. *P. gingivalis* was pretreated with GELNs ($4\times10^8$ particles/ml) for 1 hour to allow *P. gingivalis* to take up the GELNs. In a murine oral infection model, *P.*

*gingivalis* was orally infected every 2 days for a period of 10 days, with the mice being monitored continuously. A group of mice was given GELNs in drinking water ad libitum until the mice were sacrificed at 3 weeks. The number of *P. gingivalis* in the oral cavities of the mice was determined by real-time PCR. The number of *P. gingivalis* in the oral cavity was significantly decreased (p<0.001) in GELN-treated mice compared to the control group of mice.

After 47 days of treatment, a second group of mice were sacrificed, and μCT analysis was determined alveolar bone loss by measuring the distance from the centennial enamel junction (CEJ) to the alveolar bone crest (ABC). Interestingly, GELNs drastically decreased alveolar bone loss compared to mice infected with *P. gingivalis* alone (see FIG. 9A). Further, GELN-alone treated mice showed better quality of bone than naïve mice treated with PBS. Histology of bone sections showed that *P. gingivalis*-enhanced alveolar bone loss measured by distance between tooth surface and alveolar bone represented periodontal ligament length. Surprisingly, GELNs significantly decreased *P. gingivalis*-induced bone loss as represented by a decreased periodontal ligament length (p<0.001 as compared to a PBS negative control; see also see FIG. 9B).

Next, cytokine expression modulated by *P. gingivalis* and GELNs in mouse plasma was assayed. Cytokine array analysis revealed that GELNs significantly decreased *P. gingivalis*-activated inflammatory and pro-inflammatory cytokines, including TNF-α, IL-1α, IL-1β, INF-γ, IL-6, IL-10, Il-13, and IL-22 (see FIG. 10). These cytokines play an important role in recruiting inflammatory Th17 T cells and macrophages into bone tissues, leading to bone loss.

Next, the effect of GELNs on T cells and macrophages in the bone was tested. The alveolar section of the bone was subjected to immunofluorescence staining of CD3 and F4/80 to detect T cells and macrophages, respectively. As shown in FIGS. 9C and 9D, *P. gingivalis* infection enhanced infiltration of T cells and macrophages in periodontal tissues, and GELNs significantly decreased T cells and macrophage infiltration into these tissues. Furthermore, real-time PCR analysis showed that GELNs significantly decreased the *P. gingivalis*-induced inflammatory cytokines IL-1β, IL-6, IL-8, and TNF-α in the oral tissue of *P. gingivalis* infected mice (p<0.001 for each cytokine as compared to *P. gingivalis* positive controls). Taken together, these results demonstrated that GELNs potentially targeting *P. gingivalis*, which inhibited *P. gingivalis* pathogenicity and thereby decreased alveolar bone loss, protected against inflammation caused by periodontal diseases.

Discussion of the Examples

Plant exosome-like particles protect plants against pathogen infections and whether edible plant exosomes can protect mammalian host against pathogen infection is not known. Disclosed herein it is shown that ginger exosome-like nanoparticles (GELNs) are selectively up taken by *Porphyromonas gingivalis* (*P. gingivalis*) in a GELN phosphatidic acid (PA) dependent manner via interaction with hemin binding protein 35 (HBP35) on the *P. gingivalis* surface. Compared with PA(34:2), PA(34:1) did not interact with HBP35, indicating that the degree of unsaturation of PA played an important role in GELN-mediated interaction with HBP35. Upon binding to HBP35, the pathogenicity of *P. gingivalis* was significantly reduced via interaction with GELN cargo molecules including PA and miRs. These cargo molecules interacted with multiple pathogenic factors in recipient bacteria simultaneously. Using edible plant exosome-like nanoparticles as potential therapeutic agents to prevent and/or treat chronic periodontitis was further demonstrated in mouse models.

As disclosed herein, GELNs were selectively taken up by pathogenic *P. gingivalis*. This selectivity was determined by GELN-derived lipid PA, which interacted with hemin binding protein 35 (HBP35) expressed on the external surface of pathogenic *P. gingivalis*. HBP35 plays a critical role in hemin utilization and interaction with host. It has been shown that HBP35 involved in coaggregation of *P. gingivalis* with various oral Gram-positive and Gram-negative bacteria, which contributes to attachments to host and development of biofilm formation and progression of disease pathogenicity. The results disclosed herein showed that GELN PA had a direct interaction with HBP35, leading to inhibition of *P. gingivalis* growth.

This conclusion was further supported by the fact that depletion of PA from GELNs or mutation of *P. gingivalis* HBP35 led to no HBP35/PA interaction and contributed to no disruption of the pathogenic *P. gingivalis* membrane. In addition, pre-incubation of HBP35 peptide with GELNs led to canceling GELN-mediated inhibition of growth of *P. gingivalis*. At the molecular level, the specificity of PA binding to HBP35 was dependent on the degree of unsaturation of PA. PA(34:2) was preferred by *P. gingivalis*, whereas PA (34:1) was preferred by *Lactobacillus* GG (LGG), suggesting that the degree of unsaturation of PA determined the specificity of PA binding to various bacterial species.

It has been shown that PA recruited and activated effector molecules that change the biophysical properties of the mammalian cell membrane and directly induce membrane destabilization. The effect of PA on the bacterial membrane has not been not reported before. Collectively, these results suggested that GELN PA was required for selective uptake by *P. gingivalis* via interaction with the HBP35 domain. This finding is significant since the selective uptake feature can be utilized for not only targeting specific bacteria but also delivering therapeutic agents to specific pathogens for treatment.

It is known that a healthy diet is important for maintaining oral and gut microbiota homeostasis and further that an unhealthy diet can cause dysbiosis. Recent work indicated that GELNs promoted LGG growth and inhibited growth of other bacterial species. However, the molecular mechanism underlying these phenomena is not clear. As disclosed herein, lipid analysis of GELN compositions indicated that both PA (34:2) and PA(34:1) are presented on GELNs and GELNs can be taken up by both LGG and by *P. gingivalis*. The results presented herein suggested that there are at least two factors that contribute to the selectivity of GELN-mediated biological effects on GELN recipient bacteria. One is the number of unsaturated bonds of PA, and another is the availability of GELN-targeted molecules presented in the recipient bacteria. Once GELNs enter cells, miRs and lipids released from GELNs interact with bacterial factors including mRNAs and proteins. Since LGG has different mRNA and protein expression profiles from *P. gingivalis*, it is conceivable that which species of bacteria takes up GELNs could be dependent on the numbers of unsaturated PA on GELNs, and the biological effects on the GELN recipient bacteria could be dependent on the availability of factors presented in the recipient bacteria.

Previous studies have shown that both secreted and surface associated proteins contribute to the determination of virulence in *P. gingivalis*. Arg-gingipain and Lys-gingipain and hemagglutinin are considered as major virulence factors of *P. gingivalis*. As disclosed herein, GELNs and its component lipids and miRNAs significantly decreased the gingipain activities and hemagglutinin expression in *P. gingivalis*. Further, it was determined that miR-159a-3p has several potential binding sites in the 3-UTR of genes encoding gingipain and hemagglutinin. This finding permits the further study of the molecular mechanisms underlying how plant exosome-like particles might inhibit oral bacterial pathogenicity via plant miR interactions with pathogenic factors such as gingipain and hemagglutinin. This interaction is not only restricted to plant exosome-like particle miRs, but other GELN molecules might also participate in inhibition of bacterial pathogenicity.

Furthermore, it has been determined that GELN PA binding to the C-terminal domain (CTD) of gingipain might inhibit gingipain biological activities and hemagglutinin expression. In addition to these virulent factors, GELNs, lipids, and miRNAs from GELNs can also inhibit other virulent factor expressions such as OMPA, rod shape determining protein A (RodA), and AraC transcription family regulators. The AraC family of transcription regulators is one of the largest group of regulatory proteins in bacteria, which also control expression of several virulence factors.

Another vital behavioral feature in bacteria is gliding motility, which plays an important role in biofilm formation and virulence. The Type IX secretion system (T9SS) plays an important role in *P. gingivalis* gliding motility. The Type IX secretion system is a family of proteins that are composed of several outer membranes, periplasmic and inner membrane proteins that play roles in gingipain secretion, and that transport other virulence factors to the host environment, and knockdown of these proteins leads to inactive gingipain and non-pigmented colony formation. As disclosed herein, it was observed that GELNs and its lipids and miRNAs significantly decreased the expression of T9SS and gliding motility of *P. gingivalis*. Collectively, the findings presented herein suggested that GELNs carry a broad spectrum of molecules, including lipids and miRNAs, that are capable of inhibiting the pathogenicity of *P. gingivalis* by targeting multiple pathways of *gingivalis*.

The interaction of bacterial factors with host cells also contributes to a bacterial species' pathogenicity. It has been shown that *P. gingivalis* has the capability of adhering in the oral cavity for bacterial colonization. Several *P. gingivalis* proteins including major fimbriae (fimA) and minor fimbriae (mfa1) play a role in attachment to of the bacterium to host cells. The ability of *P. gingivalis* to adhere was decreased by mutation of the fimA gene, which prevented periodontitis. The present disclosure showed that GELNs and its component lipids and miRNAs significantly decreased fimA expression and further decreased attachment of *P. gingivalis* to oral epithelial cells. Also disclosed is the finding that GELNs treatment significantly decreased *P. gingivalis*-induced alveolar bone loss in a mouse model. Collectively, the presently disclosed subject matter supports the hypothesis that a healthy diet including edible plant-derived exosome-like nanoparticles packaging agents can target multiple virulence factors of infectious agents, simultaneously leading to prevention and treatment of infectious disease.

Since most biological process observed required multifactor participation, the process regulated by GELNs is likely to be more efficient than any single molecule. The present disclosure thus also opens a new avenue for studying the roles of ELNs in selectivity of bacteria for regulating oral and gut bacterial homeostasis. It is known that a healthy diet including ginger is important for maintaining gut microbiota homeostasis and unhealthy an diet can promote dysbiosis.

However, the molecular mechanisms underlying how a healthy diet maintains oral microbiota homeostasis is not clear. The results presented herein suggested that a healthy diet including plant-derived exosome-like nanoparticles can play a role in maintaining oral and gut microbiota homeostasis by inhibiting growth of potential harmful bacteria as well as increasing beneficial bacterial survival. Such mechanisms can be applied to edible plant exosome-like nanoparticles in general since most edible plants contain ELNs. Depending on how frequently specific edible plant exosomes-like nanoparticles are exposed to bacteria in the digestive system, the biological effects on the recipient bacteria could be transient or irreversible.

In addition, currently, only a few gut and oral bacteria can be grown in the laboratory in pure cultures. Systematic approach to find growth conditions of as yet unculturable bacteria is challenging. The present disclosure, however, will open up new avenues for investigating the possibility of in vitro co-culturing oral and gut bacteria with ELNs for enhancing survivability of these bacteria.

In this study, the finding that GELNs preferentially affected the expression of major fimbriae fimA but not mfa1 provides a foundation for further identifying GELN factor that selectively regulate the expression of fimA. It was also determined that GELNs treatment led to decreased recruitment of macrophages and CD3 cells into the bone microenvironment, thus decreasing expression of the inflammatory cytokines IL-1β, IL-6, IL-8, and TNF-α. This GELN-mediated immune modulation could occur through direct interaction of GELNs with CD3 T cells and macrophages and/or through metabolites released by GELNs positive oral bacteria.

It was also found that naïve mice treated with GELNs in drinking water had better quality of bone than naïve mice treated with PBS. This finding opens a new avenue to study how GELNs can improve the quality of bone in general since decreasing quality of bone in general is associated with many diseases.

As disclosed herein, GELNs were selectively taken up by the periodontal pathogen *Porphyromonas gingivalis* in a GELN PA-dependent manner via interactions with the bacterial hemin binding35 (Hbp35). The food we consume daily contains ELNs, and the compositions of ELNs from different types of food are different. As a consequence, the biological effects on consumers resulting from food consumption will also be different based on the totality of ELNs consumed. Therefore, based on the personalized profile of food consumption by any individual, it is possible to customize and/or personalize a given individual's ELN intake to prevent and/or treat diseases, disorder, and conditions and where desirable, to supplement desirable ELN intakes and reduce undesirable ELN intakes via selective oral administration of ELN-containing compositions and foods.

REFERENCES

All references cited in the instant disclosure, including but not limited to all patents, patent applications and publications thereof, scientific journal articles, and database entries (e.g., GENBANK® database entries and all annotations available therein, including but not limited to comments with respect to genes, coding sequences (CDS) and nucleotides corresponding thereto, encoded amino acid sequences, and GENBANK® Accession Nos. included therein) are incorporated herein by reference in their entireties to the extent that they supplement, explain, provide a background for, or teach methodology, techniques, and/or compositions employed herein.

Acuna-Amador et al. (2018) Genomic repeats, misassembly and reannotation: a case study with long-read resequencing of *Porphyromonas gingivalis* reference strains. BMC Genomics 19, Article 54.

Barturen et al. (2014) sRNAbench: profiling of small RNAs and its sequence variants in single or multi-species high-throughput experiments. Methods Next-Generation Seq1: 21-31.

GENBANK® Accession Nos. NC_010729 (*Porphyromonas gingivalis* ATCC 33277, complete genomic sequence); WP_004565167.1; WP_012457226.1; WP_012457406.1; WP_012458492.1.

Martin (2011) Cutadapt removes adapter sequences from high-throughput sequencing reads. EMBnet.journal 17(1):10-12.

PCT International Patent Application Publication No. WO 2019/104242.

Sundaram et al. (2019) Plant-Derived Exosomal Nanoparticles Inhibit Pathogenicity of *Porphyromonas gingivalis*. iScience 22; 21:308-327.

U.S. Patent Application Publication Nos. 2005/0036954; 2006/0034780; 2007/0066552; 2009/0026673; 2011/0038809; 2012/0315324; 2014/0050675; 2014/0308212; 2017/0035700; 2018/0140654; 2018/0362974.

U.S. Pat. Nos. 6,200,550; 6,455,031; 6,830,745; 7,087,661; 7,314,854; 8,945,518; 9,717,733; 9,848,600; 10,004,676; 10,300,173.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for inhibiting and/or treating periodontitis or oral disease associated with a *Porphyromonas gingivalis* (*P. gingivalis*) infection, the method comprising administering to the oral cavity of a subject in need thereof a composition comprising a ginger-derived exosome-like nanoparticles (GELNs) or a biologically active component thereof; wherein the GELN can be obtained in bands between the 8%/30% layer and the 30%/45% layer of a sucrose step gradient; and wherein the GELN or the biologically active component is provided in an amount that is therapeutically effective for the inhibition and/or treatment of periodontitis or oral disease associated with a *P. gingivalis* infection.

2. The method of claim 1, wherein the biologically active component comprises a lipid, a protein, an miRNA, or a combination thereof.

3. The method of claim 2, wherein the biologically active component comprises one or more miRNAs, optionally wherein the one or more miRNAs comprise an miR-159a-3p miRNA.

4. The method of claim 2, wherein the biologically active component comprises one or more lipids, optionally wherein the one or more lipids comprises phosphatidic acid (PA).

5. The method of claim 4, wherein the one or more lipids comprises PA (34:2).

6. A method for reducing growth of *Porphyromonas gingivalis* (*P. gingivalis*) in the oral cavity of a subject, the method comprising administering to the oral cavity of the subject a composition comprising a ginger-derived exosome-like nanoparticles (GELNs) or a biologically active component thereof; wherein the GELN can be obtained in bands between the 8%/30% layer and the 30%/45% layer of a sucrose step gradient; and wherein the GELN or the biologically active component is provided in an amount that is therapeutically effective for the inhibition and/or treatment of periodontitis or oral disease associated with a *P. gingivalis* infection.

7. The method of claim 6, wherein the biologically active component comprises a lipid, a protein, an miRNA, or a combination thereof.

8. The method of claim 6, wherein the biologically active component comprises one or more miRNAs, optionally wherein the one or more miRNAs comprise an miR-159a-3p miRNA.

9. The method of claim 6, wherein the biologically active component comprises one or more lipids, optionally wherein the one or more lipids comprises phosphatidic acid (PA).

10. The method of claim 9, wherein the one or more lipids comprises PA (34:2).

\* \* \* \* \*

SEQUENCE LISTING

```
<160> NUMBER OF SEQ ID NOS: 59

<210> SEQ ID NO 1
<211> LENGTH: 29
<212> TYPE: PRT
<213> ORGANISM: Porphyromonas gingivalis

<400> SEQUENCE: 1

Trp Pro Arg Val Gly Gln Leu Phe Ile Ala Leu Asp Gln Thr Leu Gly
1               5                   10                  15

Ile Pro Gly Phe Pro Thr Phe Ser Val Cys Arg Met Glu
            20                  25
```

-continued

```
<210> SEQ ID NO 2
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 2
gatgagccga cgatgagtat gc                                                22

<210> SEQ ID NO 3
<211> LENGTH: 46
<212> TYPE: DNA
<213> ORGANISM: Artificial Sequence
<220> FEATURE:
<223> OTHER INFORMATION: Artificially synthesized oligonucleotide primer

<400> SEQUENCE: 3
gaagctatcg ggggtaccttt gcaaatactt tgcctctgtt atcgtc                     46

<210> SEQ ID NO 4
<211> LENGTH: 51
<212> TYPE: DNA
<213> ORGANISM: Artificial Sequence
<220> FEATURE:
<223> OTHER INFORMATION: Artificially synthesized oligonucleotide primer

<400> SEQUENCE: 4
tgtccctgaa aaatttcatc ctattgagct aagatttaaa cgaaaactgc g               51

<210> SEQ ID NO 5
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 5
aatgctcggt ttcagtgtct gc                                                22

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 6
ggttaccccc gatagcttcc                                                   20

<210> SEQ ID NO 7
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 7
ggatgaaatt tttcagggac a                                                 21

<210> SEQ ID NO 8
<211> LENGTH: 23
<212> TYPE: DNA
<213> ORGANISM: Artificial Sequence
<220> FEATURE:
<223> OTHER INFORMATION: Artificially synthesized oligonucleotide primer
```

-continued

```
<400> SEQUENCE: 8
tactctctgc tgctatccta agt                                           23

<210> SEQ ID NO 9
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 9
cctccaacac cacattcttc t                                             21

<210> SEQ ID NO 10
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 10
gcttccggta gcgatgataa                                               20

<210> SEQ ID NO 11
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 11
cacctccaca tactcgtcat ac                                            22

<210> SEQ ID NO 12
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 12
tggcttatcg tggctctttc                                               20

<210> SEQ ID NO 13
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 13
ggaggatctc ttctgcatca c                                             21

<210> SEQ ID NO 14
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 14
aggaactccg attgcgaagg                                               20

<210> SEQ ID NO 15
```

-continued

```
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 15
tcgtttactg cgtggactac c                                              21

<210> SEQ ID NO 16
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 16
cgcgaactct tctgcatctt                                                20

<210> SEQ ID NO 17
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 17
gaatacgaag gcacgaaagc                                                20

<210> SEQ ID NO 18
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 18
ggatcgttcg cttcagatgt                                                20

<210> SEQ ID NO 19
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 19
agccatgatg gaaattttgg                                                20

<210> SEQ ID NO 20
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 20
cgattataag ggacggatcg                                                20

<210> SEQ ID NO 21
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 21
```

```
ccatcatgaa aaggtgggat a                                               21

<210> SEQ ID NO 22
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 22
gatcgatgct gatggtgatg                                                 20

<210> SEQ ID NO 23
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 23
ccgctagcag tccatgattt                                                 20

<210> SEQ ID NO 24
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 24
gatcggggac agaagtacca                                                 20

<210> SEQ ID NO 25
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 25
attcgggtag gcgaagaagt                                                 20

<210> SEQ ID NO 26
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 26
agaattgagg atgccgaatg                                                 20

<210> SEQ ID NO 27
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 27
tgcatacgag cctttctcct                                                 20

<210> SEQ ID NO 28
<211> LENGTH: 20
<212> TYPE: DNA
```

```
<213> ORGANISM: Artificial Sequence
<220> FEATURE:
<223> OTHER INFORMATION: Artificially synthesized oligonucleotide primer

<400> SEQUENCE: 28
gggtgctctc ttcaagttgc                                           20

<210> SEQ ID NO 29
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 29
tccatcggat tcttcgagtc                                           20

<210> SEQ ID NO 30
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 30
ttccgtcaca gctcaatcag                                           20

<210> SEQ ID NO 31
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 31
atttcacgct tacccaaacg                                           20

<210> SEQ ID NO 32
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 32
tcgctcgtga acgagtaatg                                           20

<210> SEQ ID NO 33
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 33
gaatcgggcg taggacagta                                           20

<210> SEQ ID NO 34
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 34
agctcaatcc ggatcaaatg                                           20
```

-continued

```
<210> SEQ ID NO 35
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 35
gatgatattg ccgctttcgt                                                   20

<210> SEQ ID NO 36
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 36
ctcagtccgg acaggagaag                                                   20

<210> SEQ ID NO 37
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 37
ctgcaggaaa tcggcattat                                                   20

<210> SEQ ID NO 38
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 38
aggcggcaga gactatgaaa                                                   20

<210> SEQ ID NO 39
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 39
ctgataaacc tgcccgttgt                                                   20

<210> SEQ ID NO 40
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 40
atgcgtttcc tgaactacgg                                                   20

<210> SEQ ID NO 41
<211> LENGTH: 20
<212> TYPE: DNA
<213> ORGANISM: Artificial Sequence
<220> FEATURE:
```

-continued

<223> OTHER INFORMATION: Artificially synthesized oligonucleotide primer

<400> SEQUENCE: 41
caccaaggcc aaaggaacta                                               20

<210> SEQ ID NO 42
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 42
agctactgac gggcacagtt                                               20

<210> SEQ ID NO 43
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 43
aaagcatagc cggcatagaa                                               20

<210> SEQ ID NO 44
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 44
ggtctcggat gcgattttta                                               20

<210> SEQ ID NO 45
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 45
ctcgaaattg aacgtgagca                                               20

<210> SEQ ID NO 46
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 46
ctctgtgcca tcgctgaata                                               20

<210> SEQ ID NO 47
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 47
agaaaccggt catctgcatc                                               20

```
<210> SEQ ID NO 48
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 48
cattgacatt gcaggtggag                                                           20

<210> SEQ ID NO 49
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 49
tcgaacatga agtcgaggtg                                                           20

<210> SEQ ID NO 50
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 50
ttgttgggac ttgctgctct tg                                                        22

<210> SEQ ID NO 51
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 51
ttcggctgat ttgatggctt cc                                                        22

<210> SEQ ID NO 52
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 52
gttcccatta gacaactgc                                                            19

<210> SEQ ID NO 53
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 53
gattctttcc tttgaggc                                                             18

<210> SEQ ID NO 54
<211> LENGTH: 20
<212> TYPE: DNA
<213> ORGANISM: Artificial Sequence
<220> FEATURE:
<223> OTHER INFORMATION: Artificially synthesized oligonucleotide primer
```

-continued

```
<400> SEQUENCE: 54
gataccactc ccaacagacc                                              20

<210> SEQ ID NO 55
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 55
gcaatggcaa ttctgattgt                                              20

<210> SEQ ID NO 56
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 56
tctatggccc agaccctcac                                              20

<210> SEQ ID NO 57
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 57
gacggcagag aggaggttga                                              20

<210> SEQ ID NO 58
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 58
aggtcatccc agagctgaac g                                            21

<210> SEQ ID NO 59
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 59
accctgttgc tgtagccgta t                                            21
```